US012336843B2

(12) United States Patent
Zhou

(10) Patent No.: US 12,336,843 B2
(45) Date of Patent: Jun. 24, 2025

(54) MULTI-PARAMETER PREDICTION OF ACUTE CARDIAC EPISODES AND ATTACKS

(71) Applicant: Medtronic, Inc., Minneapolis, MN (US)

(72) Inventor: Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/663,589

(22) Filed: May 16, 2022

(65) Prior Publication Data

US 2022/0273236 A1 Sep. 1, 2022

Related U.S. Application Data

(63) Continuation of application No. 16/673,390, filed on Nov. 4, 2019, now Pat. No. 11,850,063, which is a
(Continued)

(51) Int. Cl.
*A61B 5/00* (2006.01)
*A61B 5/0205* (2006.01)
(Continued)

(52) U.S. Cl.
CPC .......... *A61B 5/4836* (2013.01); *A61B 5/0022* (2013.01); *A61B 5/0031* (2013.01);
(Continued)

(58) Field of Classification Search
CPC ...... G16H 50/30; G16H 50/20; A61B 5/4836; A61B 5/316; A61B 5/0022; A61B 5/0031;
(Continued)

(56) References Cited

U.S. PATENT DOCUMENTS

| 5,117,824 A | 6/1992 | Keimel et al. |
| 5,545,186 A | 8/1996 | Olson et al. |

(Continued)

FOREIGN PATENT DOCUMENTS

| WO | 2010014063 A1 | 2/2010 |
| WO | 2013055732 A1 | 4/2013 |

OTHER PUBLICATIONS (PCT/US2017/037152) PCT Notification of Transmittal of the International Search Report and the Written Opinion of the International Searching Authority, Mailed Sep. 29, 2017, 10 pages.
(Continued)

*Primary Examiner* — Michael J Lau
(74) *Attorney, Agent, or Firm* — Shumaker & Sieffert, P.A.

(57) ABSTRACT

In some examples, processing circuitry of a medical device system determines, for each of a plurality of patient parameters, a difference metric for a current period based on a value of a patient parameter determined for the current period and a value of the patient parameter determined for an immediately preceding period, and determines a score for the current period based on a sum of the difference metrics for at least some of the plurality of patient parameters. The processing circuitry determines a threshold for the current period based on scores determined for N periods that precede the current period, compares the score for the current period to the threshold, and determines whether to generate an alert indicating that an acute cardiac event of the patient, e.g., ventricular tachyarrhythmia, is predicted, and/or deliver a therapy configured to prevent the acute cardiac event, based on the comparison.

25 Claims, 27 Drawing Sheets

Related U.S. Application Data continuation of application No. 15/620,346, filed on Jun. 12, 2017, now Pat. No. 10,463,295.

(60) Provisional application No. 62/349,504, filed on Jun. 13, 2016.

(51) Int. Cl.

| | | |
|---|---|---|
| *A61B 5/085* | (2006.01) | |
| *A61B 5/316* | (2021.01) | |
| *A61B 5/363* | (2021.01) | |
| *A61N 1/05* | (2006.01) | |
| *A61N 1/39* | (2006.01) | |
| *G16H 50/20* | (2018.01) | |
| *G16H 50/30* | (2018.01) | |
| *A61B 5/11* | (2006.01) | |
| *A61B 5/145* | (2006.01) | |
| *A61N 1/372* | (2006.01) | |
| *A61N 1/375* | (2006.01) | |

(52) U.S. Cl.
CPC ........ *A61B 5/0205* (2013.01); *A61B 5/02055* (2013.01); *A61B 5/086* (2025.01); *A61B 5/316* (2021.01); *A61B 5/363* (2021.01); *A61B 5/4839* (2013.01); *A61B 5/686* (2013.01); *A61B 5/7225* (2013.01); *A61B 5/7275* (2013.01); *A61B 5/7282* (2013.01); *A61B 5/7435* (2013.01); *A61B 5/746* (2013.01); *A61N 1/0563* (2013.01); *A61N 1/395* (2013.01); *A61N 1/3962* (2013.01); *A61N 1/3987* (2013.01); *G16H 50/20* (2018.01); *G16H 50/30* (2018.01); *A61B 5/1116* (2013.01); *A61B 5/14542* (2013.01); *A61B 2562/0204* (2013.01); *A61B 2562/0219* (2013.01); *A61B 2562/0261* (2013.01); *A61N 1/37229* (2013.01); *A61N 1/37235* (2013.01); *A61N 1/37288* (2013.01); *A61N 1/37512* (2017.08); *A61N 1/3756* (2013.01); *A61N 1/39622* (2017.08)

(58) Field of Classification Search
CPC . A61B 5/0205; A61B 5/02055; A61B 5/0809; A61B 5/4839; A61B 5/686; A61B 5/7225; A61B 5/7275; A61B 5/7435; A61B 5/7282; A61B 5/746; A61B 5/1116; A61B 5/14542; A61B 2562/0204; A61N 1/0563; A61N 1/395; A61N 1/3962; A61N 1/3987; A61N 1/39622; A61N 1/37229; A61N 1/37288; A61N 1/3756
USPC ........................................................ 600/301
See application file for complete search history.

(56) References Cited

U.S. PATENT DOCUMENTS

| | | | |
|---|---|---|---|
| 5,755,736 A | 5/1998 | Gillberg et al. | |
| 6,223,073 B1* | 4/2001 | Seegobin | A61B 5/7264 600/515 |
| 6,334,065 B1 | 12/2001 | Al-Ali et al. | |
| 6,922,585 B2 | 7/2005 | Zhou et al. | |
| 7,027,856 B2 | 4/2006 | Zhou et al. | |
| 7,054,692 B1* | 5/2006 | Whitehurst | A61N 1/37518 607/116 |
| 7,231,244 B2 | 6/2007 | Laitio et al. | |
| 7,330,750 B2 | 2/2008 | Erkkila et al. | |
| 7,629,889 B2 | 12/2009 | Sachanandani | |
| 7,689,283 B1* | 3/2010 | Schecter | A61B 7/00 607/18 |
| 7,725,184 B2 | 5/2010 | Cazares | |
| 7,860,559 B2 | 12/2010 | Fischell et al. | |
| 7,949,412 B1* | 5/2011 | Harrison | A61N 1/0541 607/136 |
| 8,255,046 B2 | 8/2012 | Sarkar et al. | |
| 8,374,686 B2 | 2/2013 | Ghanem et al. | |
| 8,460,189 B2* | 6/2013 | Libbus | A61B 5/327 600/386 |
| 8,521,268 B2 | 8/2013 | Zhang et al. | |
| 8,603,010 B2 | 12/2013 | Lange et al. | |
| 8,838,215 B2 | 2/2014 | John et al. | |
| 8,744,572 B1 | 6/2014 | Greenhut et al. | |
| 8,781,566 B2 | 7/2014 | John et al. | |
| 8,932,220 B2 | 1/2015 | Ong et al. | |
| 10,463,295 B2 | 11/2019 | Zhou | |
| 2002/0087055 A1* | 7/2002 | Rowlandson | A61B 5/349 600/301 |
| 2003/0130586 A1 | 7/2003 | Starobin et al. | |
| 2003/0191403 A1 | 10/2003 | Zhou et al. | |
| 2005/0115561 A1* | 6/2005 | Stahmann | A61N 1/3601 128/204.23 |
| 2005/0148896 A1* | 7/2005 | Siejko | A61B 7/04 600/528 |
| 2005/0149136 A1* | 7/2005 | Siejko | A61B 5/4836 607/17 |
| 2006/0106322 A1* | 5/2006 | Arand | A61B 5/318 600/514 |
| 2006/0247547 A1 | 11/2006 | Sarkar et al. | |
| 2007/0260285 A1* | 11/2007 | Libbus | A61B 5/02158 607/9 |
| 2008/0058662 A1 | 3/2008 | Beise | |
| 2009/0076402 A1 | 3/2009 | Hoium et al. | |
| 2009/0228298 A1* | 9/2009 | Xue | G16H 40/67 705/2 |
| 2010/0030292 A1 | 2/2010 | Sarkar et al. | |
| 2010/0030293 A1 | 2/2010 | Sarkar et al. | |
| 2010/0056940 A1 | 3/2010 | Moorman et al. | |
| 2010/0094252 A1 | 4/2010 | Wengreen et al. | |
| 2010/0113889 A1* | 5/2010 | Ghanem | A61N 1/36564 600/301 |
| 2010/0114208 A1 | 5/2010 | Donofrio et al. | |
| 2010/0121399 A1* | 5/2010 | McCabe | A61N 1/36053 607/17 |
| 2010/0234749 A1* | 9/2010 | Gregg | A61B 5/318 600/509 |
| 2010/0280850 A1 | 11/2010 | Sherashova | |
| 2011/0009760 A1* | 1/2011 | Zhang | G16H 10/60 600/529 |
| 2011/0046498 A1 | 2/2011 | Klap et al. | |
| 2011/0213215 A1 | 9/2011 | Doyle et al. | |
| 2012/0029587 A1* | 2/2012 | Zhou | A61N 1/3937 607/17 |
| 2012/0209082 A1 | 8/2012 | Al-Ali | |
| 2012/0271177 A1* | 10/2012 | Emerson | A61B 5/029 600/528 |
| 2012/0271372 A1 | 10/2012 | Osorio | |
| 2012/0283705 A1* | 11/2012 | Lee | A61N 1/372 606/1 |
| 2013/0041275 A1 | 2/2013 | Syed et al. | |
| 2013/0237863 A1* | 9/2013 | Song | A61B 7/003 607/18 |
| 2013/0289430 A1 | 10/2013 | Song et al. | |
| 2013/0297219 A1* | 11/2013 | Bangera | G16H 50/30 702/19 |
| 2014/0088442 A1 | 3/2014 | Soykan et al. | |
| 2014/0155762 A1* | 6/2014 | Maskara | A61B 7/04 600/528 |
| 2014/0276928 A1 | 9/2014 | Vanderpool et al. | |
| 2014/0364756 A1* | 12/2014 | Brockway | A61B 5/316 600/513 |
| 2015/0080670 A1 | 3/2015 | Osorio | |
| 2015/0112606 A1 | 4/2015 | He et al. | |
| 2015/0190087 A1 | 7/2015 | Shinar et al. | |
| 2015/0223760 A1 | 8/2015 | Greifer | |
| 2015/0282723 A1* | 10/2015 | Bachmann | A61B 5/329 600/500 |
| 2015/0305634 A1* | 10/2015 | Stergiou | A61B 5/02405 600/509 |

(56) References Cited

U.S. PATENT DOCUMENTS

| | | | |
|---|---|---|---|
| 2016/0029913 A1* | 2/2016 | Smith | A61B 5/316 600/523 |
| 2016/0038093 A1 | 2/2016 | Sharma et al. | |
| 2016/0045166 A1* | 2/2016 | Gheeraert | A61B 5/318 600/509 |
| 2016/0128638 A1 | 5/2016 | Altini et al. | |
| 2016/0135706 A1 | 5/2016 | Sullivan et al. | |
| 2016/0302732 A1 | 10/2016 | Misra et al. | |
| 2017/0273634 A1 | 9/2017 | Hotta et al. | |
| 2017/0281082 A1 | 10/2017 | Khine et al. | |
| 2017/0290550 A1 | 10/2017 | Perschbacher et al. | |
| 2019/0231207 A1 | 8/2019 | Perschbacher et al. | |
| 2020/0069245 A1 | 3/2020 | Zhou | |
| 2020/0357519 A1 | 11/2020 | Chakravarthy et al. | |
| 2022/0273236 A1 | 5/2022 | Zhou | |

OTHER PUBLICATIONS

Prosecution History from U.S. Appl. No. 15/620,346, dated Jun. 28, 2017 through Jun. 24, 2019, 49 pp.
Prosecution History from U.S. Appl. No. 16/673,390, dated Mar. 25, 2020 through Feb. 2, 2022, 30 pp.
Notice of Allowance from U.S. Appl. No. 16/673,390 dated Aug. 24, 2022, 8 pp.
Final Office Action from U.S. Appl. No. 16/673,390, dated May 24, 2022, 12 pp.
Gupta P et al., "T(p-e)/QT ratio as an index of arrhythmogenesis", Journal of Electrocardiology, vol. 41, No. 6, Nov. 2008, pp. 567-574.
Response to Final Office Action mailed May 24, 2022, from U.S. Appl. No. 16/673,390, filed Jul. 18, 2022, 6 pp.
Final Office Action from U.S. Appl. No. 16/673,390 dated Dec. 1, 2022, 12 pp.
Office Action from U.S. Appl. No. 16/673,390 dated Feb. 3, 2023, 12 pp.
U.S. Appl. No. 17/813,393, filed Jul. 19, 2022, by Zhou.
Response to Office Action dated Feb. 3, 2023 from U.S. Appl. No. 16/673,390, filed Apr. 24, 2023, 7 pp.
Communication pursuant to Article 94(3) EPC from counterpart European Application No. 20173454.8 dated Jul. 17, 2023, 4 pp.
Notice of Allowance from U.S. Appl. No. 16/673,390 dated Aug. 9, 2023, 10 pp.
Corrected Notice of Allowance from U.S. Appl. No. 16/673,390 dated Sep. 1, 2023, 2 pp.
Response to Communication pursuant to Article 94(3) EPC dated Jul. 17, 2023, from counterpart European Application No. 20173454.8 filed Nov. 9, 2023, 14 pp.
Corrected Notice of Allowance from U.S. Appl. No. 16/673,390 dated Nov. 15, 2023, 2pp.
Office Action from U.S. Appl. No. 17/813,393 dated Aug. 27, 2024, 33 pp.
Response to Office Action dated Aug. 27, 2024 from U.S. Appl. No. 17/813,393, filed Nov. 27, 2024, 18 pp.

* cited by examiner

270

| Day | Parameter 1 | Parameter 2 | ... | Parameter 8 |
|---|---|---|---|---|
| 0 | $V_{0,param_1}$ | $V_{0,param_2}$ | ... | $V_{0,param_8}$ |
| -1 | $V_{-1,param_1}$ | $V_{-1,param_2}$ | ... | $V_{-1,param_8}$ |
| -2 | $V_{-2,param_1}$ | $V_{-2,param_2}$ | ... | $V_{-2,param_8}$ |
| ... | ... | ... | ... | ... |

Sum ⇒

| Sum of square |
|---|
| $score_0$ |
| $score_{-1}$ |
| $score_{-2}$ |
| ... | improper direction?     irrelevant parameter?

FIG. 12

| Device Serial Number | Threshold (2x median score) | True Negative (Normal) | False Negative (Missed) | True Positive (Hit) | False Positive (False alarm) | Sensitivity | Specificity |
|---|---|---|---|---|---|---|---|
| BLI603035S | 17.3716 | 188 | 6 | 10 | 52 | 62.50% | 78.30% |
| BWD605665S | 15.5545 | 128 | 0 | 1 | 34 | 100% | 79.00% |
| BWD601015S | 14.43 | 216 | 0 | 3 | 58 | 100% | 78.80% |
| BWD601506S | 13.0296 | 173 | 0 | 0 | 47 | N/A | 78.60% |
| PGZ600999S | 15.9523 | 178 | 0 | 0 | 50 | N/A | 78.10% |
| PSD604135S | 14.1692 | 262 | 1 | 1 | 88 | 50% | 74.90% |
| PSD604818S | 13.8553 | 172 | 4 | 8 | 51 | 66.70% | 77.10% |
| PSD604827S | 18.6542 | 198 | 0 | 1 | 56 | 100% | 78.00% |
| PSD605084S | 12.4895 | 266 | 0 | 5 | 104 | 100% | 71.90% |
| PSD607272S | 13.9446 | 226 | 0 | 0 | 61 | N/A | 78.70% |
| PSD607732S | 8.9981 | 202 | 0 | 0 | 89 | N/A | 69.40% |
| PSD608235S | 16.6687 | 211 | 0 | 0 | 45 | N/A | 82.40% |
| PSD608351S | 17.1106 | 91 | 2 | 0 | 23 | 0 | 79.80% |
| PSD609152S | 13.0523 | 151 | 0 | 0 | 63 | N/A | 70.60% |
| PSD609748S | 14.0825 | 132 | 0 | 0 | 35 | N/A | 79.00% |
| PSE609564S | 9.61386 | 144 | 1 | 0 | 48 | 0 | 75.00% |
| TOTAL | | 2938 | 14 | 29 | 904 | 67.40% | 76.50% |

| Device Serial Number | True Negative (Normal) | False Negative (Missed) | True Positive (Hit) | False Positive (False alarm) | All events Sensitivity | All events Specificity | Shock events Count | Shock events Predicted | ATP events Count | ATP events Predicted |
|---|---|---|---|---|---|---|---|---|---|---|
| BLI603035S | 179 | 0 | 25 | 52 | 100.00% | 77.49% | 1 | 1 | 39 | 39 |
| BWD605666S | 108 | 0 | 2 | 53 | 100.00% | 67.08% | 2 | 2 | 0 | |
| BWD601015S | 206 | 0 | 3 | 68 | 100.00% | 75.18% | 6 | 6 | 0 | |
| BWD601506S | 160 | 0 | 0 | 60 | NaN | 72.73% | 0 | | 0 | |
| PGZ600998S | 158 | 0 | 0 | 70 | NaN | 69.30% | 0 | | 0 | |
| PSD604135S | 265 | 0 | 2 | 85 | 100.00% | 75.71% | 1 | 1 | 3 | 3 |
| PSD604818S | 161 | 0 | 14 | 60 | 100.00% | 72.85% | 12 | 12 | 24 | 24 |
| PSD604827S | 181 | 0 | 1 | 73 | 100.00% | 71.26% | 11 | 11 | 0 | |
| PSD605084S | 271 | 0 | 3 | 101 | 100.00% | 72.85% | 1 | 1 | 1 | 1 |
| PSD607272S | 216 | 0 | 0 | 71 | NaN | 75.26% | 0 | | 0 | |
| PSD607732S | 202 | 0 | 0 | 89 | NaN | 69.42% | 0 | | 0 | |
| PSD608235S | 182 | 0 | 0 | 74 | NaN | 71.09% | 0 | | 0 | |
| PSD608351S | 81 | 0 | 1 | 34 | 100.00% | 70.43% | 0 | | 2 | 2 |
| PSD609152S | 159 | 0 | 0 | 55 | NaN | 74.30% | 0 | | 0 | |
| PSD609748S | 128 | 0 | 0 | 39 | NaN | 76.65% | 0 | | 0 | |
| PSE609564S | 143 | 0 | 2 | 48 | 100.00% | 74.87% | 0 | | 1 | 1 |
| TOTAL | 2800 | 0 | 53 | 1032 | 100% | 73% | | | | |

FIG. 19

| Device Serial Number | True Negative (Normal) | False Negative (Missed) | True Positive (Hit) | False Positive (False alarm) | All events | | Shock events | | ATP events | |
|---|---|---|---|---|---|---|---|---|---|---|
| | | | | | Sensitivity | Specificity | Count | Predicted | Count | Predicted |
| BLI603035S | 184 | 3 | 17 | 52 | 85.00% | 77.97% | 1 | 1 | 39 | 35 |
| BWD600566S | 127 | 0 | 2 | 34 | 100.00% | 78.88% | 2 | 2 | 0 | |
| BWD601015S | 220 | 0 | 2 | 55 | 100.00% | 80.00% | 6 | 6 | 0 | |
| BWD601506S | 169 | 0 | 0 | 51 | NaN | 76.82% | 0 | | 0 | |
| PGZ600998S | 186 | 0 | 0 | 42 | NaN | 81.58% | 0 | | 0 | |
| PSD604135S | 290 | 0 | 2 | 60 | 100.00% | 82.86% | 1 | 1 | 3 | 3 |
| PSD604818S | 173 | 1 | 13 | 48 | 92.86% | 78.28% | 12 | 10 | 24 | 24 |
| PSD604827S | 180 | 0 | 1 | 74 | 100.00% | 70.87% | 11 | 11 | 0 | |
| PSD605084S | 271 | 0 | 4 | 100 | 100.00% | 73.05% | 1 | 1 | 1 | 1 |
| PSD607272S | 219 | 0 | 0 | 68 | NaN | 76.31% | 0 | | 0 | |
| PSD607732S | 225 | 0 | 0 | 66 | NaN | 77.32% | 0 | | 0 | |
| PSD608235S | 203 | 0 | 0 | 53 | NaN | 79.30% | 0 | | 0 | |
| PSD608351S | 86 | 0 | 1 | 29 | 100.00% | 74.78% | 0 | | 2 | 2 |
| PSD609152S | 163 | 0 | 0 | 51 | NaN | 76.17% | 0 | | 0 | |
| PSD609748S | 130 | 0 | 0 | 37 | NaN | 77.84% | 0 | | 0 | |
| PSE609564S | 143 | 1 | 0 | 49 | 0.00% | 74.48% | 0 | | 1 | 0 |
| TOTAL | 2969 | 5 | 42 | 869 | 89% | 77% | | | | |

| Patient ID | True Negative (Normal) | False Negative (Missed) | Total FN episodes (VT+VF) | True Positive (Hit) | Total TP episodes (VT+VF) | False Positive (False alarm) | All events Sensitivity | All events Specificity | Shock events Count | Shock events Episodes | Shock events Predicted | ATP events Count | ATP events Episodes | ATP events Predicted |
|---|---|---|---|---|---|---|---|---|---|---|---|---|---|---|
| PMH-01-HYY | 136 | 0 | 0 | 0 | 0 | 44 | N/A | 76.0% | 0 | 0 | 0 | 0 | 0 | 0 |
| PMH-02-YKY | 138 | 0 | 0 | 1 | 1 | 41 | 100.0% | 77.1% | 0 | 0 | 0 | 1 | 1 | 1 |
| PMH-03-LYS | 125 | 0 | 0 | 3 | 26 | 52 | 100.0% | 70.6% | 9 | 9 | 9 | 17 | 17 | 17 |
| PMH-04-WYW | 108 | 0 | 0 | 0 | 0 | 55 | N/A | 67.1% | 0 | 0 | 0 | 0 | 0 | |
| PMH-05-HH | File err | File err | File err | File err | File err | File err | File err | File err | | | | | | |
| PMH-06-LHS | 131 | 0 | 0 | 3 | 6 | 46 | 100.0% | 74.0% | 6 | 6 | 6 | 0 | 0 | 0 |
| PMH-07-YCM | 125 | 0 | 0 | 0 | 0 | 55 | N/A | 69.4% | 0 | 0 | 0 | 0 | 0 | |
| PMH-08-LKH | 130 | 0 | 0 | 0 | 0 | 50 | N/A | 72.2% | 0 | 0 | 0 | 0 | 0 | |
| PMH-09-CSS | 133 | 0 | 0 | 2 | 2 | 45 | 100.0% | 74.7% | 0 | 0 | 0 | 1 | 1 | 1 |
| PMH-10-CKF | 81 | 0 | 0 | 1 | 1 | 34 | 100.0% | 70.4% | 0 | 0 | 0 | 1 | 1 | 1 |
| PMH-11-CKK | 130 | 0 | 0 | 0 | 0 | 50 | N/A | 72.2% | 0 | 0 | 0 | 0 | 0 | |
| PMH-12-LNF | File err | File err | File err | File err | File err | File err | File err | File err | 0 | 0 | ??? | 23 | 23 | ??? |
| PMH-13-NYC | 128 | 0 | 0 | 0 | 0 | 39 | N/A | 76.7% | 0 | 0 | 0 | 0 | 0 | |
| PMH-14-CKW | 128 | 0 | 0 | 4 | 7 | 45 | 100.0% | 74.0% | 3 | 3 | 3 | 1 | 1 | 1 |
| PMH-15-SYS | Early exit | Early exit | Early exit | Early exit | Early exit | Early exit | Early exit | Early exit | | | | | | |
| PMH-19-NCK | 48 | 0 | 0 | 0 | 0 | 19 | N/A | 71.6% | 0 | 0 | 0 | 0 | 0 | |
| QEH-01-CY | 130 | 0 | 0 | 0 | 0 | 50 | N/A | 72.2% | 0 | 0 | 0 | 0 | 0 | |
| QEH-03-KCN | 142 | 0 | 0 | 0 | 0 | 38 | N/A | 78.9% | 0 | 0 | 0 | 0 | 0 | |
| QEH-04-TWL | 130 | 0 | 0 | 0 | 0 | 50 | N/A | 72.2% | 0 | 0 | 0 | 0 | 0 | |
| QEH-05-LK | 132 | 0 | 0 | 12 | 35 | 36 | 100.0% | 78.6% | 1 | 1 | 1 | 34 | 34 | 34 |
| QEH-07-LM | File err | File err | File err | File err | File err | File err | File err | File err | | | | | | |
| QEH-09-PMY | 128 | 0 | 0 | 0 | 0 | 42 | N/A | 71.1% | 0 | 0 | 0 | 0 | 0 | |
| QEH-10-KTN | 134 | 0 | 0 | 0 | 0 | 46 | N/A | 74.4% | 0 | 0 | 0 | 0 | 0 | |
| QEH-11-MSN | File err | File err | File err | File err | File err | File err | File err | File err | 4 | 4 | ??? | 21 | 21 | ??? |
| QEH-12-CSS | 152 | 0 | 0 | 1 | 1 | 27 | 100.0% | 84.4% | 0 | 0 | 0 | 1 | 1 | 1 |
| TOTAL | 2489 | 0 | 0 | 30 | | 874 | 100.0% | 74.0% | | | | | | |

FIG. 21

| Patient ID | True Negative (Normal) | False Negative (Missed) | Total FN episodes (VT+VF) | True Positive (Hit) | Total TP episodes (VT+VF) | False Positive (False alarm) | All events Sensitivity | All events Specificity | Shock events Count | Shock events Episodes | Shock events Predicted | ATP events Count | ATP events Episodes | ATP events Predicted |
|---|---|---|---|---|---|---|---|---|---|---|---|---|---|---|
| PMH-01-HYY | 143 | 0 | 0 | 0 | 0 | 37 | N/A | 79.9% | 0 | 0 | 0 | 0 | 0 | 0 |
| PMH-02-YKY | 129 | 0 | 0 | 2 | 1 | 49 | 100.0% | 72.5% | 0 | 0 | 0 | 1 | 1 | 1 |
| PMH-03-LYS | 137 | 0 | 0 | 3 | 26 | 40 | 100.0% | 77.4% | 9 | 9 | 9 | 17 | 17 | 17 |
| PMH-04-WYW | 127 | 0 | 0 | 0 | 0 | 36 | N/A | 78.9% | 0 | 0 | 0 | 0 | 0 | 0 |
| PMH-05-HH | File err | File err | File err | File err | File err | File err | File err | File err | | | | | | |
| PMH-06-LHS | 143 | 0 | 0 | 2 | 6 | 35 | 100.0% | 80.3% | 6 | 6 | 6 | 0 | 0 | 0 |
| PMH-07-YCM | 135 | 0 | 0 | 0 | 0 | 45 | N/A | 75.0% | 0 | 0 | 0 | 0 | 0 | 0 |
| PMH-08-LKH | 142 | 0 | 0 | 0 | 0 | 38 | N/A | 78.9% | 0 | 0 | 0 | 0 | 0 | 0 |
| PMH-09-CSS | 131 | 1 | 1 | 0 | 0 | 48 | 0.0% | 73.2% | 0 | 0 | 0 | 1 | 1 | 1 |
| PMH-10-CKF | 86 | 0 | 0 | 1 | 1 | 29 | 100.0% | 74.8% | 0 | 0 | 0 | 1 | 1 | 1 |
| PMH-11-CKK | 134 | 0 | 0 | 0 | 0 | 46 | N/A | 74.4% | 0 | 0 | 0 | 0 | 0 | 0 |
| PMH-12-LNF | File err | File err | File err | File err | File err | File err | File err | File err | 0 | 0 | ??? | 23 | 23 | ??? |
| PMH-13-NYC | 130 | 0 | 0 | 0 | 0 | 37 | N/A | 77.8% | 0 | 0 | 0 | 0 | 0 | 0 |
| PMH-14-CKW | 141 | 1 | 1 | 5 | 3 | 33 | 83.3% | 81.0% | 3 | 3 | 3 | 1 | 1 | 0 |
| PMH-15-SYS | Early exit | Early exit | Early exit | Early exit | Early exit | Early exit | Early exit | Early exit | | | | | | |
| PMH-19-NCK | 48 | 0 | 0 | 0 | 0 | 19 | N/A | 71.6% | 0 | 0 | 0 | 0 | 0 | 0 |
| QEH-01-CY | 125 | 0 | 0 | 0 | 0 | 55 | N/A | 69.4% | 0 | 0 | 0 | 0 | 0 | 0 |
| QEH-03-KCN | 138 | 0 | 0 | 0 | 0 | 42 | N/A | 76.7% | 0 | 0 | 0 | 0 | 0 | 0 |
| QEH-04-TWL | 147 | 0 | 0 | 0 | 0 | 33 | N/A | 81.7% | 0 | 0 | 0 | 0 | 0 | 0 |
| QEH-05-LK | 134 | 2 | 3 | 6 | 32 | 38 | 75.0% | 77.9% | 1 | 1 | 1 | 34 | 34 | 31 |
| QEH-07-LM | File err | File err | File err | File err | File err | File err | File err | File err | | | | | | |
| QEH-09-PMY | 152 | 0 | 0 | 0 | 0 | 28 | N/A | 84.4% | 0 | 0 | 0 | 0 | 0 | 0 |
| QEH-10-KTN | 137 | 0 | 0 | 0 | 0 | 43 | N/A | 76.1% | 0 | 0 | 0 | 0 | 0 | 0 |
| QEH-11-MSN | File err | File err | File err | File err | File err | File err | File err | File err | 4 | 4 | ??? | 21 | 21 | ??? |
| QEH-12-CSS | 139 | 0 | 0 | 1 | 1 | 40 | 100.0% | 77.2% | 0 | 0 | 0 | 1 | 1 | 1 |
| TOTAL | 2598 | 4 | | 20 | | 771 | 83.3% | 77.1% | | | | | | |

| r | Sensitivity | Specificity | Sensitivity | Specificity | Sensitivity | Specificity |
|---|---|---|---|---|---|---|
| 1.00 | 100.00 | 53.26 | 100.00 | 52.83 | 100.00 | 54.31 |
| 1.25 | 98.28 | 61.14 | 100.00 | 60.48 | 100.00 | 59.73 |
| 1.50 | 98.21 | 67.85 | 96.36 | 67.75 | 100.00 | 64.36 |
| 1.75 | 94.12 | 73.24 | 94.44 | 73.11 | 100.00 | 68.52 |
| 2.00 | 89.36 | 77.36 | 87.50 | 77.98 | 100.00 | 73.07 |
| 2.25 | 84.09 | 80.68 | 61.90 | 81.58 | 94.00 | 75.85 |
| 2.50 | 58.54 | 84.08 | 60.98 | 84.21 | 89.58 | 78.92 |
| 2.75 | 56.10 | 86.24 | 52.50 | 86.53 | 84.44 | 80.94 |
| 3.00 | 41.03 | 88.25 | 36.84 | 88.85 | 79.55 | 82.76 |

FIG. 23

MULTI-PARAMETER PREDICTION OF ACUTE CARDIAC EPISODES AND ATTACKS

This application is a Continuation of U.S. patent application Ser. No. 16/673,390 (published as U.S. Patent Publication No. 2020/0069245) filed Nov. 4, 2019, which is a Continuation of U.S. patent application Ser. No. 15/620,346, (issued as U.S. Pat. No. 10,463,295) filed Jun. 12, 2017, which claims the benefit of the filing date of U.S. Provisional Application No. 62/349,504, filed Jun. 13, 2016, the entire content of each of which is incorporated herein by reference.

TECHNICAL FIELD

The disclosure relates generally to medical device systems and, more particularly, medical device systems configured to monitor patient parameters, assess risks relevant to cardiac status, predict the impending occurrence of a cardiac event, and initiate measure(s) that prevents the cardiac event from occurring.

BACKGROUND

Implantable medical devices (IMDs) and external medical devices (e.g., wearable devices, insertable cardiac monitors, implantable pacemakers, or implantable cardioverter-defibrillators) may record cardiac electrogram (EGM) signals for sensing cardiac events such as P-waves and R-waves. IMDs may detect episodes of bradycardia, tachycardia, or fibrillation from the sensed cardiac events, and respond to the episodes as needed with pacing therapy or high-voltage anti-tachyarrhythmia shocks (e.g., cardioversion or defibrillation shocks). Some IMDs include, or are or part of a system that includes, sensors that generate other physiological signals, such as signals that vary based on patient movement or activity, cardiovascular pressure, blood oxygen saturation, edema, or thoracic impedance. Physiological parameters determined based on such signals may be used to assist in the detection of arrhythmia, as well as the detection or monitoring of other cardiac conditions, such as heart failure or infarction. Delivery of therapy in response to detection of a cardiac event, such as ventricular tachyarrhythmia, may negatively impact a patient's quality of life, while delayed treatment may present risk to the patient.

SUMMARY

In general, this disclosure is directed to systems and techniques for predicting the occurrence of an acute cardiac event, episode, or attack (referred to herein as "cardiac events"), such as a ventricular tachyarrhythmia episode, heart failure decompensation, or ischemia. The systems and techniques include determining a respective value for each of a plurality of parameters of a patient (e.g., physiological or pathophysiological) during each of a plurality of periods, which may be at least one hour, such as approximately one day. In some examples, processing circuitry of a medical device system indicates that the acute cardiac event is predicted if the cumulative degree of change across the physiological parameters during the current period is significantly greater than the variation in the physiological parameters during N recently preceding periods. In some examples, the processing circuitry may responsively provide an alert indicating that the acute cardiac event is predicted and/or deliver a therapy configured to prevent the predicted cardiac event.

In some examples, processing circuitry of a medical device system determines, for each of a plurality of patient parameters, a difference metric for a current period based on a value of a patient parameter determined for the current period and a value of the patient parameter determined for an immediately preceding period. In some examples, the processing circuitry determines a score for the current period based on a sum of the respective difference metrics for the plurality of patient parameters for the current period for at least some of the plurality of patient parameters. The processing circuitry determines a threshold for the current period based on scores determined for N periods that precede the current period, and compares the score for the current period to the threshold for the current period.

IMDs, such as implantable cardioverter-defibrillators (ICDs), are generally able to effectively detect and terminate tachyarrhythmias. However, even when properly detected and terminated, tachyarrhythmias and anti-tachyarrhythmia shocks may negatively impact a patient, and the shocks may negatively impact the longevity of the IMD. The techniques of this disclosure may avoid such negative impacts by enabling accurate prediction of tachyarrhythmia, and other acute cardiac events, prior to their occurrence. In some examples, the techniques of this disclosure may enable a medical device or clinician to provide a treatment to the patient that may prevent the occurrence of a predicted cardiac event. For example, a patient may receive a warning from implanted/wearable device and can consult with a clinician. In some examples, the medical device can automatically initiate a preventive measure targeting the predicted event in response to the prediction.

In an example, a medical device system comprises sensing circuitry configured to generate one or more physiological signals of a patient, and processing circuitry. For each of a plurality of periods, the processing circuitry is configured to determine a respective value for each of a plurality of patient parameters, wherein, for one or more of the plurality of patient parameters, the respective values are determined based on the one or more physiological signals generated during the period, for each of the plurality of patient parameters, determine a difference metric for a current period for each of the plurality of periods based on a value of the patient parameter determined for the current period and a value of the patient parameter determined for an immediately preceding period of the plurality periods, determine a score for the current period based on a sum of the difference metrics for the current period for the one or more of the plurality of patient parameters, determine a threshold for the current period based on scores determined for N periods of the plurality of periods that precede the current period, wherein N is an integer constant, compare the score for the current period to the threshold for the current period, and determine whether to generate an alert indicating that an acute cardiac event of the patient is predicted based on the comparison.

In another example, a method comprises generating, by sensing circuitry of a medical device system, one or more physiological signals of a patient. The method further comprises, for each of a plurality of periods, by processing circuitry of the medical device system, determining a respective value for each of a plurality of patient parameters, wherein, for one or more of the plurality of patient parameters, the respective values are determined based on the one or more physiological signals generated during the period, for each of the plurality of patient parameters, determining a difference metric for a current period for each of the plurality of periods based on a value of the patient parameter determined for the current period and a value of the patient parameter determined for an immediately preceding period of the plurality periods, determining a score for the current period based on a sum of the difference metrics for the current period for the one or more of the plurality of patient parameters, determining a threshold for the current period based on scores determined for N periods of the plurality of periods that precede the current period, wherein N is an integer constant, comparing the score for the current period to the threshold for the current period, and determining whether to generate an alert indicating that an acute cardiac event of the patient is predicted based on the comparison.

In another example, a medical device system comprises means for generating one or more physiological signals of a patient, and for each of a plurality of periods, means for determining a respective value for each of a plurality of patient parameters, wherein, for one or more of the plurality of patient parameters, the respective values are determined based on the one or more physiological signals generated during the period, for each of the plurality of patient parameters, means for determining a difference metric for a current period for each of the plurality of periods based on a value of the patient parameter determined for the current period and a value of the patient parameter determined for an immediately preceding period of the plurality periods, means for determining a score for the current period based on a sum of the difference metrics for the current period for the one or more of the plurality of patient parameters, means for determining a threshold for the current period based on scores determined for N periods of the plurality of periods that precede the current period, wherein N is an integer constant, means for comparing the score for the current period to the threshold for the current period, and means for determining whether to generate an alert indicating that an acute cardiac event of the patient is predicted based on the comparison.

In another example, a non-transitory computer-readable storage medium comprises instructions, that when executed by processing circuitry of a medical device system, cause the medical device system to receive one or more physiological signals of a patient, and for each of a plurality of periods, determine a respective value for each of a plurality of patient parameters, wherein, for one or more of the plurality of patient parameters, the respective values are determined based on the one or more physiological signals generated during the period, for each of the plurality of patient parameters, determine a difference metric for a current period for each of the plurality of periods based on a value of the patient parameter determined for the current period and a value of the patient parameter determined for an immediately preceding period of the plurality periods, determine a score for the current period based on a sum of the difference metrics for the current period for the one or more of the plurality of patient parameters, determine a threshold for the current period based on scores determined for N periods of the plurality of periods that precede the current period, wherein N is an integer constant, compare the score for the current period to the threshold for the current period, and determine whether to generate an alert indicating that an acute cardiac event of the patient is predicted based on the comparison.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF DRAWINGS

FIG. 12 is a tabular representation of another example technique for periodically determining a score based on respective difference metrics for each of a plurality of physiological parameters.

FIGS. 18-22 are tables of experimental results illustrating the performance of example techniques of this disclosure in predicting ventricular tachyarrhythmia.

FIG. 23 is a table illustrating a receiver operator characteristic for a coefficient used to determine a threshold for determining whether an acute cardiac event is predicted according to the example techniques of this disclosure.

DETAILED DESCRIPTION

In general, this disclosure describes example techniques related to predicting an acute occurrence of a cardiac event or attack (may be referred to herein as "acute cardiac event"), such as a ventricular tachyarrhythmia, heart failure decompensation, and ischemia, and responsively providing an alert indicating that the acute cardiac event is predicted, and/or deliver a therapy configured to prevent the predicted cardiac event. In the following description, references are made to illustrative examples. It is understood that other examples may be utilized without departing from the scope of the disclosure.

Figure 1:
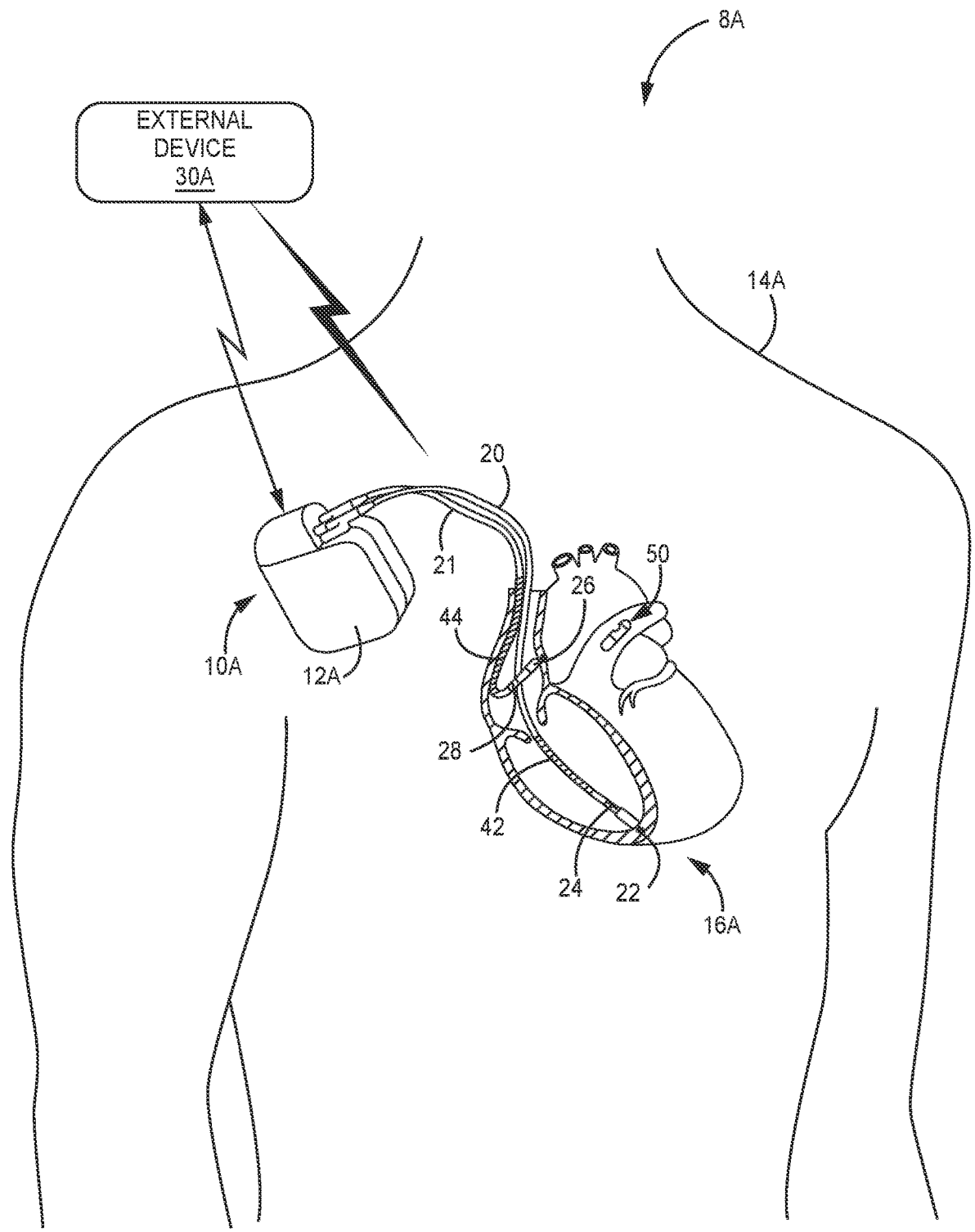
FIG. 1 is a conceptual drawing illustrating an example medical device system in conjunction with a patient.

FIG. 1 is a conceptual drawing illustrating an example medical device system 8A in conjunction with a patient 14A. Medical device system 8A is an example of a medical device system configured to implement the techniques described herein for predicting the acute occurrence of a cardiac event, such as a ventricular tachyarrhythmia, and responsively providing an alert indicating that the acute cardiac event is predicted, and/or delivering a therapy configured to prevent the predicted cardiac event. In the illustrated example, medical device system 8A includes an implantable medical device (IMD) 10A coupled to a ventricular lead 20 and an atrial lead 21. IMD 10A may be an ICD capable of delivering pacing, cardioversion and defibrillation therapy to the heart 16A of a patient 14A, and will be referred to as ICD 10A hereafter.

Ventricular lead 20 and atrial lead 21 are electrically coupled to ICD 10A and extend into the patient's heart 16A. Ventricular lead 20 includes electrodes 22 and 24 shown positioned on the lead in the patient's right ventricle (RV) for sensing ventricular EGM signals and pacing in the RV. Atrial lead 21 includes electrodes 26 and 28 positioned on the lead in the patient's right atrium (RA) for sensing atrial EGM signals and pacing in the RA.

Ventricular lead 20 additionally carries a high voltage coil electrode 42, and atrial lead 21 carries a high voltage coil electrode 44, used to deliver cardioversion and defibrillation shocks. The term "anti-tachyarrhythmia shock" may be used herein to refer to both cardioversion shocks and defibrillation shocks. In other examples, ventricular lead 20 may carry both of high voltage coil electrodes 42 and 44, or may carry a high voltage coil electrode in addition to those illustrated in the example of FIG. 1.

ICD 10A may use both ventricular lead 20 and atrial lead 21 to acquire cardiac electrogram (EGM) signals from patient 14A and to deliver therapy in response to the acquired data. Medical device system 8A is shown as having a dual chamber ICD configuration, but other examples may include one or more additional leads, such as a coronary sinus lead extending into the right atrium, through the coronary sinus and into a cardiac vein to position electrodes along the left ventricle (LV) for sensing LV EGM signals and delivering pacing pulses to the LV. In other examples, a medical device system may be a single chamber system, or otherwise not include atrial lead 21.

Processing circuitry, sensing circuitry, and other circuitry configured for performing the techniques described herein are housed within a sealed housing 12. Housing 12 (or a portion thereof) may be conductive so as to serve as an electrode for pacing or sensing or as an active electrode during defibrillation. As such, housing 12 is also referred to herein as "housing electrode" 12.

ICD 10A may transmit EGM signal data and cardiac rhythm episode data acquired by ICD 10A, as well as data regarding delivery of therapy by ICD 10A, to an external device 30A. External device 30A may be a computing device that may be used in a home, ambulatory setting, clinic, or hospital setting, to communicate with ICD 10A via wireless telemetry. External device 30A may be coupled to a remote patient monitoring system, such as Carelink®, available from Medtronic plc, of Dublin, Ireland. External device 30A may be, as examples, a programmer, external monitor, or consumer device, e.g., smart phone.

External device 30A may be used to program commands or operating parameters into ICD 10A for controlling its functioning, e.g., when configured as a programmer for ICD 10A. External device 30A may be used to interrogate ICD 10A to retrieve data, including device operational data as well as physiological data accumulated in IMD memory. The interrogation may be automatic, e.g., according to a schedule, or in response to a remote or local user command. Programmers, external monitors, and consumer devices are examples of external devices 30A that may be used to interrogate ICD 10A. Examples of communication techniques used by ICD 10A and external device 30A include radiofrequency (RF) telemetry, which may be an RF link established via Bluetooth, WiFi, or medical implant communication service (MICS).

In some examples, as illustrated in FIG. 1, medical device system 8A may also include a pressure-sensing IMD 50. In the illustrated example, pressure-sensing IMD 50 is implanted in the pulmonary artery of patient 14A. In some examples, one or more pressure-sensing IMDs 50 may additionally or alternatively be implanted within a chamber of heart 16A, or generally at other locations in the circulatory system.

In one example, pressure-sensing IMD 50 is configured to sense blood pressure of patient 14A. For example, pressure-sensing IMD 50 may be arranged in the pulmonary artery and be configured to sense the pressure of blood flowing from the right ventricle outflow tract (RVOT) from the right ventricle through the pulmonary valve to the pulmonary artery. Pressure-sensing IMD 50 may therefore directly measure the pulmonary artery diastolic pressure (PAD) of patient 14A. The PAD value is a pressure value that can be employed in patient monitoring. For example, PAD may be used as a basis for evaluating congestive heart failure in a patient.

In other examples, however, pressure-sensing IMD 50 may be employed to measure blood pressure values other than PAD. For example, pressure-sensing IMD 50 may be arranged in right ventricle 28 of heart 14 to sense RV systolic or diastolic pressure, or may sense systolic or diastolic pressures at other locations of the cardiovascular system, such as within the pulmonary artery. As shown in FIG. 1, pressure-sensing IMD 50 is positioned in the main trunk of pulmonary artery 39. In other examples, a sensor, such as pressure-sensing IMD 50 may be either positioned in the right or left pulmonary artery beyond the bifurcation of the pulmonary artery.

Moreover, the placement of pressure-sensing IMD 50 is not restricted necessarily to the pulmonary side of the circulation. Pressure-sensing IMD 50 could potentially be placed in the systemic side of the circulation. For example, under certain conditions and with appropriate safety measures, pressure-sensing IMD 50 could even be placed in the left atrium, left ventricle, or aorta. Additionally, pressure-sensing IMD 50 is not restricted to placement within the cardiovascular system. For example, the pressure-sensing IMD 50 might be placed in the renal circulation. Placement of pressure-sensing IMD 50 in the renal circulation may be beneficial, for example, to monitor the degree of renal insufficiency in the patient based on the monitoring of pressure or some other indication of renal circulation by pressure-sensing IMD 50.

In some examples, pressure-sensing IMD 50 includes a pressure sensor configured to respond to the absolute pressure inside the pulmonary artery of patient 14A. Pressure-sensing IMD 50 may be, in such examples, any of a number of different types of pressure sensors. One form of pressure sensor that may be useful for measuring blood pressure is a capacitive pressure sensor. Another example pressure sensor is an inductive sensor. In some examples, pressure-sensing IMD 50 may also comprise a piezoelectric or piezoresistive pressure transducer. In some examples, pressure-sensing IMD 50 may comprise a flow sensor.

In one example, pressure-sensing IMD 50 comprises a leadless pressure sensor including capacitive pressure sensing elements configured to measure blood pressure within the pulmonary artery. Pressure-sensing IMD 50 may be in wireless communication with ICD 10A and/or external device 30A, e.g., in order to transmit blood pressure measurements to one or both of the devices. Pressure-sensing IMD 50 may employ, e.g., radio frequency (RF) or other telemetry techniques for communicating with ICD 10A and other devices, including, e.g., external device 30A. In another example, pressure-sensing IMD 50 may include a tissue conductance communication (TCC) system by which the device employs tissue of patient 14A as an electrical communication medium over which to send and receive information to and from ICD 10A and/or external device 30A.

Medical device system 8A is an example of a medical device system configured to determine whether an acute occurrence of a cardiac event, such as a ventricular tachyarrhythmia, is predicted to occur, and to responsively provide an alert indicating that the acute cardiac event is predicted, and/or deliver a therapy configured to prevent the predicted cardiac event. The techniques may be performed by processing circuitry of medical device system 8A, such as processing circuitry of one or both of ICD 10A and external device 30A, individually, or collectively.

The techniques include determining a respective value for each of a plurality of parameters of a patient, e.g., physiological and/or pathophysiological, during each of a plurality of periods, which may be at least one hour, such as between approximately one day and approximately three days, e.g., in one example, approximately one day. The processing circuitry may determine the values of at least some the patient parameters based on physiological signals generated by sensing circuitry of one or both of ICD 10A and pressure-sensing IMD 50, such as a cardiac EGM signal generated by sensing circuitry of ICD 10A, or a pulmonary artery or other cardiovascular pressure signal generated by pressure-sensing IMD 50. In some examples, one or both of ICD 10A and pressure-sensing IMD 50 may include or be coupled to one or more other sensors that generate one or more other physiological signals, such as signals that vary based on patient motion and/or posture, blood flow, respiration, or edema. The processing circuitry may determine other patient parameters based on therapy delivered by ICD 10A, such as patient parameters indicating the extent to which patient 14A is dependent on pacing, e.g., a percentage of time or other characterization of amount of pacing delivered to the patient.

In some examples, the processing circuitry of medical device system 8A indicates that the acute cardiac event is predicted if the cumulative degree of change across the patient parameters during the current period is significantly greater than the variation in the patient parameters during N recently preceding periods. For example, as will be described in greater detail below, the processing circuitry may determine, for each of a plurality of patient parameters, a difference metric for a current period based on a value of a patient parameter determined for the current period and a value of the patient parameter determined for an immediately preceding period. In some examples, the processing circuitry determines a score for the current period based on a sum of the difference metrics for the current period for at least some of the plurality of patient parameters. The processing circuitry determines a threshold for the current period based on scores determined for N periods that precede the current period, and compares the score for the current period to the threshold for the current period to determine whether the acute event is predicted. If the processing circuitry determines that the acute cardiac event is predicted, the processing circuitry may generate an alert and, in some examples, control delivery of one or more preventative measures configured to prevent the event, such as cardiac pacing, neuromodulation, or one or more therapeutic substances, e.g., drugs.

Medical device system 8A is one example of a medical device system that may be configured to implement the techniques described herein for determining whether an acute cardiac event is predicted. Other example medical device systems that may be configured to implement the techniques are described with respect to FIGS. 2-6. Although described herein primarily in the context of implantable medical devices generating physiological signals and, in some examples, delivering therapy, a medical device system that implements the techniques described in this disclosure may additionally or alternatively include an external medical device, e.g., external cardiac monitor, and/or external pacemaker, cardioverter and/or defibrillator, configured to generate one or more of the physiological signals described herein, determine whether an acute cardiac event is predicted, provide an alert, and/or deliver one or more of the preventative therapies described herein.

Figure 2:
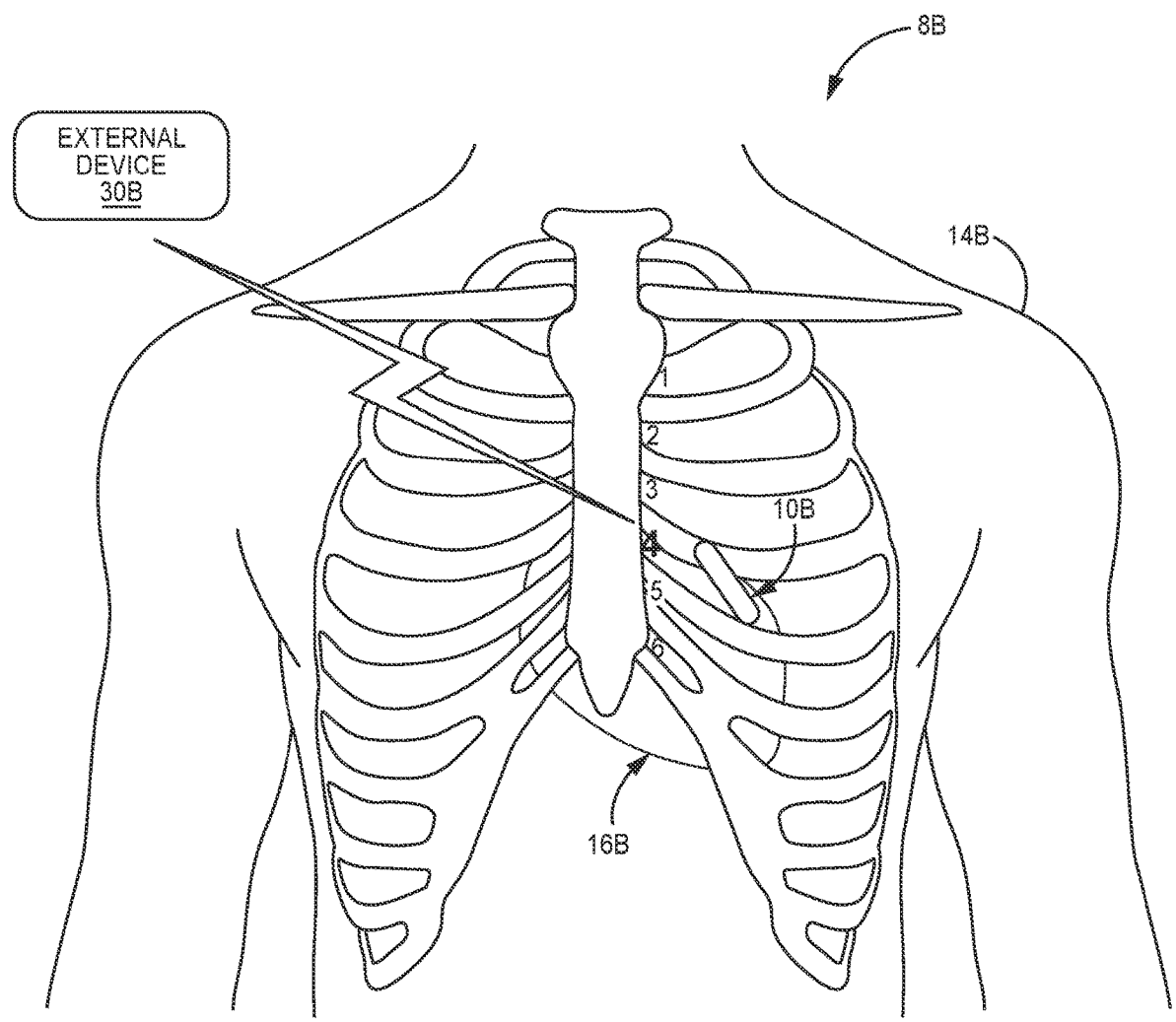
FIG. 2 is a conceptual drawing illustrating another example medical device system in conjunction with a patient.

FIG. 2 is a conceptual drawing illustrating another example medical device system 8B in conjunction with a patient 14B. Medical device system 8B is another example of a medical device system configured to implement the techniques described herein for predicting the acute occurrence of a cardiac event, such as a ventricular tachyarrhythmia, and responsively providing an alert indicating that the acute cardiac event is predicted. In the illustrated example, medical device system 8B includes an IMD 10B and an external device 30B.

IMD 10B is an insertable cardiac monitor (ICM) capable of sensing and recording cardiac EGM signals from a position outside of heart 16B, and will be referred to as ICM 10B hereafter. In some examples, ICM 10B includes or is coupled to one or more additional sensors that generate one or more other physiological signals, such as signals that vary based on patient motion and/or posture, blood flow, or respiration. ICM 10B may be implanted outside of the thorax of patient 14B, e.g., subcutaneously or submuscularly, such as the pectoral location illustrated in FIG. 2. In some examples, ICM 10B may take the form of a Reveal LINQ™ ICM, available from Medtronic plc, of Dublin, Ireland.

External device 30B may be configured in a manner substantially similar to that described above with respect to external device 30A and FIG. 1. External device 30B may wirelessly communicate with ICM 10B, e.g., to program the functionality of the ICM, and to retrieve recorded physiological signals and/or patient parameter values or other data derived from such signals from the ICM. Both ICM 10B and external device 30B include processing circuitry, and the processing circuitry of either or both device may perform the techniques described herein, such as determining patient parameter values for a period, determining difference metrics based on the patient parameter values, determining a score for the period based on the difference metrics, and comparing the score to a determined threshold.

Based on the comparison, the processing circuitry may also be configured to provide an alert to a user, e.g., clinician or patient 14B, that the acute cardiac event is predicted, e.g., via external device 30B. Although ICM 10B is not described as being configured to deliver therapy, patient 14B, a clinician, or another implanted or external medical device may deliver or take a preventative measure to prevent the acute cardiac event predicted by medical device system 8B. Ventricular tachyarrhythmia is one example of an acute cardiac event that may be predicted according to the techniques of this disclosure. Other example acute cardiac events include heart failure decompensation and myocardial infarction.

Although not illustrated in the example of FIG. 2, a medical device system configured to implement the techniques of this disclosure may include one or more implanted or external medical devices in addition to or instead of ICM 10B. For example, a medical device system may include a pressure sensing IMD 50, vascular ICD (e.g., ICD 10A of FIG. 1), extravascular ICD (e.g., ICD 10C of FIGS. 4A-5), or cardiac pacemaker (e.g., IPD 10D of FIGS. 4A-6 or a cardiac pacemaker implanted outside the heart but coupled to intracardiac or epicardial leads). One or more such devices may generate physiological signals, and include processing circuitry configured to perform, in whole or in part, the techniques described herein for predicting an acute cardiac event. The implanted devices may communicate with each other and/or an external device 30, and one of the implanted or external devices may ultimately determine whether the acute cardiac event is predicted based on information received from the other device(s).

Figure 3:
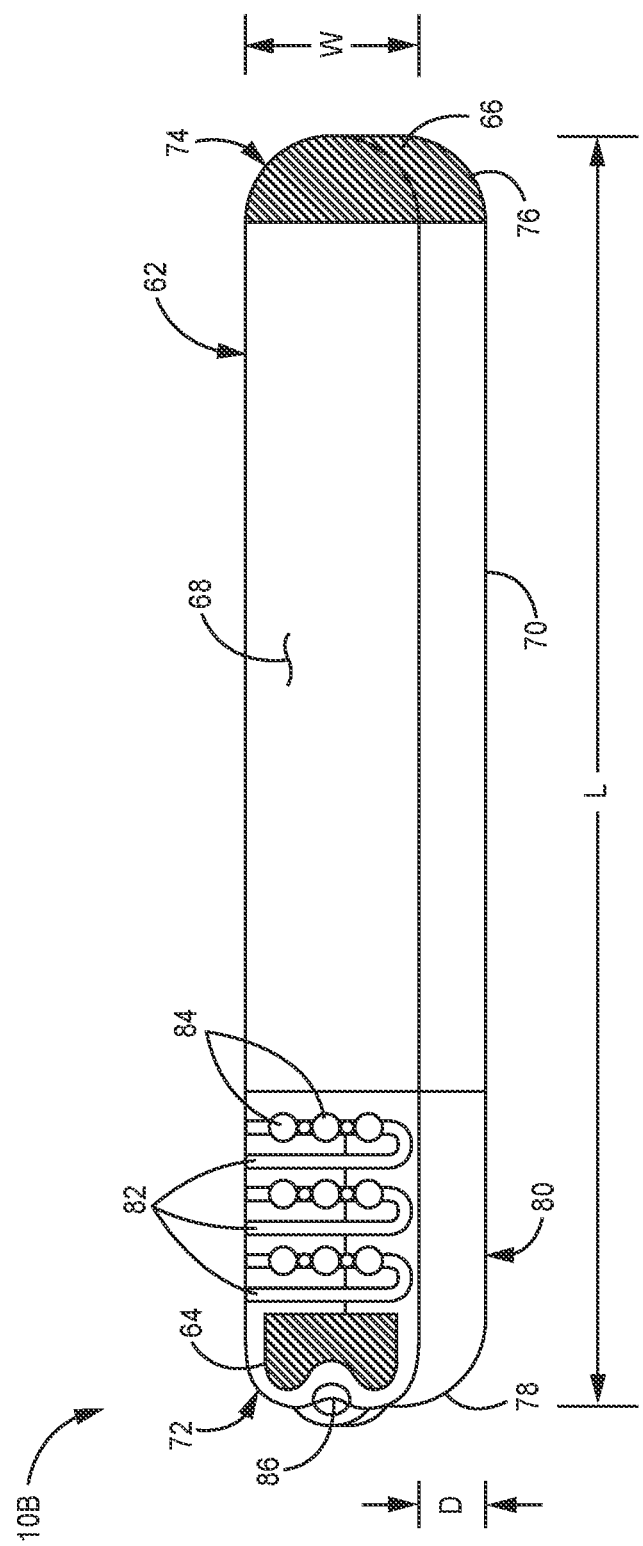
FIG. 3 is a perspective drawing illustrating an example configuration of the implantable cardiac monitor of FIG. 2.

FIG. 3 is a conceptual drawing illustrating an example configuration of ICM 10B. In the example shown in FIG. 4, ICM 300 may be embodied as a monitoring device having housing 62, proximal electrode 64 and distal electrode 66. Housing 62 may further comprise first major surface 68, second major surface 70, proximal end 72, and distal end 74. Housing 62 encloses electronic circuitry located inside the ICM 10B and protects the circuitry contained therein from body fluids. Electrical feedthroughs provide electrical connection of electrodes 64 and 66.

In the example shown in FIG. 3, ICM 10B is defined by a length L, a width W and thickness or depth D and is in the form of an elongated rectangular prism wherein the length L is much larger than the width W, which in turn is larger than the depth D. In one example, the geometry of the ICM 10B—in particular a width W greater than the depth D—is selected to allow ICM 10B to be inserted under the skin of the patient using a minimally invasive procedure and to remain in the desired orientation during insertion. For example, the device shown in FIG. 3 includes radial asymmetries (notably, the rectangular shape) along the longitudinal axis that maintains the device in the proper orientation following insertion. For example, in one example the spacing between proximal electrode 64 and distal electrode 66 may range from 30 millimeters (mm) to 55 mm, 35 mm to 55 mm, and from 40 mm to 55 mm and may be any range or individual spacing from 25 mm to 60 mm. In addition, ICM 10B may have a length L that ranges from 30 mm to about 70 mm. In other examples, the length L may range from 40 mm to 60 mm, 45 mm to 60 mm and may be any length or range of lengths between about 30 mm and about 70 mm. In addition, the width W of major surface 68 may range from 3 mm to 10 mm and may be any single or range of widths between 3 mm and 10 mm. The thickness of depth D of ICM 10B may range from 2 mm to 9 mm. In other examples, the depth D of ICM 10B may range from 2 mm to 5 mm and may be any single or range of depths from 2 mm to 9 mm. In addition, ICM 10B according to an example of the present disclosure is has a geometry and size designed for ease of implant and patient comfort. Examples of ICM 10B described in this disclosure may have a volume of three cubic centimeters (cm) or less, 1.5 cubic cm or less or any volume between three and 1.5 cubic centimeters.

In the example shown in FIG. 3, once inserted within the patient, the first major surface 68 faces outward, toward the skin of the patient while the second major surface 70 is located opposite the first major surface 68. In addition, in the example shown in FIG. 3, proximal end 72 and distal end 74 are rounded to reduce discomfort and irritation to surrounding tissue once inserted under the skin of the patient. ICM 10B, including instrument and method for inserting ICM 10B is described, for example, in U.S. Patent Publication No. 2014/0276928, incorporated herein by reference in its entirety.

Proximal electrode 64 and distal electrode 66 are used to sense cardiac signals, e.g. ECG signals, intra-thoracically or extra-thoracically, which may be sub-muscularly or subcutaneously. ECG signals may be stored in a memory of the ICM 10B, and ECG data may be transmitted via integrated antenna 82 to another medical device, which may be another implantable device or an external device, such as external device 30B. In some example, electrodes 64 and 66 may additionally or alternatively be used for sensing any biopotential signal of interest, which may be, for example, an EGM, EEG, EMG, or a nerve signal, from any implanted location.

In the example shown in FIG. 3, proximal electrode 64 is in close proximity to the proximal end 72 and distal electrode 66 is in close proximity to distal end 74. In this example, distal electrode 66 is not limited to a flattened, outward facing surface, but may extend from first major surface 68 around rounded edges 76 and/or end surface 78 and onto the second major surface 70 so that the electrode 66 has a three-dimensional curved configuration. In the example shown in FIG. 3, proximal electrode 64 is located on first major surface 68 and is substantially flat, outward facing. However, in other examples proximal electrode 64 may utilize the three dimensional curved configuration of distal electrode 66, providing a three dimensional proximal electrode (not shown in this example). Similarly, in other examples distal electrode 66 may utilize a substantially flat, outward facing electrode located on first major surface 68 similar to that shown with respect to proximal electrode 64. The various electrode configurations allow for configurations in which proximal electrode 64 and distal electrode 66 are located on both first major surface 68 and second major surface 70. In other configurations, such as that shown in FIG. 3, only one of proximal electrode 64 and distal electrode 66 is located on both major surfaces 68 and 70, and in still other configurations both proximal electrode 64 and distal electrode 66 are located on one of the first major surface 68 or the second major surface 70 (i.e., proximal electrode 64 located on first major surface 68 while distal electrode 66 is located on second major surface 70). In another example, ICM 10B may include electrodes on both major surface 68 and 70 at or near the proximal and distal ends of the device, such that a total of four electrodes are included on ICM 10B. Electrodes 64 and 66 may be formed of a plurality of different types of biocompatible conductive material, e.g. stainless steel, titanium, platinum, iridium, or alloys thereof, and may utilize one or more coatings such as titanium nitride or fractal titanium nitride.

In the example shown in FIG. 3, proximal end 72 includes a header assembly 80 that includes one or more of proximal electrode 64, integrated antenna 82, anti-migration projections 84, and/or suture hole 86. Integrated antenna 82 is located on the same major surface (i.e., first major surface 68) as proximal electrode 64 and is also included as part of header assembly 80. Integrated antenna 82 allows ICM 10B to transmit and/or receive data. In other examples, integrated antenna 82 may be formed on the opposite major surface as proximal electrode 64, or may be incorporated within the housing 82 of ICM 10B. In the example shown in FIG. 3, anti-migration projections 84 are located adjacent to integrated antenna 82 and protrude away from first major surface 68 to prevent longitudinal movement of the device. In the example shown in FIG. 3, anti-migration projections 84 includes a plurality (e.g., nine) small bumps or protrusions extending away from first major surface 68. As discussed above, in other examples anti-migration projections 84 may be located on the opposite major surface as proximal electrode 64 and/or integrated antenna 82. In addition, in the example shown in FIG. 3 header assembly 80 includes suture hole 86, which provides another means of securing ICM 10B to the patient to prevent movement following insert. In the example shown, suture hole 86 is located adjacent to proximal electrode 64. In one example, header assembly 80 is a molded header assembly made from a polymeric or plastic material, which may be integrated or separable from the main portion of ICM 10B.

Figure 4A:
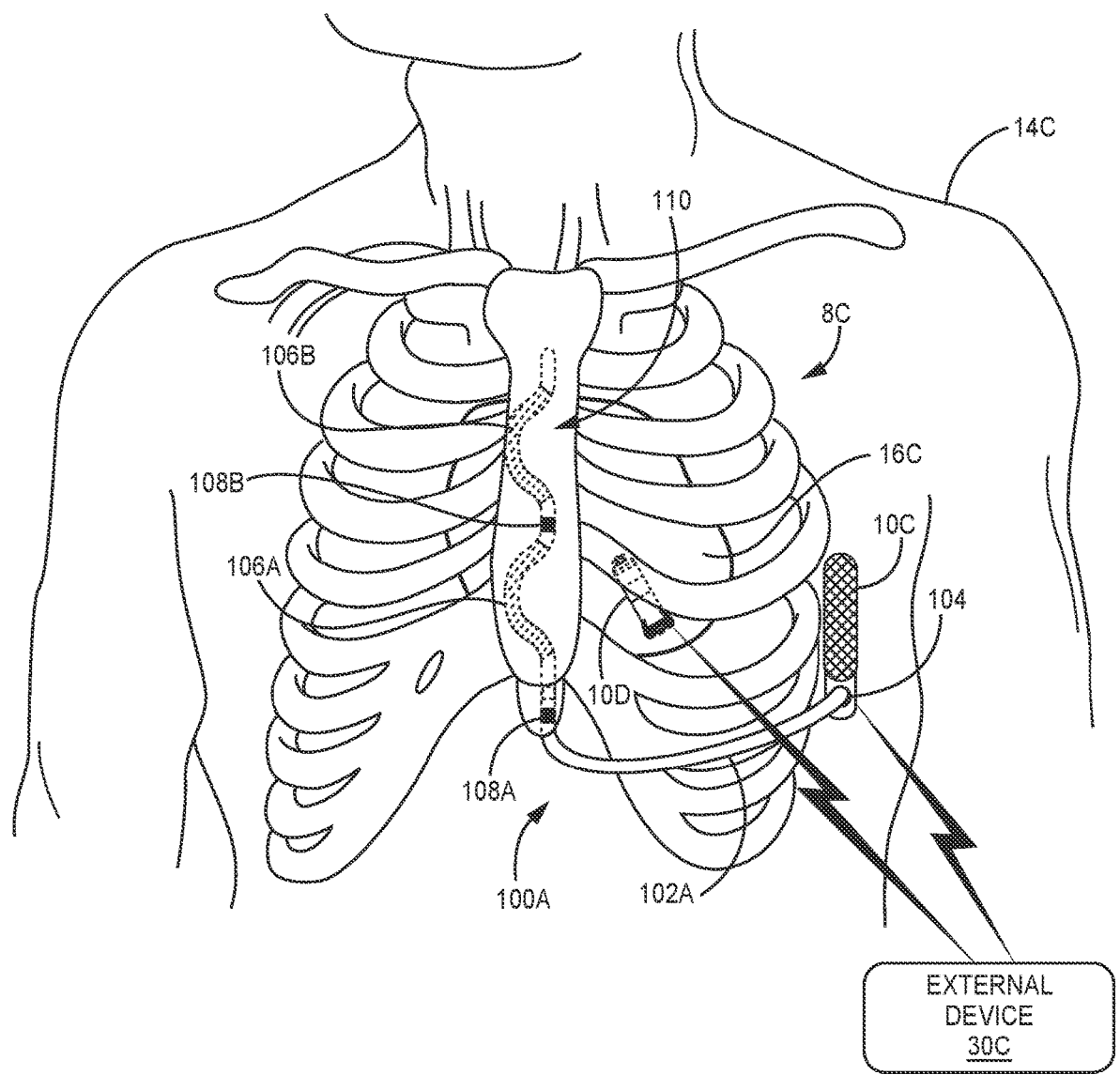
FIGS. 4A-4C are a front-view, side-view, and top-view conceptual drawings, respectively, illustrating another example medical device system in conjunction with a patient.
Figure 4B:
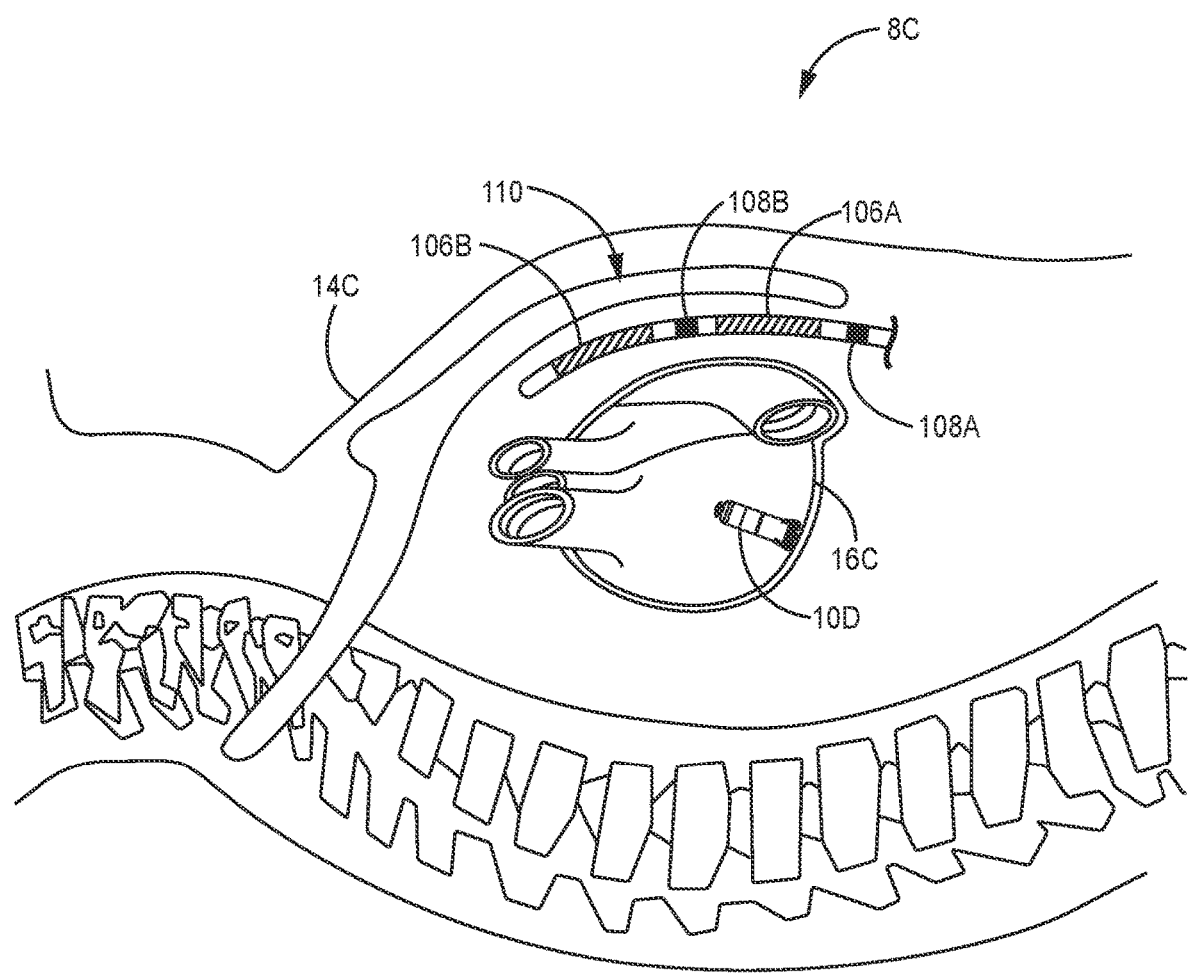
Figure 4C:
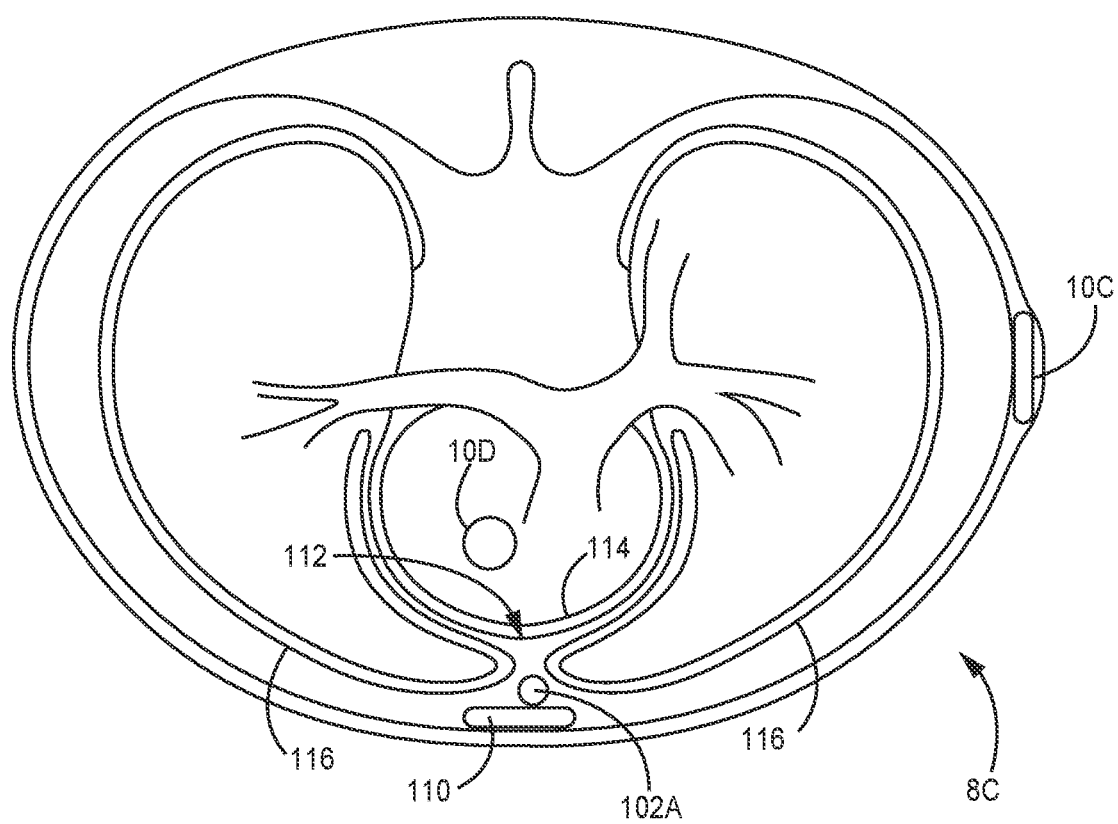

FIGS. 4A-4C are front-view, side-view, and top-view conceptual drawings, respectively, illustrating another example medical device system 8C in conjunction with a patient 14C. Medical device system 8C is another example of a medical device system configured to implement the techniques described herein for predicting the acute occurrence of a cardiac event, such as a ventricular tachyarrhythmia, and responsively providing an alert indicating that the acute cardiac event is predicted.

In the illustrated example, medical device system 8C includes an extracardiovascular ICD system 100A implanted within a patient 14C. ICD system 100A includes an IMD 10C, which is an ICD and is referred to hereafter as ICD 10C, connected to at least one implantable cardiac defibrillation lead 102A. ICD 10C is configured to deliver high-energy cardioversion or defibrillation pulses to a patient's heart 16C when atrial or ventricular fibrillation is detected. Cardioversion shocks are typically delivered in synchrony with a detected R-wave when fibrillation detection criteria are met. Defibrillation shocks are typically delivered when fibrillation criteria are met, and the R-wave cannot be discerned from signals sensed by ICD 10C.

ICD 10C is implanted subcutaneously or submuscularly on the left side of patient 14C above the ribcage. Defibrillation lead 102A may be implanted at least partially in a substernal location, e.g., between the ribcage and/or sternum 110 and heart 16C. In one such configuration, a proximal portion of lead 102A extends subcutaneously from ICD 10C toward sternum 110 and a distal portion of lead 102A extends superior under or below the sternum 110 in the anterior mediastinum 112 (FIG. 4C). The anterior mediastinum 112 is bounded laterally by the pleurae 116 (FIG. 1C), posteriorly by the pericardium 114 (FIG. 4C), and anteriorly by the sternum 110. In some instances, the anterior wall of the anterior mediastinum may also be formed by the transversus thoracis and one or more costal cartilages. The anterior mediastinum includes a quantity of loose connective tissue (such as areolar tissue), some lymph vessels, lymph glands, sub sternal musculature (e.g., transverse thoracic muscle), branches of the internal thoracic artery, and the internal thoracic vein. In one example, the distal portion of lead 102A extends along the posterior side of the sternum 110 substantially within the loose connective tissue and/or substernal musculature of the anterior mediastinum. Lead 102A may be at least partially implanted in other intrathoracic locations, e.g., other non-vascular, extra-pericardial locations, including the gap, tissue, or other anatomical features around the perimeter of and adjacent to, but not attached to, the pericardium or other portion of the heart and not above the sternum 110 or ribcage.

In other examples, lead 102A may be implanted at other extracardiovascular locations. For example, defibrillation lead 102A may extend subcutaneously above the ribcage from ICD 10C toward a center of the torso of patient 14C, bend or turn near the center of the torso, and extend subcutaneously superior above the ribcage and/or sternum 110. Defibrillation lead 102A may be offset laterally to the left or the right of the sternum 110 or located over the sternum 110. Defibrillation lead 102A may extend substantially parallel to the sternum 110 or be angled lateral from the sternum 110 at either the proximal or distal end.

Defibrillation lead 102A includes an insulative lead body having a proximal end that includes a connector 104 configured to be connected to ICD 10C and a distal portion that includes one or more electrodes. Defibrillation lead 102A also includes one or more conductors that form an electrically conductive path within the lead body and interconnect the electrical connector and respective ones of the electrodes.

Defibrillation lead 102A includes a defibrillation electrode that includes two sections or segments 106A and 106B, collectively (or alternatively) defibrillation electrode 106. The defibrillation electrode 106 is toward the distal portion of defibrillation lead 102A, e.g., toward the portion of defibrillation lead 102A extending along the sternum 110. Defibrillation lead 102A is placed below and/or along sternum 110 such that a therapy vector between defibrillation electrodes 106A or 106B and a housing electrode formed by or on ICD 10C (or other second electrode of the therapy vector) is substantially across a ventricle of heart 16C. The therapy vector may, in one example, be viewed as a line that extends from a point on defibrillation electrode 106 (e.g., a center of one of the defibrillation electrode sections 106A or 106B) to a point on the housing electrode of ICD 10C. Defibrillation electrode 106 may, in one example, be an elongated coil electrode.

Defibrillation lead 102A may also include one or more sensing electrodes, such as sensing electrodes 108A and 108B (individually or collectively, "sensing electrode(s)

108"), located along the distal portion of defibrillation lead 102A. In the example illustrated in FIG. 4A and FIG. 4B, sensing electrodes 108A and 108B are separated from one another by defibrillation electrode 106A. In other examples, however, sensing electrodes 108A and 108B may be both distal of defibrillation electrode 106 or both proximal of defibrillation electrode 106. In other examples, lead 102A may include more or fewer electrodes at various locations proximal and/or distal to defibrillation electrode 106. In the same or different examples, ICD 10C may include one or more electrodes on another lead (not shown).

ICD system 100A may sense electrical signals via one or more sensing vectors that include combinations of electrodes 108A and 108B and the housing electrode of ICD 10C. In some instances, ICD 10C may sense cardiac electrical signals using a sensing vector that includes one of the defibrillation electrode sections 106A and 106B and one of sensing electrodes 108A and 108B or the housing electrode of ICD 9. The sensed electrical intrinsic signals may include electrical signals generated by cardiac muscle and indicative of depolarizations and repolarizations of heart 16C at various times during the cardiac cycle. ICD 10C analyzes the electrical signals sensed by the one or more sensing vectors to detect tachyarrhythmia, such as ventricular tachycardia or ventricular fibrillation. In response to detecting the tachyarrhythmia, ICD 10C may begin to charge a storage element, such as a bank of one or more capacitors, and, when charged, deliver one or more defibrillation pulses via defibrillation electrode 106 of defibrillation lead 102A if the tachyarrhythmia is still present.

Medical device system 8C also includes an IMD 10D, which is implanted within heart 16C and configured to deliver cardiac pacing to the heart, e.g., is an intracardiac pacing device (IPD). IMD 10D is referred to as IPD 10D hereafter. In the illustrated example, IPD 10D is implanted within the right ventricle of heart 16C. However, in other examples, system 8C may additionally or alternatively include one or more IPDs 10D within other chambers of heart 16C, or similarly configured pacing devices attached to an external surface of heart 16C (e.g., in contact with the epicardium) such that the pacing device is disposed outside of heart 16C.

IPD 10D is configured to sense electrical activity of heart 16C and deliver pacing therapy, e.g., bradycardia pacing therapy, cardiac resynchronization therapy (CRT), anti-tachycardia pacing (ATP) therapy, and/or post-shock pacing, to heart 16C. IPD 10D may be attached to an interior wall of heart 16C via one or more fixation elements that penetrate the tissue. These fixation elements may secure IPD 10D to the cardiac tissue and retain an electrode (e.g., a cathode or an anode) in contact with the cardiac tissue.

IPD 10D may be capable sensing electrical signals using the electrodes carried on the housing of IPD 10D. These electrical signals may be electrical signals generated by cardiac muscle and indicative of depolarizations and repolarizations of heart 16C at various times during the cardiac cycle. IPD 10D may analyze the sensed electrical signals to detect bradycardia and tachyarrhythmias, such as ventricular tachycardia or ventricular fibrillation. In response to detecting bradycardia, IPD 10D may deliver bradycardia pacing via the electrodes of IPD 10D. In response to detecting tachyarrhythmia, IPD 10D may, e.g., depending on the type of tachyarrhythmia, deliver ATP therapy via the electrodes of IPD 10D. In some examples, IPD 10D may deliver post-shock pacing in response to determining that another medical device, e.g., ICD 10C, delivered an anti-tachyarrhythmia shock.

IPD 10D and ICD 10C may be configured to coordinate their arrhythmia detection and treatment activities. In some examples IPD 10D and ICD 10C may be configured to operate completely independently of one another. In such a case, IPD 10D and ICD 10C are not capable of establishing telemetry communication sessions with one another to exchange information about sensing and/or therapy using one-way or two-way communication. Instead, each of IPD 10D and ICD 10C analyze the data sensed via their respective electrodes to make tachyarrhythmia detection and/or therapy decisions. As such, each device does not know if the other will detect the tachyarrhythmia, if or when it will provide therapy, and the like. In some examples, IPD 10D may be configured to detect anti-tachyarrhythmia shocks delivered by ICD system 100A, which may improve the coordination of therapy between subcutaneous ICD 10C and IPD 10D without requiring device-to-device communication. In this manner, IPD 10D may coordinate the delivery of cardiac stimulation therapy, including the termination of ATP and the initiation of the delivery of post-shock pacing, with the application of an anti-tachyarrhythmia shock merely through the detection of defibrillation pulses and without the need to communicate with the defibrillation device applying the anti-tachyarrhythmia shock.

In other examples, IPD 10D and ICD 10C may engage in communication to facilitate the appropriate detection of arrhythmias and/or delivery of therapy. The communication may include one-way communication in which one device is configured to transmit communication messages and the other device is configured to receive those messages. The communication may instead include two-way communication in which each device is configured to transmit and receive communication messages. Two-way communication and coordination of the delivery of patient therapies between IPD 10D and ICD 10C is described in commonly-assigned U.S. Pat. No. 8,744,572, titled, "SYSTEMS AND METHODS FOR LEADLESS PACING AND SHOCK THERAPY," issued Jun. 3, 2014, the entire content of which is incorporated by reference herein.

External device 30C may be configured substantially similarly to external device 30A described above with respect to FIG. 1. External device 30C may be configured to communicate with one or both of ICD 10C and IPD 10D. In examples where external device 30C only communicates with one of ICD 10C and IPD 10D, the non-communicative device may receive instructions from or transmit data to the device in communication with external device 30C. In some examples, a user may interact with device 30C remotely via a networked computing device. The user may interact with external device 30C to communicate with IPD 10D and/or ICD 10C.

For example, the user may interact with external device 30C to send an interrogation request and retrieve sensed physiological data or therapy delivery data stored by one or both of ICD 10C and IPD 10D, and program or update therapy parameters that define therapy, or perform any other activities with respect to ICD 10C and IPD 10D. Although the user is a physician, technician, surgeon, electrophysiologist, or other healthcare professional, the user may be patient 14C in some examples. For example, external device 21 may allow a user to program any coefficients, weighting factors, or techniques for determining difference metrics, scores, and/or thresholds, or other data described herein as being used by a medical device system to determine whether an acute cardiac event is predicted.

Although FIGS. 4A-4C are shown or described in the context of IPD 10D and extracardiovascular ICD system 100A that includes lead 102A with a substernally placed distal portion, techniques in accordance with one or more aspects of the present disclosure may be applicable to other coexistent systems. For example, an extracardiovascular ICD system may include a lead having a distal portion that is implanted subcutaneously above the sternum (or other location) instead of being implanted substernally. As another example, instead of an IPD, a pacing system may be implanted having a pacemaker and one or more leads connected to and extending from the pacemaker into one or more chambers of the heart or attached to the outside of the heart to provide pacing therapy to the one or more chambers. As such, the example of FIGS. 4A-4C is illustrated for example purposes only and should not be considered limiting of the techniques described herein.

Figure 5:
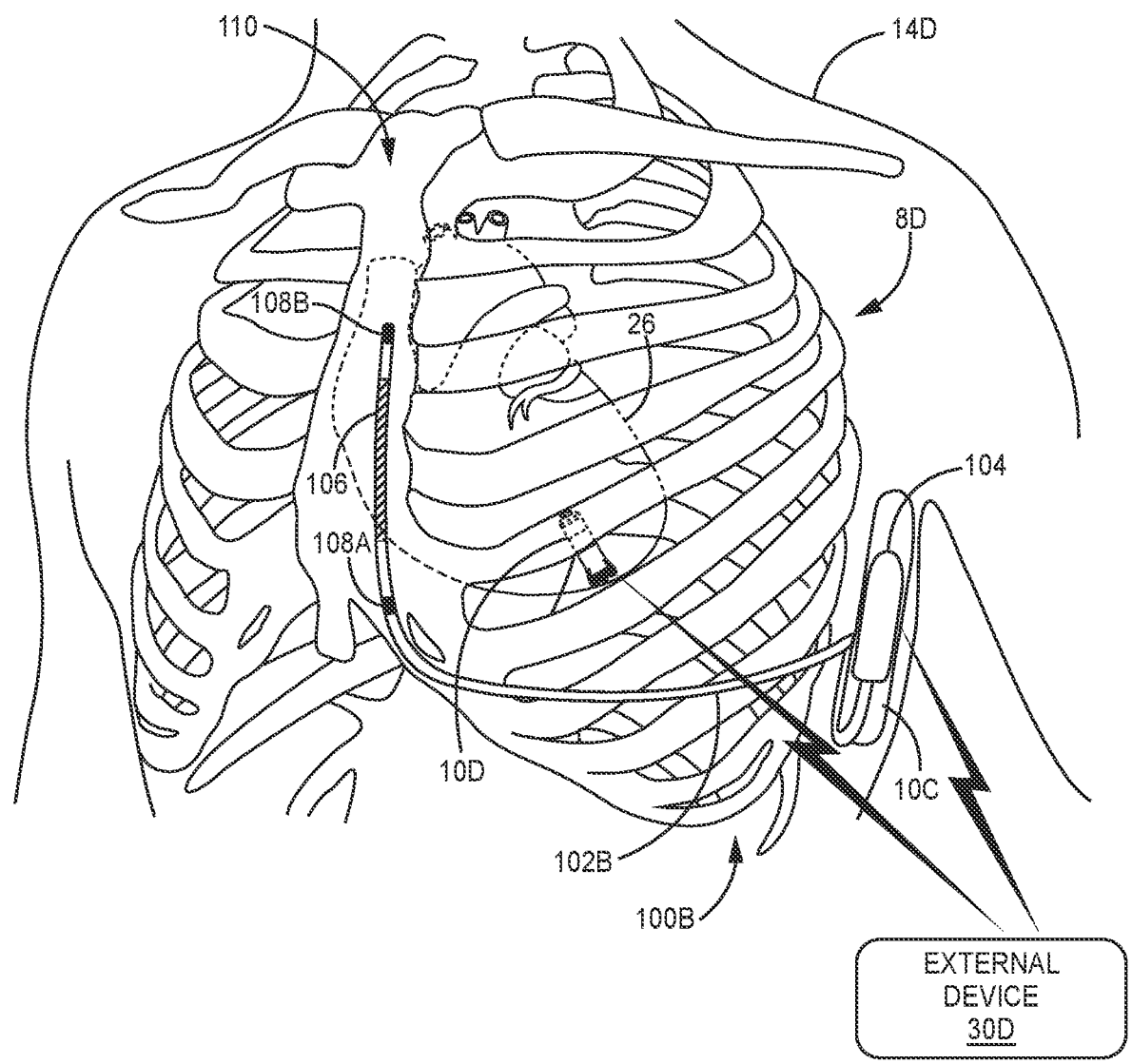
FIG. 5 is a conceptual drawing illustrating another example medical device system in conjunction with a patient.

FIG. 5 is a conceptual drawing illustrating another example medical device system 8D that includes an extracardiovascular ICD system 100B and IPD 10D implanted within a patient. Medical device system 8B may be configured to perform any of the techniques described herein with respect to medical device system 8C of FIGS. 4A-4C. Components with like numbers in FIGS. 4A-4C and FIG. 5 may be similarly configured and provide similar functionality.

In the example of FIG. 5, extracardiovascular ICD system 100B includes ICD 10C coupled to a defibrillation lead 102B. Unlike defibrillation lead 102A of FIGS. 4A-4C, defibrillation lead 102B extends subcutaneously above the ribcage from ICD 10C. In the illustrated example, defibrillation lead 102B extends toward a center of the torso of patient 14D, bends or turns near the center of the torso, and extends subcutaneously superior above the ribcage and/or sternum 110. Defibrillation lead 102B may be offset laterally to the left or the right of sternum 110 or located over sternum 110. Defibrillation lead 102B may extend substantially parallel to sternum 102 or be angled lateral from the sternum at either the proximal or distal end.

Defibrillation lead 102B includes an insulative lead body having a proximal end that includes a connector 104 configured to be connected to ICD 10C and a distal portion that includes one or more electrodes. Defibrillation lead 102B also includes one or more conductors that form an electrically conductive path within the lead body and interconnect the electrical connector and respective ones of the electrodes. In the illustrated example, defibrillation lead 102B includes a single defibrillation electrode 106 toward the distal portion of defibrillation lead 102B, e.g., toward the portion of defibrillation lead 102B extending along sternum 110. Defibrillation lead 102B is placed along sternum 110 such that a therapy vector between defibrillation electrode 106 and a housing electrode formed by or on ICD 10C (or other second electrode of the therapy vector) is substantially across a ventricle of heart 16D.

Defibrillation lead 102B may also include one or more sensing electrodes, such as sensing electrodes 108A and 108B, located along the distal portion of defibrillation lead 102B. In the example illustrated in FIG. 5, sensing electrodes 108A and 108B are separated from one another by defibrillation electrode 106. In other examples, however, sensing electrodes 108A and 108B may be both distal of defibrillation electrode 106 or both proximal of defibrillation electrode 106. In other examples, lead 102B may include more or fewer electrodes at various locations proximal and/or distal to defibrillation electrode 106, and lead 102B may include multiple defibrillation electrodes, e.g., defibrillation electrodes 106A and 106B as illustrated in the example of FIGS. 4A-4C.

Figure 6:
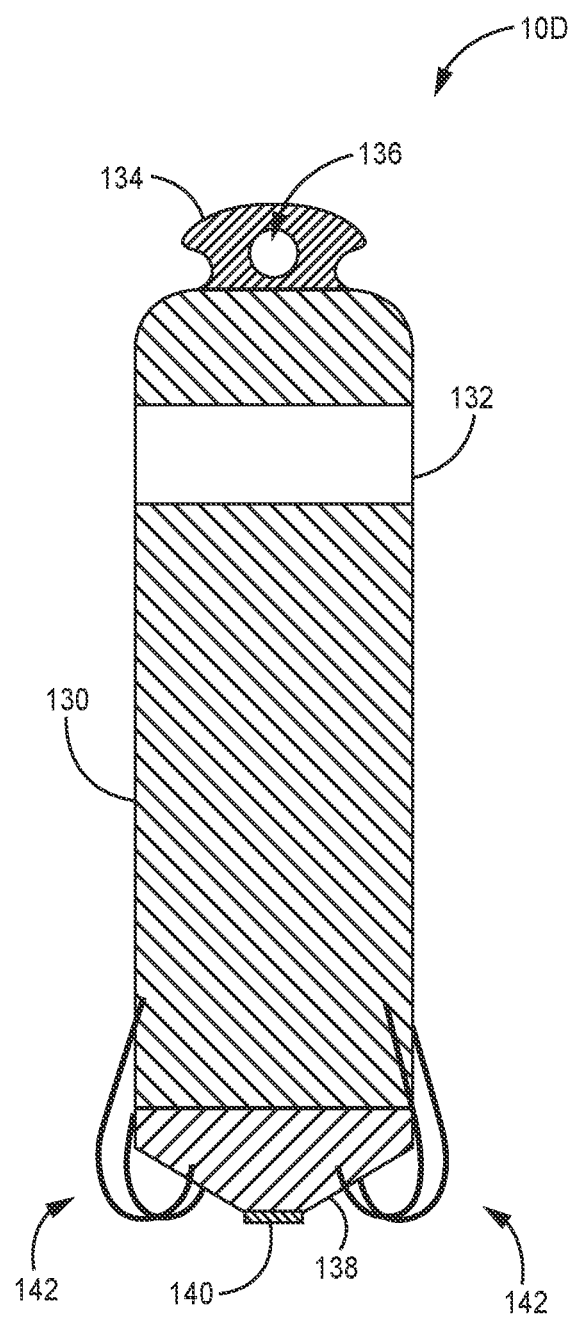
FIG. 6 is a conceptual diagram illustrating an example configuration of the intracardiac pacing device of FIGS. 4A-5.

FIG. 6 is a conceptual drawing illustrating an example configuration of IPD 10D. As shown in FIG. 6, IPD 10D includes case 130, cap 138, electrode 140, electrode 132, fixation mechanisms 142, flange 134, and opening 136. Together, case 130 and cap 138 may be considered the housing of IPD 10D. In this manner, case 130 and cap 138 may enclose and protect the various electrical components, e.g., circuitry, within IPD 10D. Case 130 may enclose substantially all of the electrical components, and cap 138 may seal case 130 and create the hermetically sealed housing of IPD 10D. Although IPD 10D is generally described as including one or more electrodes, IPD 10D may typically include at least two electrodes (e.g., electrodes 132 and 140) to deliver an electrical signal (e.g., therapy such as cardiac pacing) and/or provide at least one sensing vector.

Electrodes 132 and 140 are carried on the housing created by case 130 and cap 138. In this manner, electrodes 132 and 140 may be considered leadless electrodes. In the example of FIG. 6, electrode 140 is disposed on the exterior surface of cap 138. Electrode 140 may be a circular electrode positioned to contact cardiac tissue upon implantation. Electrode 132 may be a ring or cylindrical electrode disposed on the exterior surface of case 130. Both case 130 and cap 138 may be electrically insulating.

Electrode 140 may be used as a cathode and electrode 132 may be used as an anode, or vice versa, for delivering cardiac pacing such as bradycardia pacing, CRT, ATP, or post-shock pacing. However, electrodes 132 and 140 may be used in any stimulation configuration. In addition, electrodes 132 and 140 may be used to detect intrinsic electrical signals from cardiac muscle.

Fixation mechanisms 142 may attach IPD 10D to cardiac tissue. Fixation mechanisms 142 may be active fixation tines, screws, clamps, adhesive members, or any other mechanisms for attaching a device to tissue. As shown in the example of FIG. 6, fixation mechanisms 142 may be constructed of a memory material, such as a shape memory alloy (e.g., nickel titanium), that retains a preformed shape. During implantation, fixation mechanisms 142 may be flexed forward to pierce tissue and allowed to flex back towards case 130. In this manner, fixation mechanisms 142 may be embedded within the target tissue.

Flange 134 may be provided on one end of case 130 to enable tethering or extraction of IPD 10D. For example, a suture or other device may be inserted around flange 134 and/or through opening 136 and attached to tissue. In this manner, flange 134 may provide a secondary attachment structure to tether or retain IPD 10D within heart 16C (or 16D) if fixation mechanisms 142 fail. Flange 134 and/or opening 136 may also be used to extract IPD 10D once the IPD needs to be explanted (or removed) from patient 14D if such action is deemed necessary.

IPD 10D is one example of a pacing device configured to implement the techniques of this disclosure. However, other implantable medical devices may be used to perform the same or similar functions as IPD 10D. For example, an IPD may include a small housing that carries an electrode, similar to IPD 10D, and be configured to be implanted within a chamber of a heart 16. The IPD may also include one or more relatively short leads configured to place one or more respective additional electrodes at another location within the same chamber of the heart or a different chamber of the heart. In this manner, the housing of the IPD may not carry all of the electrodes used to perform functions described herein with respect to IPD 10D. In other examples, each electrode of the IPD may be carried by one or more leads (e.g., the housing of the IPD may not carry any of the electrodes). In some examples, an IPD or other pacing device may include or be coupled to three or more electrodes, where each electrode may deliver therapy and/or detect intrinsic signals.

In another example, a pacing device may be configured to be implanted external to the heart, e.g., near or attached to the epicardium of the heart. An electrode carried by the housing of the pacing may be placed in contact with the epicardium and/or one or more electrodes of leads coupled to the pacing may be placed in contact with the epicardium at locations sufficient to provide cardiac pacing. In still other examples, a pacing device configured to perform the techniques described herein may be implanted subcutaneously or submuscularly, and connected to one or more intracardiac leads carrying one or more electrodes.

Referring back to FIGS. 4A-5, medical device systems 8C and 8D are examples of medical device systems configured to determine whether an acute occurrence of a cardiac event, such as a ventricular tachyarrhythmia, is predicted to occur, and to responsively provide an alert indicating that the acute cardiac event is predicted, and/or deliver a preventative measure, e.g., therapy, configured to prevent the predicted cardiac event. The techniques may be performed by processing circuitry of medical device system 8C or 8D, such as processing circuitry of one or more of ICD 10C, IPD 10D, and external device 30C or 30D, individually, or collectively. Although the example medical devices systems 8C and 8D of FIGS. 4A-5 are illustrated as including both ICD 10C and IPD 10D, other examples may include only one of ICD 10C or IPD 10D, alone, or in combination with other implanted or external devices.

The techniques include determining a respective value for each of a plurality of patient parameters of a patient during each of a plurality of periods, which may be at least one hour, such as approximately one day. The processing circuitry may determine the values of at least some the patient parameters based on physiological signals generated by sensing circuitry of one or both of ICD 10C and IPD 10D, such as cardiac EGM signals generated by sensing circuitry of the IMDs. In some examples, one or both of ICD 10C and IPD 10D may include or be coupled to one or more other sensors that generate one or more other physiological signals, such as signals that vary based on patient motion and/or posture, blood flow, blood pressure (e.g., systems 8C and 8D may include pressure sensing IMD 50, described above with respect to FIG. 1), respiration, or edema. The processing circuitry may determine other patient parameters based on therapies delivered by ICD 10C and/or IPD 10D, such as patient parameters indicating the extent to which patient 14C or 14D is dependent on pacing, e.g., a percentage of time or other characterization of amount of pacing delivered to the patient, or the number of anti-tachyarrhythmia therapies delivered to the patient.

In some examples, the processing circuitry of medical device system 8C or 8D indicates that the acute cardiac event is predicted if the cumulative degree of change, across the patient parameters during the current period is significantly greater than the variation in the patient parameters during N recently preceding periods. For example, as will be described in greater detail below, the processing circuitry may determine, for each of a plurality of patient parameters, a difference metric for a current period based on a value of a patient parameter determined for the current period and a value of the patient parameter determined for an immediately preceding period. In some examples, the processing circuitry determines a score for the current period based on a sum of the difference metrics for the current period for at least some of the plurality of patient parameters. The processing circuitry determines a threshold for the current period based on scores determined for N periods that precede the current period, and compares the score for the current period to the threshold for the current period to determine whether the acute event is predicted. If the processing circuitry determines that the acute cardiac event is predicted, the processing circuitry may generate an alert and, in some examples, control delivery of one or more preventative measures configured to prevent the event, such as cardiac pacing, neuromodulation, or one or more therapeutic substances, e.g., drugs.

Figure 7:
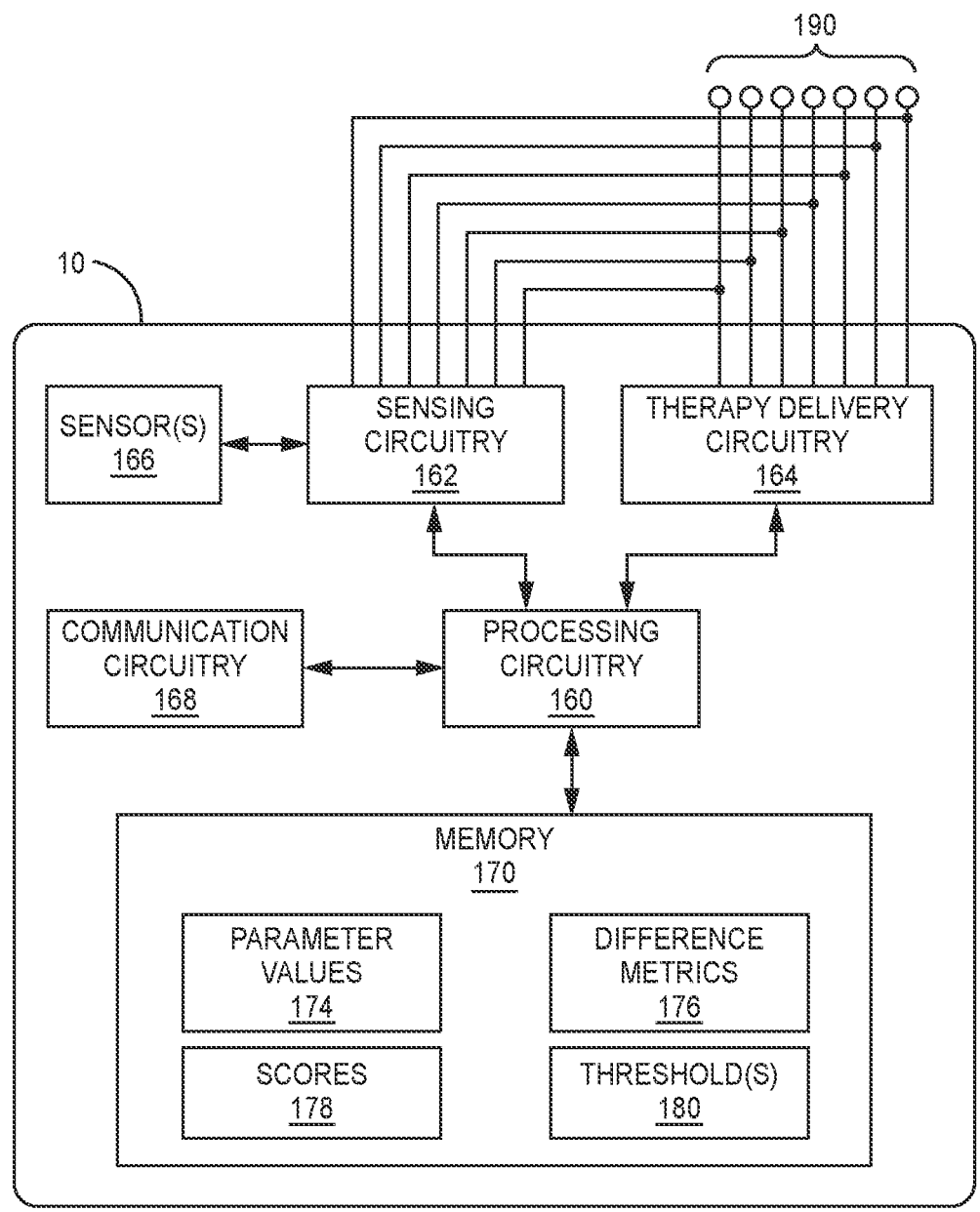
FIG. 7 is a functional block diagram illustrating an example configuration of an implantable medical device.

FIG. 7 is a functional block diagram illustrating an example configuration of an IMD 10. IMD 10 may correspond to any of ICD 10A, ICM 10B, ICD 10C, IPD 10D, or another IMD configured to implement the techniques for predicting an acute cardiac event described in this disclosure. In the illustrated example, IMD 10 includes processing circuitry 160 and an associated memory 170, sensing circuitry 162, therapy delivery circuitry 164, one or more sensors 166, and communication circuitry 168. However, ICD 10A, ICM 10B, ICD 10C, and IPD 10D need not include all of these components, or may include additional components. For example, ICM 10B may not include therapy delivery circuitry 164, in some examples.

Memory 170 includes computer-readable instructions that, when executed by processing circuitry 160, cause IMD 10 and processing circuitry 160 to perform various functions attributed to IMD 10 and processing circuitry 160 herein (e.g., determining patient parameter values, difference metrics, scores and thresholds, and determining whether to provide an alert indicating that an acute cardiac event is predicted). Memory 170 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 160 may include fixed function circuitry and/or programmable processing circuitry. Processing circuitry 160 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 160 may include multiple components, such as any combination of one or more microprocessors, one or more controllers, one or more DSPs, one or more ASICs, or one or more FPGAs, as well as other discrete or integrated logic circuitry. The functions attributed to processing circuitry 160 herein may be embodied as software, firmware, hardware or any combination thereof.

Sensing circuitry 162 and therapy delivery circuitry 164 are coupled to electrodes 190. Electrodes 190 illustrated in FIG. 7 may correspond to, for example: electrodes 12, 22, 24, 26, 28, 44, and 44 of ICD 10A (FIG. 1); electrodes 64 and 66 of ICM 10B (FIG. 3); electrodes 106, 108, and one or more housing electrodes of ICD 10C (FIGS. 4A-5); or electrodes 132 and 140 of IPD 10D (FIG. 6).

Electrical sensing circuitry 162 monitors signals from a selected two or more of electrodes 190 in order to monitor electrical activity of heart 26, impedance, or other electrical phenomenon. Sensing of a cardiac electrical signal may be done to determine heart rates or heart rate variability, or to detect arrhythmias (e.g., tachyarrhythmias or bradycardia) or other electrical signals. In some examples, sensing circuitry 162 may include one or more filters and amplifiers for filtering and amplifying a signal received from electrodes 190.

The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 162 outputs an indication to processing circuitry 160 in response to sensing of a cardiac event (e.g., detected P-waves or R-waves).

In this manner, processing circuitry 160 may receive detected cardiac event signals corresponding to the occurrence of detected R-waves and P-waves in the respective chambers of heart 26. Indications of detected R-waves and P-waves may be used for detecting ventricular and/or atrial tachyarrhythmia episodes, e.g., ventricular or atrial fibrillation episodes. Some detection channels may be configured to detect cardiac events, such as P- or R-waves, and provide indications of the occurrences of such events to processing circuitry 160, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Sensing circuitry 162 may also include a switch module to select which of the available electrodes 190 (or electrode polarities) are used to sense the heart activity. In examples with several electrodes 190, processing circuitry 160 may select the electrodes that function as sense electrodes, i.e., select the sensing configuration, via the switch module within sensing circuitry 162. Sensing circuitry 162 may also pass one or more digitized EGM signals to processing circuitry 160 for analysis, e.g., for use in cardiac rhythm discrimination.

Processing circuitry 160 may implement programmable counters. If IMD 10 is configured to generate and deliver pacing pulses to heart 26, such counters may control the basic time intervals associated with bradycardia pacing (e.g., DDD, VVI, DVI, VDD, AAI, DDI, DDDR, VVIR, DVIR, VDDR, AAIR, DDIR pacing) and other modes of pacing. Intervals defined by processing circuitry 160 may include atrial and ventricular pacing escape intervals, refractory periods during which sensed P-waves and R-waves are ineffective to restart timing of the escape intervals, and the pulse widths of the pacing pulses. The durations of these intervals may be determined by processing circuitry 160 in response to pacing mode parameters stored in memory 170.

Interval counters implemented by processing circuitry 160 may be reset upon sensing of R-waves and P-waves with detection channels of sensing circuitry 162, or upon the generation of pacing pulses by therapy delivery circuitry 164, and thereby control the basic timing of cardiac pacing functions, including bradycardia pacing, CRT, ATP, or post-shock pacing. The value of the count present in the interval counters when reset by sensed R-waves and P-waves may be used by processing circuitry 160 to measure the durations of R-R intervals, P-P intervals, P-R intervals, and R-P intervals, which are measurements that may be stored in memory 170. Processing circuitry 160 may use the count in the interval counters to detect a tachyarrhythmia event, such as atrial fibrillation (AF), atrial tachycardia (AT), VF, or VT. These intervals may also be used to detect the overall heart rate, ventricular contraction rate, and heart rate variability. A portion of memory 170 may be configured as a plurality of recirculating buffers, capable of holding series of measured intervals, which may be analyzed by processing circuitry 160 in response to the occurrence of a pace or sense interrupt to determine whether the patient's heart 26 is presently exhibiting atrial or ventricular tachyarrhythmia.

In some examples, an arrhythmia detection method may include any suitable tachyarrhythmia detection algorithms. In one example, processing circuitry 160 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies, such as those methodologies that utilize timing and morphology of the electrocardiogram, may also be employed by processing circuitry 160 in other examples.

In some examples, processing circuitry 160 may determine that tachyarrhythmia has occurred by identification of shortened R-R (or P-P) interval lengths. Generally, processing circuitry 160 detects tachycardia when the interval length falls below 220 milliseconds and fibrillation when the interval length falls below 180 milliseconds. In other examples, processing circuitry 160 may detect ventricular tachycardia when the interval length falls between 330 milliseconds and ventricular fibrillation when the interval length falls below 240 milliseconds. These interval lengths are merely examples, and a user may define the interval lengths as desired, which may then be stored within memory 170. This interval length may need to be detected for a certain number of consecutive cycles, for a certain percentage of cycles within a running window, or a running average for a certain number of cardiac cycles, as examples. In other examples, additional patient parameters may be used to detect an arrhythmia. For example, processing circuitry 160 may analyze one or more morphology measurements, impedances, or any other physiological measurements to determine that patient 14 is experiencing a tachyarrhythmia.

In addition to detecting and identifying specific types of cardiac events, e.g., cardiac depolarizations, sensing circuitry 162 may also sample the detected intrinsic signals to generate an electrogram or other time-based indication of cardiac events. Sensing circuitry 162 may include an analog-to-digital converter or other circuitry configured to sample and digitize the electrical signal sensed via electrodes 190. Processing circuitry 160 may analyze the digitized signal for a variety of purposes, including morphological identification or confirmation of tachyarrhythmia of heart 26. As another example, processing circuitry 160 may analyze the digitized cardiac electrogram signal to identify and measure a variety of morphological features of the signal. As described in greater detail below, the morphological features of the cardiac electrogram may be patient parameters, and their measurements patient parameter values, used to determine whether an acute cardiac event, e.g., ventricular tachyarrhythmia, is predicted to occur.

In some examples, sensing circuitry 162 is configured to sense other physiological signals of patient. For example, sensing circuitry 162 may be configured to sense signals that vary with changing thoracic impedance of patient 14. The thoracic impedance may vary based on fluid volume or edema in patient 14.

Sensing circuitry 162 may use any two or more of electrodes 190 to sense thoracic impedance. As the tissues within the thoracic cavity of patient 14 change in fluid content, the impedance between two electrodes may also change. For example, the impedance between a defibrillation coil electrode (42, 44, 106) and the housing electrode may be used to monitor changing thoracic impedance.

In some examples, processing circuitry 160 measured thoracic impedance values to determine a fluid index. As more fluid is retained within patient 14, e.g., edema increases, and the thoracic impedance decreases or remains relatively high, the fluid index increases. Conversely, as the thoracic impedance increases or remains relatively low, the fluid index decreases. An example system for measuring thoracic impedance and determining a fluid index is described in U.S. Pat. No. 8,255,046 to Sarkar et al., entitled, "DETECTING WORSENING HEART FAILURE BASED ON IMPEDANCE MEASUREMENTS," which issued on Aug. 28, 2012 and is incorporated herein by reference in its entirety.

The thoracic impedance may also vary with patient respiration. In some examples, processing circuitry 160 may determine values of one or more respiration-related patient parameters based on thoracic impedance sensed by sensing circuitry 162. Respiration-related patient parameters may include, as examples, respiration rate, respiration depth, or the occurrence or magnitude of dyspnea or apneas.

The magnitude of the cardiac electrogram may also vary based on patient respiration, e.g., generally at a lower frequency than the cardiac cycle. In some examples, processing circuitry 160 and/or sensing circuitry 162 may filter the cardiac electrogram to emphasize the respiration component of the signal. Processing circuitry 160 may analyze the filtered cardiac electrogram signal to determine values of respiration-related patient parameters.

In the example of FIG. 7, IMD 10 includes one or more sensors 166 coupled to sensing circuitry 162. Although illustrated in FIG. 7 as included within IMD 10, one or more of sensors 166 may be external to IMD 10, e.g., coupled to IMD 10 via one or more leads, or configured to wirelessly communicate with IMD 10. In some examples, sensors 166 transduce a signal indicative of a patient parameter, which may be amplified, filtered, or otherwise processed by sensing circuitry 162. In such examples, processing circuitry 160 determines values of patient parameters based on the signals. In some examples, sensors 166 determine the patient parameter values, and communicate them, e.g., via a wired or wireless connection, to processing circuitry 160.

In some examples, sensors 166 include one or more accelerometers, e.g., one or more 3-axis accelerometers. Signals generated by the one or more accelerometers may be indicative of, as examples, gross body movement (e.g., activity) of patient 14, patient posture, heart sounds or other vibrations or movement associated with the beating of the heart, or coughing, rales, or other respiration abnormalities. In some examples, sensors 166 include one or more microphones configured to detect heart sounds or respiration abnormalities, and/or other sensors configured to detect patient activity or posture, such as gyroscopes and/or strain gauges. In some examples, sensors 166 may include sensors configured to transduce signals indicative of blood flow, oxygen saturation of blood, or patient temperature, and processing circuitry 160 may determine patient parameters values based on these signals.

In some examples, sensors 166 include one or more pressure sensors that transduce one or more signals indicative of blood pressure, and processing circuitry 160 determines one or more patient parameter values based on the pressure signals. Patient parameter values determined based on pressure may include, as examples, systolic or diastolic pressure values, such as pulmonary artery diastolic pressure values. In some examples, a separate pressure-sensing IMD 50 includes one or more sensors and sensing circuitry configured to generate a pressure signal, and processing circuitry 160 determines patient parameter values related to blood pressure based on information received from IMD 50.

Therapy delivery circuitry 164 is configured to generate and deliver electrical therapy to the heart. Therapy delivery circuitry 164 may include one or more pulse generators, capacitors, and/or other components capable of generating and/or storing energy to deliver as pacing therapy, defibrillation therapy, cardioversion therapy, other therapy, or a combination of therapies. In some instances, therapy delivery circuitry 164 may include a first set of components configured to provide pacing therapy and a second set of components configured to provide anti-tachyarrhythmia shock therapy. In other instances, therapy delivery circuitry 164 may utilize the same set of components to provide both pacing and anti-tachyarrhythmia shock therapy. In still other instances, therapy delivery circuitry 164 may share some of the pacing and shock therapy components while using other components solely for pacing or shock delivery.

Therapy delivery circuitry 164 may include charging circuitry, one or more charge storage devices, such as one or more capacitors, and switching circuitry that controls when the capacitor(s) are discharged to electrodes 190 and the widths of pulses. Charging of capacitors to a programmed pulse amplitude and discharging of the capacitors for a programmed pulse width may be performed by therapy delivery circuitry 164 according to control signals received from processing circuitry 160, which are provided by processing circuitry 160 according to parameters stored in memory 170. Processing circuitry 160 controls therapy delivery circuitry 164 to deliver the generated therapy to the heart via one or more combinations of electrodes 190, e.g., according to parameters stored in memory 170. Therapy delivery circuitry 164 may include switch circuitry to select which of the available electrodes 190 are used to deliver the therapy, e.g., as controlled by processing circuitry 160.

In some examples, IMD 10 may additionally or alternatively be configured to deliver other therapies configured to prevent the predicted acute cardiac event. For example, processing circuitry 160 may control therapy delivery circuitry 164 to deliver cardiac pacing therapy configured to prevent a ventricular tachyarrhythmia, such as overdrive pacing therapy when one or more of the patient parameters 174 indicate that the heart rate is not fast or down-drive pacing therapy if one or more of the patient parameters 174 indicate that the heart rate is too fast.

As another example, IMD 10 may additionally or alternatively be configured to deliver neuromodulation therapy to prevent an acute cardiac event, such as ventricular tachyarrhythmia, heart failure decompensation, or ischemia. In such examples, processing circuitry 160 may be programmed, and therapy delivery circuitry 164 and electrodes 190 configured and placed, to generate and deliver the neuromodulation therapy. Example neuromodulation therapies include vagal nerve stimulation, spinal cord stimulation, peripheral nerve stimulation, cardiac intrinsic nerve modulation, and cardiac stellate ganglion stimulation.

As another example, IMD 10 may additionally or alternatively be configured to deliver a therapeutic substance, e.g., infuse a drug. In such examples, IMD 10 may include a pump to deliver the substance, and processing circuitry

160 may be configured to control the pump according to therapy parameters stored in memory 170. Examples of delivery of therapy substances to prevent an acute cardiac event include delivery of substances that modulate the cardiovascular or neurological systems of the patient.

According to the acute cardiac event detection techniques described herein, processing circuitry 160 periodically, i.e., for each of a plurality of periods, determines a respective value for each of a plurality of patient parameters. The determined patient parameter values are stored as patient parameter values 174 in memory 170. In some examples, the length of each period is greater than one hour, such as a predetermined integer number of hours or days. In some examples, the period length is between eight hours and three days, such as one day.

Each of patient parameter values 174 may be the single value of a patient parameter determined during the period. In other examples, each of patient parameter values 174 is a representative value determined based on a plurality of values determined during the period. In some examples, patient parameter values 174 may include one or more means, medians, modes, sums, or other values determined based on a plurality of values of a patient parameter determined during the period.

The plurality of patient parameters may include one or more parameters determined based on the cardiac electrogram, such as one or more heart rate parameters, and/or one or more tachyarrhythmia episode parameters. Example heart rate parameters include average heart rate during the period, average daytime heart rate during the period, average nighttime heartrate during the period, and one or more measures of heart rate variability during the period. Example tachyarrhythmia episode parameters include the number, frequency and/or duration (total, mean, or median) of tachyarrhythmia episodes during the period, such as atrial tachycardia episodes, atrial fibrillation episodes, or non-sustained tachyarrhythmia (NST) episodes. NST episodes may be a series of short R-R intervals greater than an NST threshold number of short R-R intervals, but fewer than a number of intervals to detect (NID) for ventricular tachyarrhythmia. Another example patient parameter that processing circuitry 160 may determine based on the cardiac electrogram is the ventricular rate during atrial tachyarrhythmia, e.g., atrial fibrillation, which may be a mean or median value during the period.

Other patient parameters determined based on the cardiac electrogram include morphological features of the cardiac electrogram, such as QRS width or duration, QT interval length, T-wave amplitude, R-R interval length, an interval between a peak and the end of the T-wave, a ratio between the T-wave peak to end interval and the QT interval lengths, or T-wave alternan. The presence of T-wave alternan may be detected as a periodic (e.g., beat-to-beat) variation in the amplitude or morphology of the T-wave. A T-wave alternan patient parameter value 174 may be an indication of the presence, number, frequency, or duration (total, mean, or median) of T-wave alternan episodes. Other patient parameter values 174 based cardiac electrogram morphological interval lengths may be means or medians of a plurality of measurements made during the period, e.g., daily mean or median values.

The plurality of patient parameters may additionally or alternatively include at least one patient parameter indicative of edema, and processing circuitry 160 may determine values 174 of such patient parameters based on sensed thoracic impedance, as described above. In some examples, a patient parameter value 174 may be a maximum, minimum, mean, or median thoracic impedance value during a period. In some examples, a patient parameter value 174 may be a fluid index value during the period. Processing circuitry 160 may increment and decrement a fluid index value based on an accumulation of differences between a thoracic impedance value (or short-term average of impedance values) and a threshold determined based on a long-term average of thoracic impedance values.

The plurality of patient parameters may additionally or alternatively include at least one patient parameter indicative of patient activity, e.g., gross patient body movement or motion. In some examples, processing circuitry 160 determines a number of activity counts based on one or more accelerometer signals crossing (e.g., exceeding) one or more thresholds. A patient parameter value 174 during a period may be a total, mean, or median number of counts during the period.

The plurality of patient parameters may additionally or alternatively include at least one patient parameter indicative of cardiovascular pressure, and processing circuitry 160 may determine values 174 of such patient parameters based on generated pressure waveform, e.g., generated by a sensor 166 or pressure-sensing IMD 50, as described above. The patient parameter values 174 for the period may include a maximum, minimum, mean, or median of systolic pressure and/or diastolic pressure, e.g., pulmonary artery diastolic pressure.

The plurality of patient parameters may additionally or alternatively include at least one patient parameter determined based on patient respiration, and processing circuitry 160 may determine values 174 of such parameters based on a generated signal that varies based on respiration as described above, such as a signal that varies based on thoracic impedance. The patient parameter values 174 for the period may include a maximum, minimum, mean, or median of respiration rate, e.g., for a day, daytime, or nighttime. The patient parameter values 174 for the period may include an indication of the presence, a number, a frequency, or a duration (total, mean, or median) of respiration episodes, such as apneas or dyspneas.

Processing circuitry 160 may additionally or alternatively determine values 174 of one or more patient parameters based on a generated signal that varies based on sound or other vibrations, which may indicate heart sounds, coughing, or rales. Patient parameter values may include morphological measurements of the S1 and S2 heart sounds, the presence or frequency of occurrence of S3 and/or S4 heart sounds, or the presence, number, frequency, or duration (total, mean, or median) of episodes or coughing or rales. Other patient parameter values 174 that processing circuitry 160 may additionally or alternatively periodically determine based on signals generated by sensors 166 include maximum, minimum, mean, or median values of blood flow, blood oxygen saturation, or temperature.

The plurality of patient parameters may additionally or alternatively include at least one patient parameter determined based on delivery of therapy to patient 14, e.g., by IMD 10. In some examples, a patient parameter value 174 for a period indicates an amount of cardiac pacing delivered to the patient during the period, such as a total duration or percentage of the period during which atrial pacing, ventricular pacing, and/or CRT was delivered.

In some examples, the plurality of patient parameter values 174 determined for each period includes: a percentage of the period during which IMD 10 delivered ventricular pacing to patient 14; a percentage of the period during which IMD 10 delivered atrial pacing to patient 14; an average daytime ventricular heart rate; an average nighttime ventricular heart rate; a frequency or duration of atrial tachycardia event, atrial fibrillation events, and/or NSTs during the period; a total number of patient activity counts during the period; a measure of heart rate variability during the period; a daily thoracic impedance value; and a fluid index value. In some examples, the plurality of patient parameter values 174 includes all or subset of the parameters included in Cardiac Compass® trends generated by IMDs available from Medtronic, plc, of Dublin Ireland. In some examples, the plurality of patient parameter values 174 additionally includes one or more cardiac electrogram morphology parameters.

Processing circuitry 160 determines a difference metric 176 for each of the plurality patient parameters for the period. Processing circuitry 160 determines the difference metric 176 for each patient parameter based on a difference between a current value 174 of the patient parameter for the current period, and an immediately preceding value 174 of the patient parameter for the immediately preceding period. In some examples, processing circuitry 160 determines the difference metric 176 for each of the patient parameters according to the following equation:

$$\Delta V_{t,param_n} = \text{Value}_{t-1} - \text{Value}_{t-2} \quad \text{(Eq. 1)}$$

In some examples, the difference metric may be referred to as "$\Delta V_t$," such as in Equation 1, or may be referred to as "$V_t$," such as in Equation 2 below. The difference metric may be indicative of daily changes in values of risk factors, for example. In some examples, processing circuitry 160 determines the difference metric 176 for each of the plurality patient parameters for the period based on the difference between the current and preceding values, and a standard deviation (or other measure of variation) of values 174 of the patient parameter for N preceding periods. N is an integer constant, e.g., between 5 and 50, such as between 7 and 15 or, in one example, 15. In examples in which each period is a day, the N preceding periods may be N preceding days. Determining the difference metric based on the difference between the current and preceding values and a standard deviation or other measure of variation allow the difference metric to better represent the difference in the patient parameter during the current period rather than baseline variation of the patient parameter and/or noise. In some examples, processing circuitry 160 determines the difference metric 176 for each of the patient parameters according to the following equation:

$$V_{t,param_n} = \frac{\text{Value}_{t-1} - \text{Value}_{t-2}}{SD_t} \quad \text{(Eq. 2)}$$

Processing circuitry 160 determines a score 178 for the period based on the plurality of patient parameter-specific difference metrics 176 for the period. In some examples, processing circuitry 160 determines the score 178 for the period based on a sum of squares of the difference metrics 176 for the period or a sum of absolute values of the difference metrics 176. The difference metrics 176 may be positive or negative, and use of the sum of squares or absolute values may enable the score 178 to reflect the absolute magnitudes of change of the plurality of patient parameters during the period. In some examples, processing circuitry 160 determines the score 178 for the period using a sum of squares of difference metrics 176 according to the following equation, where n is the number of patient parameters for which difference metrics 176 are determined during the period (in this case 8):

$$\text{Score}_t = \Sigma_{n=1}^{8} V_{t,param_n}^2 \quad \text{(Eq. 3)}$$

In some examples, processing circuitry 160 applies coefficients or weights to one or more of difference metrics 176 when determining a score 178 for a period, such as in Equation 4 below. The weights may be determined and/or adjusted empirically based on an analysis of the sensitivity and specificity of the score 178 in predicting occurrence of acute cardiac events over time for patient 14 or population of patients, e.g., having similar characteristics to patient 14. The values of the weights may be adjusted over time, e.g., on a period-by-period or less frequent basis.

$$\text{Score}_t = \Sigma_{n=1}^{8} \alpha_n |\Delta V_{t,param_n}| \quad \text{(Eq. 4)}$$

The score of Equation 4 may be indicative of the weighted risk score based on pathophysiological changes. An example of a coefficient or weight, as described above, may include "$\alpha_n$" as in Equation 4. $\alpha_n$ may be a wright constant, such that the moving window size, silence interval, threshold setting, and prediction window may be better optimized. In an example, a may be a value that is based on findings from previous research, event history from an individual or more than one individual, or other factors. For example, T-wave alternans may be relevant to an arrhythmic event. As such, the difference value of T wave alternans may be weighted up (e.g., 5 µV weighted to 5×10). In an example, if a previous event occurred when thoracic impendence was relatively high, then the change value for impedance can be weighted higher. On the other hand, for example, some changes may be good changes that may be weighted smaller or assigned zero weight (e.g., no risk, such as an increase in HRV or HRV above a particular value, such as about 80 ms).

Processing circuitry 160 also determines a threshold 180 for the period based on scores 178 for N preceding periods, wherein N is the integer constant, e.g., 15. In some examples, processing circuitry 160 determines the threshold 180 based on a mean or median of the N preceding scores, e.g., by multiplying a median of the N scores and a coefficient. The coefficient may be, for example, between 1 and 3, and determined for a given patient 14 or patient population based on a receiver operator characteristic (ROC).

Processing circuitry 160 compares the score for the period to the threshold for the period. If the score exceeds the threshold, e.g., is greater than, or greater than or equal to the threshold, processing circuitry 160 provides an alert that a cardiac event, e.g., a ventricular tachyarrhythmia, is predicted to acutely occur. In some examples, processing circuitry 160 may additionally control therapy delivery circuitry 162, a pump included in IMD 10, or another implanted or external medical device to deliver a therapy configured to prevent the acute cardiac event, such as a pacing therapy, a neuromodulation therapy, or a therapeutic substance. In some examples, a clinician may prescribe or deliver, or control another device to deliver, such a therapy based on the alert generated by processing circuitry 160.

Communication circuitry 168 includes any suitable hardware, firmware, software, or any combination thereof for communicating with another device, such as an external device 30 or another IMD or sensor. Under the control of processing circuitry 160, communication circuitry 168 may receive downlink telemetry from and send uplink telemetry to external device 30 or another device with the aid of an antenna, which may be internal and/or external. In some examples, communication circuitry 168 may communicate with a local external device, and processing circuitry 160 may communicate with a networked computing device via the local external device and a computer network, such as the Medtronic CareLink® Network developed by Medtronic, plc, of Dublin, Ireland.

A clinician or other user may retrieve data from IMD 10 using external device 30 or another local or networked computing device configured to communicate with processing circuitry 160 via communication circuitry 168. The clinician may also program parameters of IMD 10 using external device 30 or another local or networked computing device. In some examples, the clinician may select patient parameters used to predict acute cardiac events, select values for a coefficient used to determine threshold 180, select a value for the number of N preceding periods, and receive alerts that indicate that the acute cardiac event is predicted via communication circuitry 168 and external device 130 and/or another computing device.

Figure 8:
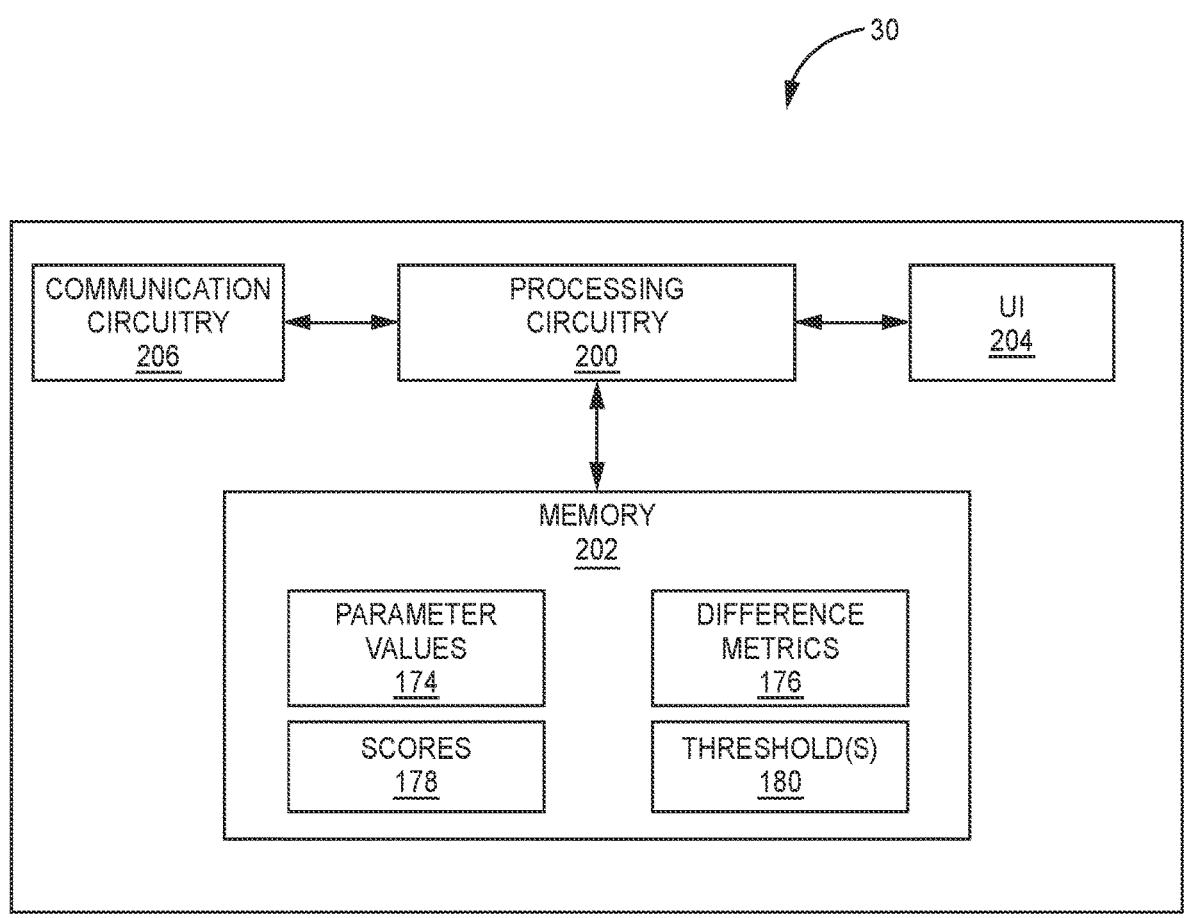
FIG. 8 is a functional block diagram illustrating an example configuration of an external device configured to communicate with one or more implantable medical devices.

FIG. 8 is a functional block diagram illustrating an example configuration of an external device 30 configured to communicate with one or more IMDs 10. In the example of FIG. 8, external device 30 includes processing circuitry 200, memory 202, user interface (UI) 204, and communication circuitry 206. External device 30 may correspond to any of external devices 30A-30C described with respect to FIGS. 1, 2, and 4A-5. External device 30 may be a dedicated hardware device with dedicated software for the programming and/or interrogation of an IMD 10. Alternatively, external device 30 may be an off-the-shelf computing device, e.g., running an application that enables external device 30 to program and/or interrogate IMD 10.

In some examples, a user uses external device 30 to select or program any of the values for operational parameters of IMD 10, e.g., for patient parameter sensing, therapy delivery, and acute cardiac event prediction. In some examples, a user uses external device 30 to receive data collected by IMD 10, such as patient parameter values 174 or other operational and performance data of IMD 10. The user may also receive alerts provided by IMD 10 that indicate that an acute cardiac event, e.g., ventricular tachyarrhythmia, is predicted. The user may interact with external device 30 via UI 204, which may include a display to present a graphical user interface to a user, and a keypad or another mechanism (such as a touch sensitive screen) for receiving input from a user. External device 30 may communicate wirelessly with IMD 10 using communication circuitry 206, which may be configured for RF communication with communication circuitry 168 of IMD 10.

Processing circuitry 200 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 200 may include multiple components, such as any combination of one or more microprocessors, one or more DSPs, one or more ASICs, or one or more FPGAs, as well as other discrete or integrated logic circuitry, and/or analog circuitry.

Memory 202 may store program instructions, which may include one or more program modules, which are executable by processing circuitry 200. When executed by processing circuitry 200, such program instructions may cause processing circuitry 200 and external device 30 to provide the functionality ascribed to them herein. The program instructions may be embodied in software, firmware and/or RAMware. Memory 202 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In some examples, processing circuitry 200 of external device 30 may be configured to provide some or all of the functionality ascribed to processing circuitry 160 of IMD 10 herein. For example, processing circuitry 200 may receive physiological signals generated by one or more IMDs 10 and determine values 174 of each of a plurality of patient parameters during each of a plurality of periods, and/or may receive patient parameter values 174 for the plurality of periods from one or more IMDs 10. Processing circuitry 200 may determine difference metrics 176, scores 178, and thresholds 180 based on the patient parameter values 174 in the manner described above with respect to processing circuitry 160 of IMD 10. Processing circuitry 200 may also compare scores 178 to thresholds 180 and generate an alert and/or control delivery of preventative therapy by one or more implanted or external medical devices in the manner described above with respect to processing circuitry 160 of IMD 10. Processing circuitry 200 may provide an alert to a user via UI 204, or via another device with which processing circuitry 200 communicates via communication circuitry 206.

Figure 9:
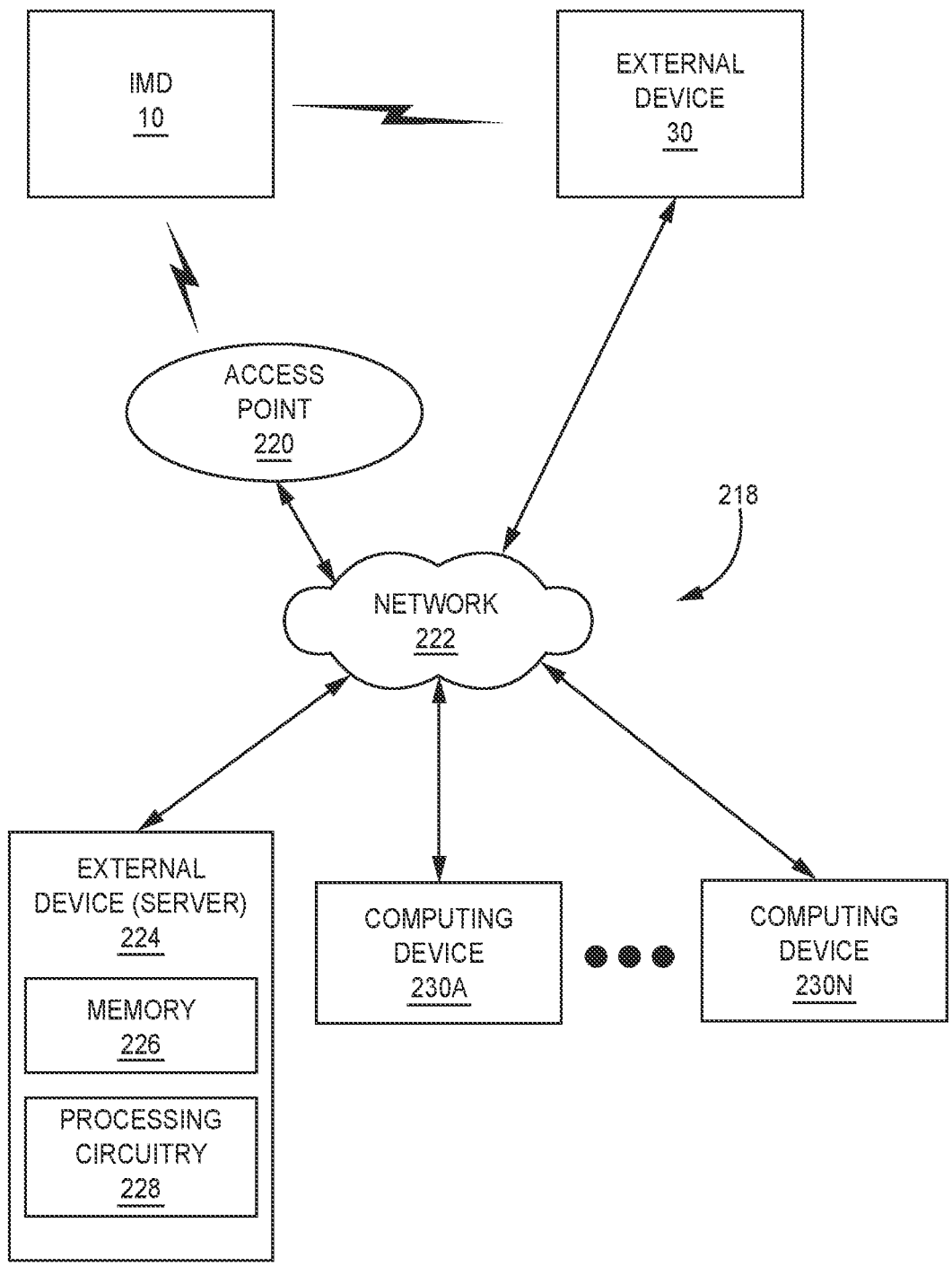
FIG. 9 is a functional block diagram illustrating an example system that includes remote computing devices, such as a server and one or more other computing devices, that are connected to an implantable medical device and/or external device via a network.

FIG. 9 is a functional block diagram 218 illustrating an example system that includes external computing devices, such as a server 224 and one or more other computing devices 230A-230N, that are coupled to IMD 10 and external device 30 via a network 222. In this example, IMD 10 may use its communication module 168 to, e.g., at different times and/or in different locations or settings, communicate with external device 30 via a first wireless connection, and to communication with an access point 220 via a second wireless connection. In the example of FIG. 9, access point 220, external device 30, server 224, and computing devices 230A-230N are interconnected, and able to communicate with each other, through network 222.

Access point 220 may comprise a device that connects to network 222 via any of a variety of connections, such as telephone dial-up, digital subscriber line (DSL), or cable modem connections. In other examples, access point 220 may be coupled to network 222 through different forms of connections, including wired or wireless connections. In some examples, access point 220 may be co-located with patient 14. Access point 220 may interrogate IMD 10, e.g., periodically or in response to a command from patient 14 or network 222, to retrieve physiological signals, patient parameter values 174, difference metrics 176, scores 178, thresholds 180, alerts of acute cardiac events, and/or other operational or patient data from IMD 10. Access point 220 may provide the retrieved data to server 224 via network 222.

In some cases, server 224 may be configured to provide a secure storage site for data that has been collected from IMD 10 and/or external device 30. In some cases, server 224 may assemble data in web pages or other documents for viewing by trained professionals, such as clinicians, via computing devices 230A-230N. The illustrated system of FIG. 9 may be implemented, in some aspects, with general network technology and functionality similar to that provided by the Medtronic CareLink® Network developed by Medtronic plc, of Dublin, Ireland.

In some examples, one or more of access point 220, server 224, or computing devices 230 may be configured to perform, e.g., may include processing circuitry configured to perform, some or all of the techniques described herein, e.g., with respect to processing circuitry 160 of IMD 10 and processing circuitry 200 of external device 30, relating to prediction of acute cardiac events, such as ventricular tachyarrhythmia. In the example of FIG. 9, server 224 includes a memory 226 to store physiological signals or patient parameter values 174 received from IMD 10 and/or external device 30, and processing circuitry 228, which may be configured to provide some or all of the functionality ascribed to processing circuitry 160 of IMD 10 and processing circuitry 200 of external device 30 herein. For example, processing circuitry 228 may determine values 174 of each of a plurality of patient parameters during each of a plurality of periods, and/or may receive patient parameter values 174 for the plurality of periods from one or more IMDs 10. Processing circuitry 228 may determine difference metrics 176, scores 178, and thresholds 180 based on the patient parameter values 174 in the manner described above with respect to processing circuitry 160 of IMD 10. Processing circuitry 227 may also compare scores 178 to thresholds 180 and generate an alert and/or control delivery of preventative therapy by one or more implanted or external medical devices in the manner described above with respect to processing circuitry 160 of IMD 10. Processing circuitry 228 may provide an alert to a user via network 222, e.g., via external device 30 or one of computing devices 170.

Figure 10:
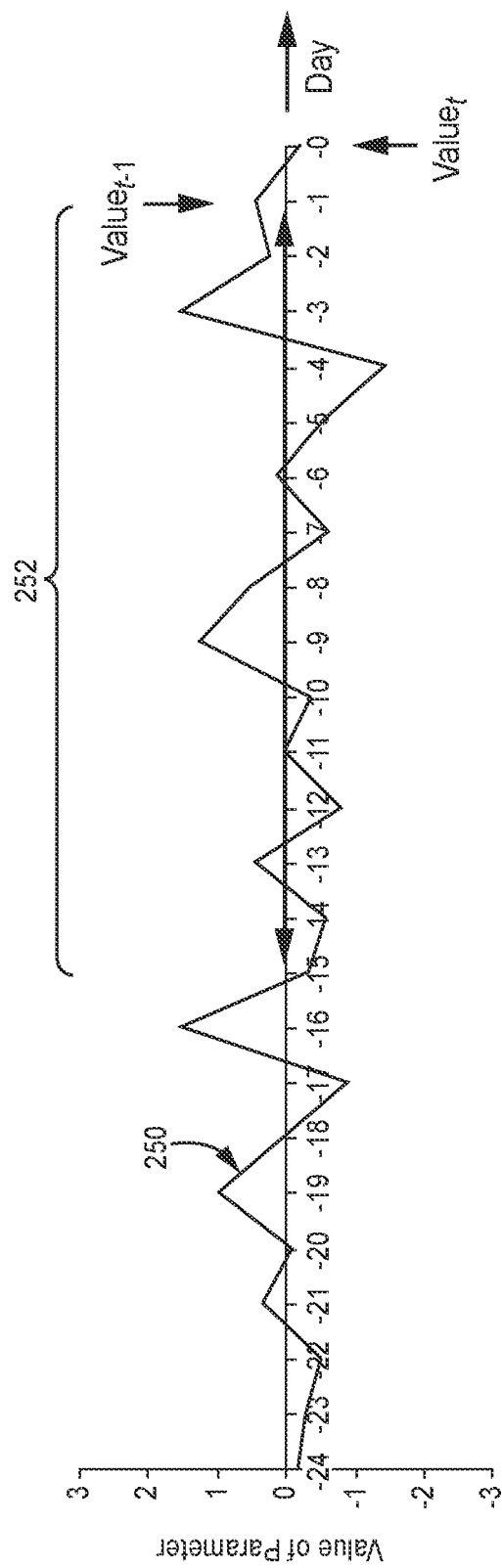
FIG. 10 is a timing diagram illustrating values of a physiological parameter of a patient over a plurality of time periods.

FIG. 10 is a timing diagram illustrating score 178 of a plurality of patient parameters of a patient over a plurality of time periods. More particularly, FIG. 10 illustrates a trend 250 of the scores of the plurality of periods, each of which in this example is one day. FIG. 10 also illustrates the score 178 of patient parameter for the current period ($Score_t$) and the score 178 of patient parameter for the immediately preceding period ($Score_{t-1}$).

FIG. 10 also illustrates a window 252 of N preceding periods, which in this case are the N most recent preceding periods including the immediately preceding period. N is an integer constant number of periods. In the illustrated example, N is 15 days. In an example, N may be less than 15 days (e.g., 14, 10, less than 7, or other values). In an example, N may be more than 15 days (e.g., 16, 18, more than 16, or other values). In an example, N may be 3 days. Window 252 may include consecutive periods, or may include non-consecutive periods based on exclusion of one or more recent periods as described below with respect to FIGS. 13A and 13B.

In an example, a prediction window may be the period before a predicted VTVF event. For example, the prediction window may be 1 day, such as in FIG. 10. As such, if any score in a 1 day period (e.g., the current period) crosses the threshold from the N preceding periods (e.g., 15 as in FIG. 10), then a prediction will be made. In another example, the prediction window may be less than one day (e.g., 20 hours, less than 20 hours, or another value). In an example, the prediction window may be more than one day (e.g., 2 days, 3 days, 3.5 days, more than 3 days, or another value). In an example, the prediction window is about 72 hours (e.g., 70 hours to 74 hours). Any value for N may be used with any value for the prediction window (e.g., N is 15 days and the prediction window is 1 day; N is 14 days and the prediction window is 3 days; or any other combination.

As described above, processing circuitry of a medical device system 8 may determine a difference metric based on the difference between the values 174 for the current period and the immediately preceding period, e.g., according to equation 1. In some examples, processing circuitry of a medical device system 8 may determine a difference metric based on the difference between the values 174 for the current period and the immediately preceding period, and a representation of the variation values 174 for the N preceding periods, e.g., the standard deviation of the N preceding values according to equation 2, which may exclude or minimize the effect of baseline variation and/or noise in the difference metric. Processing circuitry of a medical device system 8 may also determine a threshold 180 based on scores 178 of N preceding periods within window 252, e.g., based on a median of the scores within window 252, as described above.

Figure 11:
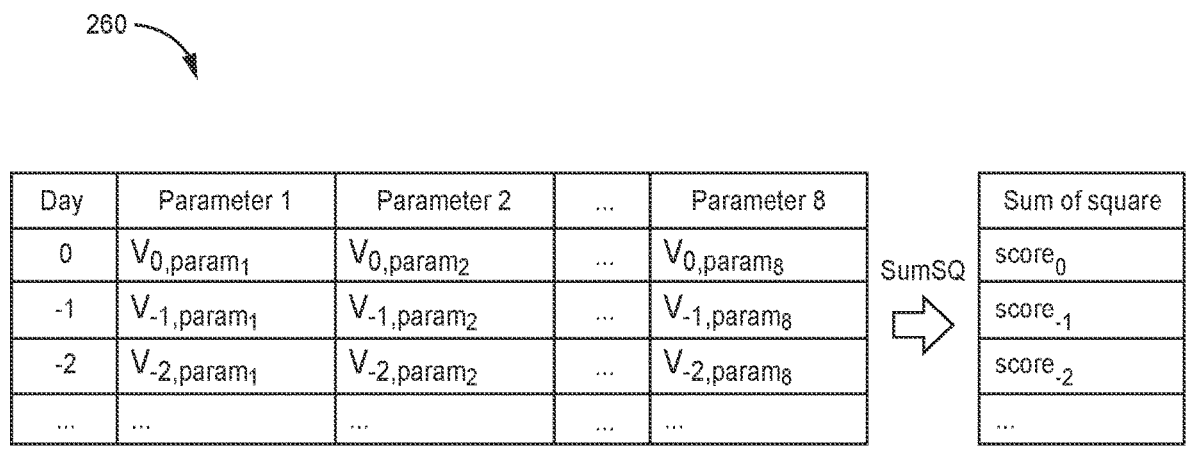
FIG. 11 is a tabular representation of an example technique for periodically determining a score based on respective difference metrics for each of a plurality of physiological parameters.

FIG. 11 is a tabular representation 260 of an example technique for periodically determining a score 178 based on respective difference metrics 176 for each of a plurality of patient parameters. Tabular representation 260 illustrates difference metrics 176 determined according to equation 1 or 2 in the form $V_t, param_n$, where t represents the period and n represents the patient parameter. There are 8 different patient parameters for which values 174 are determined in the illustrated example. Tabular representation 260 also illustrates scores 178 determined based on the sum of squares of the difference metrics 176, e.g., according to equation 3, in the form of $score_t$, where t represents the period.

FIG. 12 is a tabular representation 270 of another example technique for periodically determining a score 178 based on respective difference metrics 176 for each of a plurality of patient parameters. The example technique illustrated by representation 270 may be substantially similar to that of representation 260 of FIG. 11. However, according to the example technique of FIG. 12, processing circuitry of a medical device system 8 may additionally determine whether to include or exclude a particular patient parameter or difference metric 176 from the score 178 based on a patient parameter specific criterion. In some examples, processing circuitry of a medical device system 8 compares each of one or more of the difference metrics 176 determined for a given period to a respective patient parameter specific criterion, and determines whether to include the one or more difference metrics 176 in the score 178 based on the comparison.

The patient parameter specific criterion may discern whether a difference metric 176 for a particular patient parameter, e.g., a direction (positive or negative) or magnitude of the difference metric, indicates a likelihood of an acute cardiac event, or, if included in a sum with other difference metrics, would obscure their ability to indicate the likelihood of an acute cardiac event. The comparisons of difference metrics 176 to patient parameter specific criteria, and inclusion or exclusion of difference metrics 176 from scores 178, may occur on a period-by-period basis, or on a less frequent basis. In some examples, the processing circuitry or a user may determine that a particular patient parameter is not relevant for predicting the occurrence of an acute cardiac event for a given patient or patient population, and exclude the patient parameter permanently or until included by user command. Exclusion of a difference metric 176 for a particular patient parameter may include assigning a value of 0 to the difference metric when determining a score 178 for the period, e.g., according to a sum of squares of difference metrics 176.

Example patient parameter specific criteria include: whether the difference metric for a percentage of pacing indicates a presence or increase of pacing during the period; whether the difference metric for a heart rate indicates an increase in heart rate during the period; whether the difference metric for a heart rate variability indicates a decrease in heart rate variability during the period; whether the difference metric for a patient activity parameter indicates a decrease in patient activity during the period; whether a difference metric for a thoracic impedance indicates a fluid index during the period indicates an increase in the fluid index during the period; whether a difference metric for a parameter relating to a number, frequency, or duration of tachyarrhythmia events, e.g., NSTs, indicates the occurrence of one or more tachyarrhythmia events during the period; or whether a difference metric for a cardiac electrogram morphology parameter indicates change during the period. In some examples, processing circuitry may include difference metrics 176 in the score 178 based on satisfaction of these example criteria, e.g., in response to the criteria being satisfied.

Figure 13A:
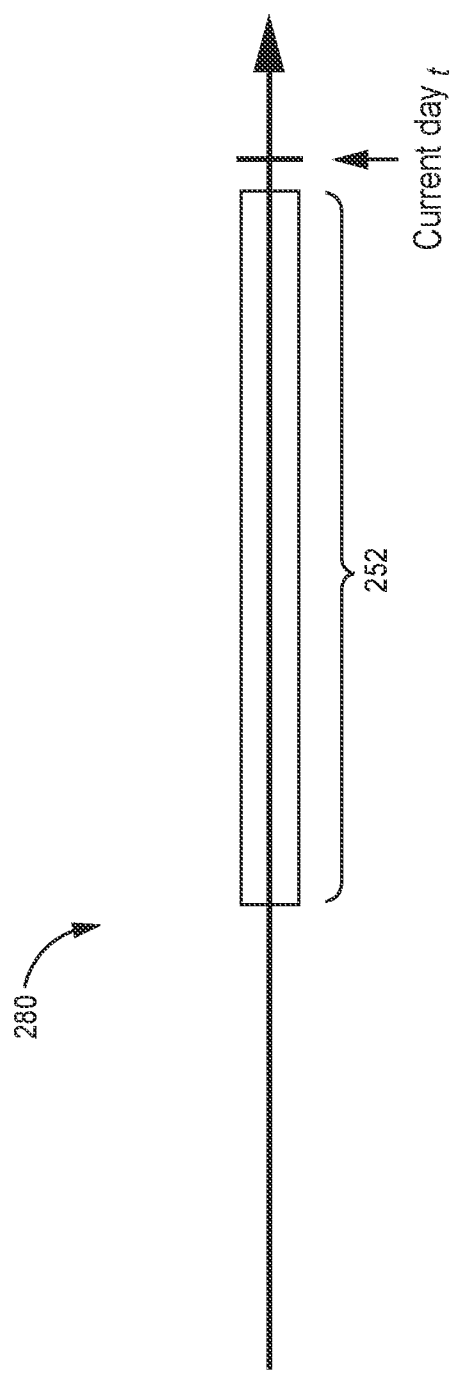
FIGS. 13A and 13B are timing diagrams illustrating example techniques for determining a window of N preceding periods.
Figure 13B:
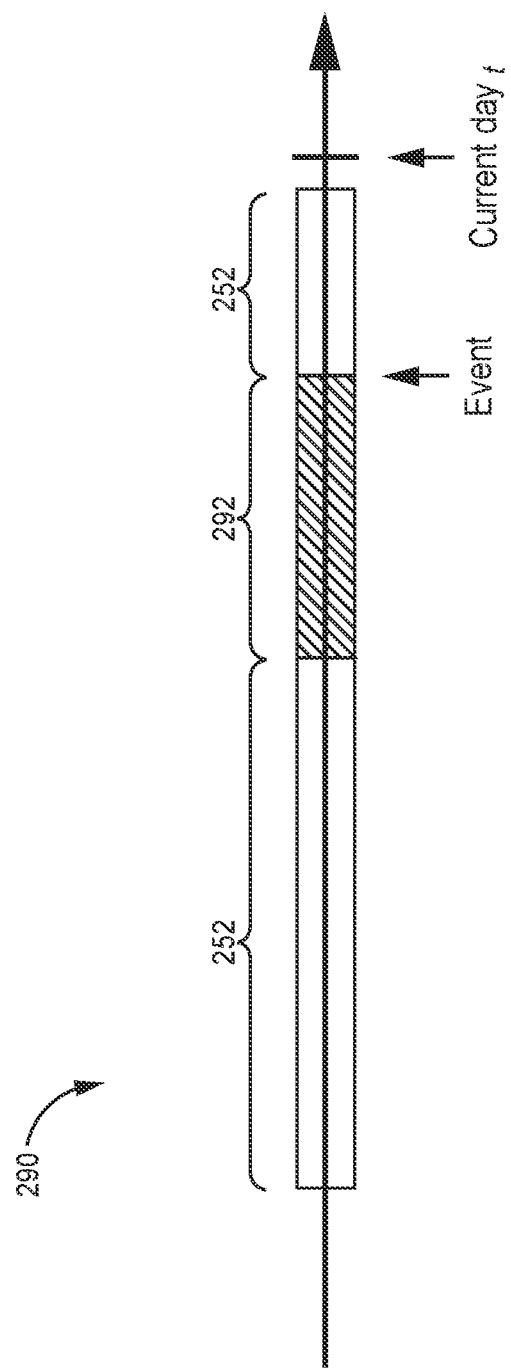

FIGS. 13A and 13B are respectively timing diagrams 280 and 290 illustrating example techniques for determining a window of N preceding periods. N is an integer constant number of preceding periods. Timing diagram 280 of FIG. 13A illustrates a window 252 of the N most recent periods preceding the current period, e.g., current day in the illustrated example.

Timing diagram 290 of FIG. 13B illustrates an example in which window 252 excludes one or more periods 292, such that the N preceding periods are not consecutive. In some examples, processing circuitry of a medical device system 8 is configured to detect the occurrence of the acute cardiac event, e.g., detect a ventricular tachyarrhythmia using any of the techniques described herein, during one of the plurality of periods. In some examples, in response to detecting the acute cardiac event, the processing circuitry excludes the period during which the acute cardiac event was detected from N periods that precede the current period, e.g., from window 252. In some examples, the processing circuitry additionally excludes one or more periods proximate to the period during which the acute cardiac event was detected from N periods, such as one or more periods immediately preceding or following the period during which the acute cardiac event was detected. In some examples, 2 to 10 periods, such as 6 periods immediately preceding, one period immediately following, and/or the current period, are excluded.

Figure 14:
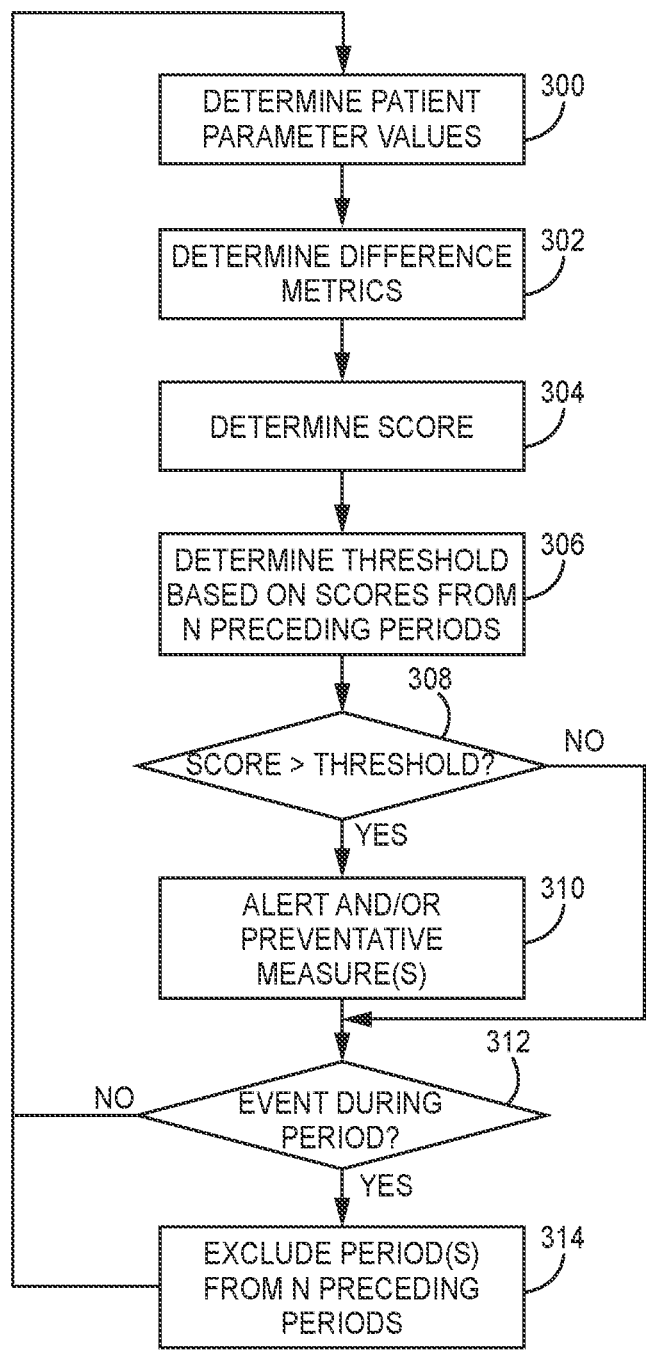
FIG. 14 is a flow diagram illustrating an example technique that may be implemented by a medical device system to provide an alert and/or preventative measure(s) in response to an acute cardiac event being predicted.

FIG. 14 is a flow diagram illustrating an example technique that may be implemented by a medical device system 8, e.g., processing circuitry of the medical device system, to provide an alert and/or preventative measure(s) in response to an acute cardiac event being predicted. The flowcharts of FIGS. 14-17 are intended to illustrate the functional operation of an IMD 10, external device 30, medical system 8, and other devices and systems described herein, and should not be construed as reflective of a specific form of software or hardware necessary to practice the methods described. Methods described in conjunction with flow diagrams presented herein may be implemented in a non-transitory computer-readable medium that includes instructions for causing a programmable processor to carry out the methods described. A non-transitory computer-readable medium includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented by processing circuitry hardware as execution of one or more software modules, which may be executed by themselves or in combination with other software.

The example methods illustrated by FIGS. 14-17 may be performed, by any one or more devices described herein, and may be performed, in part, by processing circuitry of any one or more devices described herein, such as by processing circuitry 160 of IMD 10 (which may correspond to any of ICD 10A, ICM 10B, ICD 10C, IPD 10D, or any other IMD), processing circuitry 200 of external device 30, processing circuitry 228 of server 224. For ease of description, the methods of FIGS. 14-16 will be described hereafter as being performed by processing circuitry 160 of IMD 10.

The example method of FIG. 14 may be performed for each of a plurality of consecutive periods. According to the example method of FIG. 14, processing circuitry 160 determines patient parameter values 174 for each of a plurality of patient parameters during the period (300). The patient parameters may include any of the patient parameters described herein, and processing circuitry 160 may determine at least some of the values 174 based on physiological signals generated by sensing circuitry 162 and/or sensors 166.

Processing circuitry 160 determines a respective difference metric 176 for each of the plurality patient parameters for the period (302). In some examples, processing circuitry 160 determines the respective difference metrics 176 based on differences between the current and immediately preceding values 174 of the patient parameter, e.g., using equation 1 or 2. Processing circuitry 160 determines a score 178 for the period based on the difference metrics 176 for the period, e.g., based on a sum of the difference metrics (304). In some examples, processing circuitry 160 determines the score 178 based on a sum of squares of the difference metrics, e.g., according to equation 3. In some examples, processing circuitry 160 applies a weight to one or more of the difference metrics when determining the score.

Processing circuitry 160 also determines a threshold 180 for the period based on the scores 178 of N preceding periods (306). In some examples, processing circuitry determines the score by applying a coefficient to the median of the scores 178 for the N preceding periods. Processing circuitry 160 determines whether the score 178 for the period is greater than (or greater than or equal to) the threshold 180 for the period (308). If the score 178 is greater than the threshold 180 (YES of 308), processing circuitry may provide an alert indicating that the acute cardiac event is predicted and/or control delivery of one or more preventative therapies (310).

Processing circuitry 160 also determines whether the acute cardiac event was in fact detected (rather than predicted) during the period (312). If the acute cardiac event is predicted (YES of 312), processing circuitry may exclude one or more periods, including the current period, from the window of N preceding periods using during subsequent periods (314).

Figure 15:
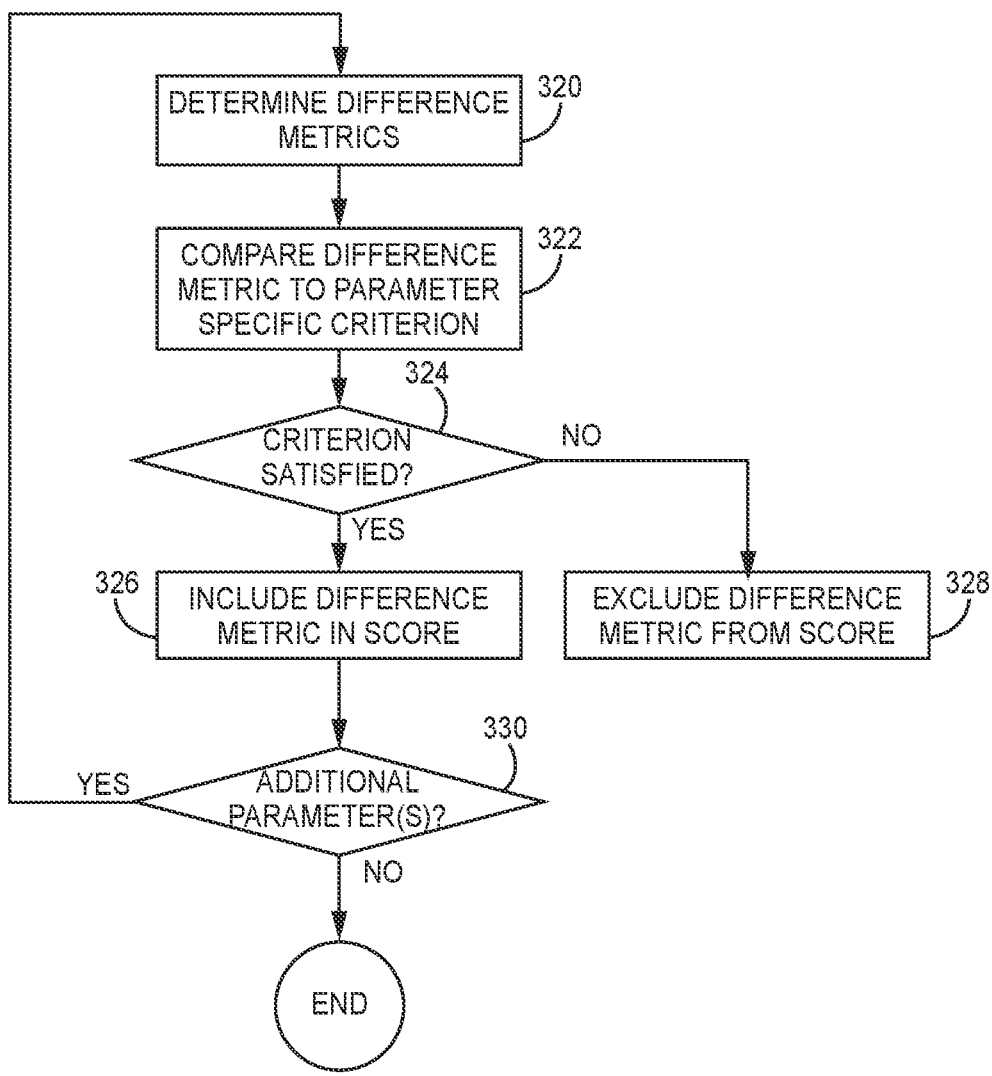
FIG. 15 is a flow diagram illustrating an example technique that may be implemented by a medical device system to determine a score based on a plurality of difference metrics associated with respective physiological parameters.

FIG. 15 is a flow diagram illustrating an example technique that may be implemented by a medical device system 8 to determine a score based on a plurality of difference metrics associated with respective patient parameters. The example technique described in FIG. 15 may be used, for example, by processing circuitry 160 of IMD 10 between blocks 302 and 304 of FIG. 14.

According to the example method of FIG. 15, processing circuitry 160 determines a difference metric for a particular patient parameter and for the current period (320). Processing circuitry 160 compares the difference metric to a patient parameter-specific criterion, e.g., as described above with respect to FIG. 12 (322). Processing circuitry 160 determines whether the difference metric 176 for the period satisfies the patient parameter-specific criterion (324).

If the criterion is satisfied (YES of 324), processing circuitry 160 includes the difference metric 176 in the score 178, e.g., sum of difference metrics, for the period (326). If the criterion is not satisfied (NO of 324), processing circuitry 160 excludes the difference metric 176 from the score 178 for the period (328). Processing circuitry 160 determines whether there are additional difference metrics 176 for additional patient parameters to which parameter-specific criteria are to be applied during the period (330).

Figure 16:
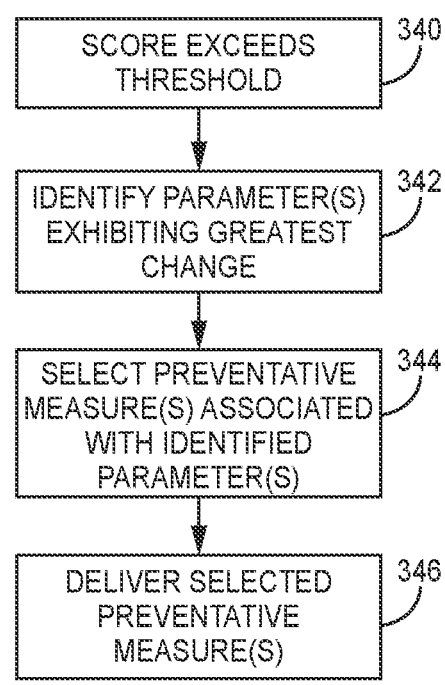
FIG. 16 is a flow diagram illustrating an example technique that may be implemented by a medical device system to select one or more preventative measure(s) for delivery in response to an acute cardiac event being predicted.

FIG. 16 is a flow diagram illustrating an example technique that may be implemented by a medical device system 8, clinician, or other user, to select one or more preventative measure(s) for delivery in response to an acute cardiac event being predicted. For ease of description, the example of FIG. 16 is described as being performed by processing circuitry 160 of IMD 10.

According to the example method of FIG. 16, processing circuitry 160 determines that the score 178 for the current period exceeds the threshold 180 for the period (340, e.g., YES of 308 of FIG. 14). Processing circuitry 160 determines which one or more patient parameters exhibited the greatest, or most significant, change during the period (342). For example, processing circuitry 160 may identify the one or more difference metrics 176 for the current having the greatest absolute value, or the greatest absolute value relative to a mean, median, or standard deviation of difference metrics for the parameter during the N preceding periods, e.g., determined as a percentage, ratio, or other normalized value.

Processing circuitry 160 selects one or more preventative measures, e.g., therapies configured to prevent the acute cardiac event, associated with the one or more identified patient parameters (344). In some examples, IMD 10 may be configured to deliver, and/or control one or more other devices to deliver, a plurality of different therapies configured to prevent the acute cardiac event. Different therapies may include different cardiac pacing algorithms, different types of, targets, and/or programs for neuromodulation, and delivery of different drugs, delivery of one or more drugs to different targets, and or delivery of one or more drugs according to different drug delivery regimens.

Memory 170 may store information associating one or more preventative therapies with one or more patient parameters, and processing circuitry 160 may select one or more preventative therapies according to the information stored in memory 170. The associations of therapies and patient parameters may be programmed by a clinician and/or determined based on an analysis of historical efficacy of a particular therapy in preventing an acute cardiac event, for patient 14 and/or a population of patients anatomically, physiologically, and or clinically similar to patient 14. Processing circuitry 160 controls IMD 10 or another medical device to deliver the selected preventative measure(s) (346). For example, if processing circuitry 160 determines that a patient parameter 174 associated with heart rate is consistently too fast at the time a patient parameter 174 associated with patient activity indicates no increase in physical activity, a vagal stimulation can be triggered to slow down the heart rate or down-driving pacing can be triggered. On the other hand, if processing circuitry 160 determines that a patient parameter 174 associated with heart rate is slow in combination with an occurrence of more PVCs, then overdrive pacing can be triggered.

Figure 17:
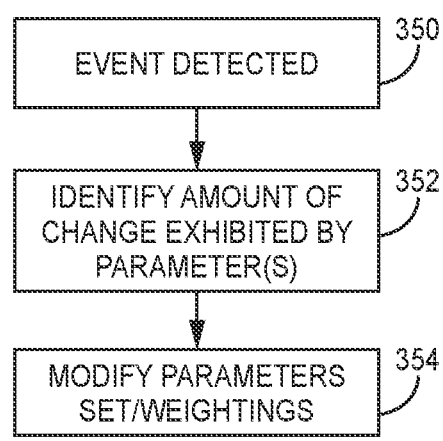
FIG. 17 is a flow diagram illustrating an example technique that may be implemented by a medical device system to modify a set of patient parameters or weightings applied to patient parameters used to determine whether an acute cardiac event is predicted.

FIG. 17 is a flow diagram illustrating an example technique that may be implemented by a medical device system to determine and/or modify a set of patient parameters or weightings applied to patient parameters used to determine whether an acute cardiac event is predicted. For ease of description, the example of FIG. 17 is described as being performed by processing circuitry 160 of IMD 10.

According to the example method of FIG. 17, processing circuitry 160 detects an acute cardiac event, e.g., ventricular tachyarrhythmia, during a period (350). Processing circuitry 160 determines the amount and/or significance of change exhibited during the period for the plurality of patient parameters (352). For example, processing circuitry 160 may identify the absolute values of difference metrics, or the absolute values relative to a mean, median, or standard deviation of difference metrics for the parameter during the N preceding periods. In this manner, processing circuitry 160 may determine the relative significance or importance of the various patient parameters in predicting the detected cardiac event. Based on the relative significance or importance of the patient parameters, processing circuitry 160 may include or exclude certain patient parameters from use in the techniques to predict the acute cardiac event, or modify patient parameter-specific weighting parameters applied to the difference metrics to determine a score (e.g., sum-based) for a period, which may emphasize or de-emphasize the importance of certain patient parameters (354).

Figure 18:

FIGS. 18-22 are tables (360, 370, 380, 390, and 400, respectively) of experimental results illustrating the performance of the example techniques of this disclosure in predicting ventricular tachyarrhythmia. In FIGS. 18-20, each row may correspond to a different device (e.g., a different device serial number). In FIGS. 21 and 22, each row may correspond to a different patient identification number. In general, each row may correspond to a different patient. Twenty-five ICD-indicated patients were prospectively enrolled. After ICD implantation, each patient underwent weekly data collections for six-month follow-up and appropriate VTVF events were determined. A VTVF event could be a single discrete VT or VF episode or a VTVF storm with inter-episode interval less than 24 hours. An algorithm was developed to create a weighted score based on the assessment of directional changes in values of multiple device-derived (e.g., Cardiac Compass®) patient parameters over a 15-day moving window. The algorithm was then retrospectively tested to compare the weighted score one day before an event vs. the weighted score over 15-day window. The efficiency of the prediction in one day before a VTVF event was determined with the sensitivity and the specificity.

The patients enrolled in this study had LVEF 44.5±15.2% and NYHA class 1.3±0.6. In the enrolled 25 patients, 11 (44%) had coronary heart disease, 14 (56%) had cardiomyopathy, 7 (28%) had hypertension, and 20 (80%) had a history of sustained VT or VF. Of 25 patients, 10 patients (40%) developed a total of 123 appropriate VTVF episodes (12.4±13.2, median 5 per patient) that were terminated by ICD therapies. Of these 123 episodes, 100 were classified as VT while remaining 23 episodes were VF. When the weighted-score algorithm was tested in all 25 patients, the prediction of VTVF events one day before the occurrence had a 100% sensitivity and 74% specificity.

The experimental results, e.g., as illustrated in FIGS. 17-19, demonstrate that VTVF events can be predicted one day in advance according to the techniques of this disclosure, which may provide a time window for executing appropriate measures to prevent VTVF occurrence, especially for VTVF storms.

FIG. 23 is a table 380 illustrating a receiver operator characteristic for a coefficient used to determine a threshold 180 for determining whether an acute cardiac event is predicted according to the example techniques of this disclosure. As described in greater detail above, processing circuitry 160 may determine threshold 180 for the current period by applying a coefficient to a median of scores 178 for N preceding periods. The value of the coefficient may be determined and/or modified, based on a receiver operator characteristic for the coefficient relative to the sensitivity and specificity of acute cardiac event prediction according the techniques of this disclosure using different values of the coefficient. The data for determining the receiver operator characteristic may be historical data from the patient, or a population of similar patients and/or experimental subjects.

Figure 24:
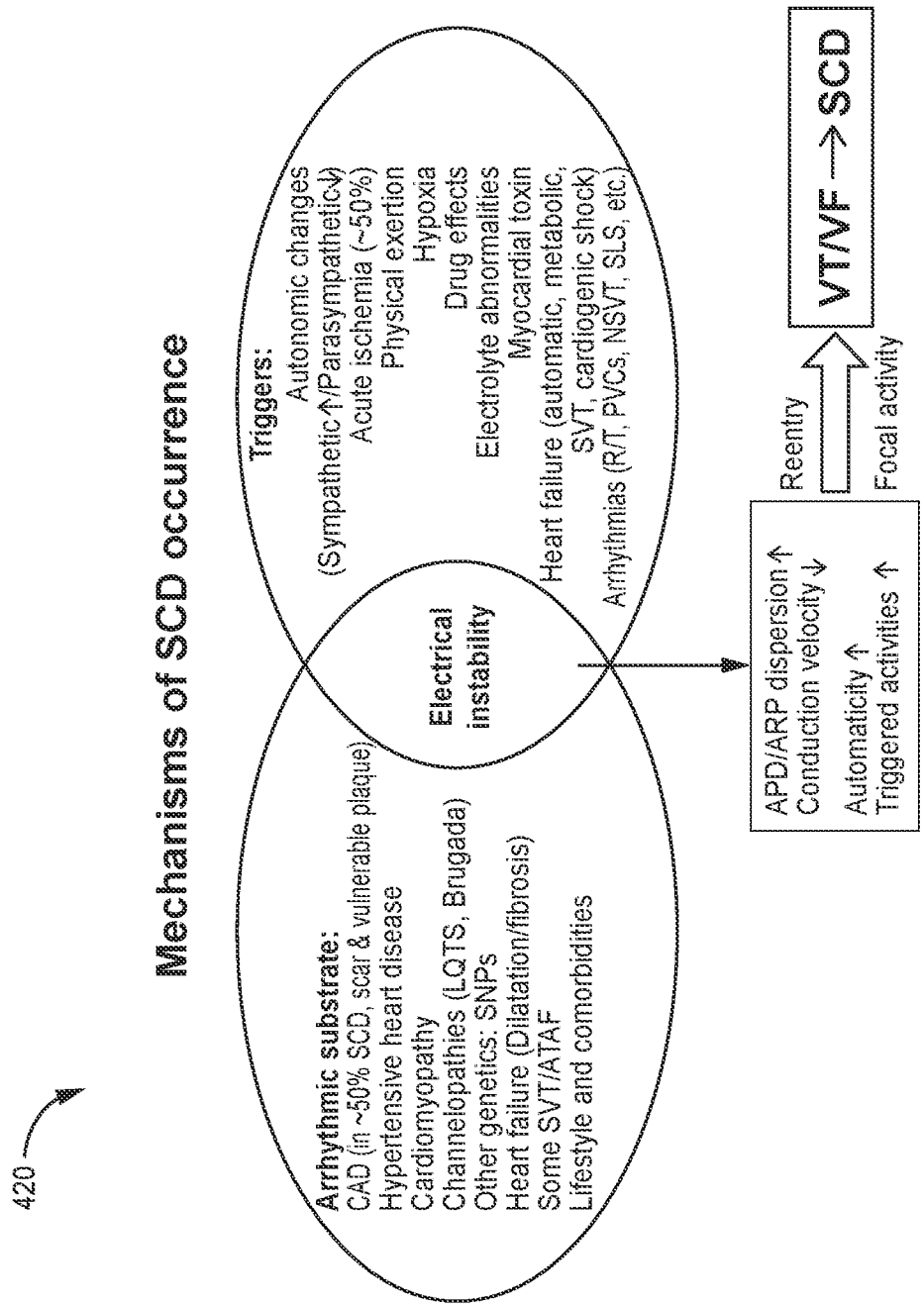
FIG. 24 is a conceptual diagram illustrating patient parameters, e.g., physiological and pathophysiological parameters, that may contribute to the occurrence of an acute cardiac event.

FIG. 24 is a conceptual diagram 420 illustrating patient parameters, e.g., physiological and pathophysiological parameters, that may contribute to the occurrence of an acute cardiac event. In general, the techniques of this disclosure enable prediction of an acute cardiac event based on a combined score from a plurality of patient parameters, which may include clinical parameters and/or parameters derived from a medical device. Changes in the parameters may reflect changes in a patient's electrophysiological substrate and/or anatomical milieu that precede an acute cardiac event.

The techniques described herein may use a moving window computation for all possible risk variables. The techniques described herein may include calculating a weighted score for prediction of imminent VTVF events. Such a calculation, and other techniques, are based on the findings that risk factors change in a temporal manner and, generally, there may not be a single variable that can consistently be used predict VTVF events in the same patient or the population. The possible risk variables for consideration in the present techniques may include: (1) pathological substrates (e.g., cardiac diseases, myocardial infarction, etc.), (2) daily monitoring parameters (e.g., autonomic signature, thoracic impedance, ventricular pacing, etc.), such as included in Cardiac Compass®, (3) daily non-VTVF arrhythmic burden (e.g., NSVT, ATAF, PVC burden, etc.), and (4) cardiac electrogram alternations (such as T-wave alternans, repolarization alternations, QRS duration and fragmentation, etc.). Further illustration of the possible risk variables may be seen in FIG. 24.

Patient parameters relating to arrhythmic substrate may include or indicate the presence or extent of: coronary artery disease (CAD), such as scar and vulnerable plaque; hypertensive heart disease; cardiomyopathy; channelopathies, with may be reflected in long QT syndrome (LQTS) or Brugada syndrome; other genetic predisposition to acute cardiac events, such as single nucleotide polymorphism; heart failure, including dilatation and/or fibrosis; the presence and/or extent of sustained VT, AT, and/or AF; patient lifestyle and comorbidities. Patient parameters relating to physiological triggers for acute cardiac events may include or indicate the presence or extent of: autonomic changes, such as increase sympathetic and/or decreased parasympathetic drive; acute ischemia; physical exertion; hypoxia; drug effects; electrolyte abnormalities; myocardial toxin; heart failure, which may be autonomic, metabolic, due to supraventricular tachycardia (SVT), and/or cardiogenic shock; or the presence of other arrhythmias, such as PVCs, R-on-T events, non-sustained ventricular tachycardias, short-long-short rhythm, or the like. The occurrence of one or more triggers in the presence of one or more indicators of arrhythmic substrate may lead to electrical instability, as illustrated in FIG. 24, and consequently be particularly predictive of the occurrence of an acute cardiac event. For example, as illustrated in FIG. 24, the occurrence of one or more triggers in the presence of one or more indicators of arrhythmic substrate may lead to increase ADP/ARP dispersion, decrease conduction velocity, increase automaticity, and/or increased triggered activities. The illustration of FIG. 24 may be considered a matrix of possible patient parameters that can be monitored in combination to predict an acute cardiac event, such as ventricular tachyarrhythmia.

Any of the above patient parameters, or any patient parameters related to these conditions, may be used to predict acute cardiac events according to the techniques of this disclosure. These parameters may be detected by processing circuitry 160 based on device-derived physiological parameters and/or indications from a clinician, e.g., via an external device 30 or other computing device. For example, changes in heart rate, heart rate variability, and the occurrence of PVCs may indicate changes in sympathetic/parasympathetic drive.

A sudden oscillation in any of the patient parameters described herein may be considered a risk of an acute cardiac event. A sum of oscillations of several parameters may be considered as a combined risk score with the largest oscillation contributing to the combined score the most. This concept may provide weighted score or contributor. The techniques described herein, e.g., including determining a score for a period based on a sum of difference metrics for a plurality of patient parameters and comparing the score to a longer term mean or median of the scores, may indicate the sum of the oscillations and allow identification of the most significant patient parameters that contribute to the occurrence cardiac events for a particular patient.

The patient parameters used to predict acute cardiac events for a particular patient may be pre-defined (such as use only T-wave alternans and/or the frequency of non-sustained ventricular tachycardia). In some examples, many patient parameters are monitored to predict acute cardiac events and any (or some) of the parameters that show undesired changes will be weighted in the prediction score. The parameters that show significant oscillations prior to an acute cardiac event may vary from patient-to-patient, or from event-to-event for a particular patient. For example, one event may be predicted based on significant oscillations in T-wave alternans and the frequency of non-sustained ventricular tachycardia, while another is predicted based on significant oscillations in T-wave alternans and heart rate variability. In this manner, the prediction may be tailored to a particular patient, e.g., individual-based prediction.

As described herein, the techniques of this disclosure also allow processing circuitry 160 to determine the most important patient parameter(s) that contributed to the suprathreshold score and, consequently, one or more likely causes of the cardiac event. As described herein, this may be useful for determining and/or adjusting over time a set of parameters and/or weightings used to determine scores and predict cardiac events for a particular patient. In addition, as described herein, one or more preventative measures may be selected based on the identified significant parameters and most likely causes of the event. The targeted measures selected to prevent the cardiac event in this manner may be referred to as predictor-guided preventative measure(s).

The associations of patient-parameters and targeted preventative measures may be configured based on known or determined relationships between patient parameters for causing cardiac events. For example, if an event occurrence needs the co-existence of parameters A and B or A and C, parameter A is the most important contributor, and a preventative measure configured to reduce or counteract the oscillation in parameter A could be delivered. Of course, preventive measure targeted to parameters B or C could additionally or alternatively be delivered.

In an example, if the major score contributor is a reduction in HRV (e.g., which may be an indication of sympathetic surge), then vagal stimulation (e.g., using neuromodulation) may be initiated. For example, if T-wave alternans change increases, a pacing algorithm may be triggered to reduce T-wave alternans. Other methods may include drug perfusion, termination of a physical activity, or other techniques, such as may be based on the rick contributor analysis in the calculated weighted score.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

In an example, a medical device system may comprise means for performing any of the methods or techniques described herein.

In an example, a non-transitory computer-readable storage medium may comprise instructions, that when executed by processing circuitry of a medical device system, cause the medical device system to perform any of the methods or techniques described herein.

The following numbered clauses demonstrate one or more aspects of this disclosure.

Clause 1: In one example, a medical device system comprises sensing circuitry configured to generate one or more physiological signals of a patient; and processing circuitry that, for each of a plurality of periods, is configured to: determine a respective value for each of a plurality of patient parameters, wherein, for one or more of the plurality of patient parameters, the respective values are determined based on the one or more physiological signals generated during the period; for each of the plurality of patient parameters, determine a difference metric for a current period for each of the plurality of periods based on a value of the patient parameter determined for the current period and a value of the patient parameter determined for an immediately preceding period of the plurality periods; determine a score for the current period based on a sum of the difference metrics for the current period for the one or more of the plurality of patient parameters; determine a threshold for the current period based on scores determined for N periods of the plurality of periods that precede the current period, wherein N is an integer constant; compare the score for the current period to the threshold for the current period; and determine whether to generate an alert indicating that an acute cardiac event of the patient is predicted based on the comparison.

Clause 2: In some examples of the system of clause 1, the processing circuitry is configured to determine a difference between the value of the patient parameter determined for the current period and the value of the patient parameter determined for the immediately preceding period as the difference metric for the current period.

Clause 3: In some examples of the system of clause 1 or 2, the processing circuitry is configured to determine the difference metric for the current period as a ratio between: a difference between the value of the patient parameter determined for the current period and the value of the patient parameter determined for the immediately preceding period; and a measure of variation of values of the patient parameter determined for the N periods of the plurality of periods that precede the current period.

Clause 4: In some examples of the system of clause 3, the measure of variation comprises a standard deviation of the values of the patient parameter determined for the N periods of the plurality of periods that precede the current period.

Clause 5: In some examples of the system of any of clauses 1-4, the processing circuitry is configured to determine the score for the current period at least by determining a sum of squares of the difference metrics for the current.

Clause 6: In some examples of the system of any of clauses 1-5, the processing circuitry is configured to determine the threshold based on a median of the scores determined for the N periods preceding the current period.

Clause 7: In some examples of the system of any of clauses 1-6, the processing circuitry is configured to: compare one or more of the difference metrics for the current period to a patient parameter specific criterion; and determine whether to include the one or more of the difference metrics in the sum based on the comparison.

Clause 8: In some examples of the system of any of clauses 1-7, the alert indicates that a ventricular tachyarrhythmia is predicted.

Clause 9: In some examples of the system of any of clauses 1-8, the processing circuitry is configured to: detect the acute cardiac event during one of the plurality of periods; and exclude the period during which the acute cardiac event was detected from N periods that precede the current period.

Clause 10: In some examples of the system of any of clauses 1-9, the system further comprises therapy delivery circuitry configured to deliver a therapy to the patient to prevent the predicted acute cardiac event, wherein the processing circuitry is configured to determine whether to control the therapy delivery circuitry to deliver the therapy based on the comparison of the score for the current period to the threshold for the current period.

Clause 11: In some examples of the system of clause 10, the therapy delivery circuitry is configured to deliver a plurality of therapies to the patient to prevent the predicted acute cardiac event, and wherein the processing circuitry is configured to: for each of the plurality of patient parameters, compare the difference metric determined for the current period to difference metrics determined for the N periods preceding the current period; identify one of the plurality of patient parameters having a most significant change in the difference metric from the N periods to the current period; select one of the plurality of therapies associated with the identified one of the plurality of patient parameters; and control the therapy delivery circuitry to deliver the selected one of the plurality of therapies.

Clause 12: In some examples of the system of any of clauses 1-11, the system further comprises an implantable medical device that comprises the sensing circuitry and the processing circuitry.

Clause 13: In some examples of the system of clause 12, the implantable medical device comprises an implantable cardioverter defibrillator further comprising therapy delivery circuitry configured to deliver anti-tachyarrhythmia shocks.

Clause 14: In some examples of the system of clause 12 or 13, the implantable medical device comprises a leadless monitor comprising a housing configured for subcutaneous implantation that houses the sensing circuitry and the processing circuitry, wherein the housing includes a plurality of electrodes coupled to the sensing circuitry, and wherein the sensing circuitry is configured to generate a subcutaneous cardiac electrogram based on cardiac signals sensed via the electrodes.

Clause 15: In some examples of the system of any of clauses 1-14, the processing circuitry is further configured to: identify one or more of the plurality of patient parameters that contributed to the score being greater than the threshold, wherein the processing circuitry identifies the one or more of the plurality of patient parameters having most significant changes in the difference metric from the N periods to the current period as the one or more of the plurality of patient parameters that contributed to the score being greater than the threshold; and to at least one of: exclude a patient parameter from the score for a subsequent period, include a patient parameter for a subsequent period, or modify one or more weights applied to one or more of the difference metrics when determining the score based on the identified one or more patient parameters.

Clause 16: In some examples of the system of clause 15, the processing circuitry is configured to select one or more preventative measures to deliver to the patient based on the one or more identified patient parameters that contributed to the score being greater than the threshold.

Clause 17: In some examples, a method comprises generating, by sensing circuitry of a medical device system, one or more physiological signals of a patient; and for each of a plurality of periods, by processing circuitry of the medical device system: determining a respective value for each of a plurality of patient parameters, wherein, for one or more of the plurality of patient parameters, the respective values are determined based on the one or more physiological signals generated during the period; for each of the plurality of patient parameters, determining a difference metric for a current period for each of the plurality of periods based on a value of the patient parameter determined for the current period and a value of the patient parameter determined for an immediately preceding period of the plurality periods; determining a score for the current period based on a sum of the difference metrics for the current period for the one or more of the plurality of patient parameters; determining a threshold for the current period based on scores determined for N periods of the plurality of periods that precede the current period, wherein N is an integer constant; comparing the score for the current period to the threshold for the current period; and determining whether to generate an alert indicating that an acute cardiac event of the patient is predicted based on the comparison.

Clause 18: In some examples of the method of clause 17, determining the difference metric for the current period comprises determining a difference between the value of the patient parameter determined for the current period and the value of the patient parameter determined for the immediately preceding period.

Clause 19: In some examples of the method clause 17 or 18, determining the difference metric for the current period comprises determining a ratio between: a difference between the value of the patient parameter determined for the current period and the value of the patient parameter determined for the immediately preceding period; and a measure of variation of values of the patient parameter determined for the N periods of the plurality of periods that precede the current period.

Clause 20: In some examples of the method of clause 20: the measure of variation comprises a standard deviation of the values of the patient parameter determined for the N periods of the plurality of periods that precede the current period.

Clause 21: In some examples of the method of any of clauses 17-20, determining the score for the current period comprises determining a sum of squares of the difference metrics for the current period.

Clause 22: In some examples of the method of any of clauses 17-21, determining the threshold for the current period comprises determining a median of the scores determined for the N periods preceding the current period.

Clause 23: In some examples of the method of any of clauses 17-22, the method further comprises, by the processing circuitry: comparing one or more of the difference metrics for the current period to a patient parameter specific criterion; and determining whether to include the one or more of the difference metrics in the sum based on the comparison.

Clause 24: In some examples of the method of any of clauses 17-23, the alert indicates that a ventricular tachyarrhythmia is predicted.

Clause 25: In some examples of the method of any of clauses 17-24, the method further comprises, by the processing circuitry: detecting the acute cardiac event during one of the plurality of periods; and excluding the period during which the acute cardiac event was detected from N periods that precede the current period.

Clause 26: In some examples of the method of any of clauses 17-25, the method further comprises, by the processing circuitry of the medical device system, determining whether to control therapy delivery circuitry of the medical device system to deliver a therapy to the patient to prevent the predicted acute cardiac event based on the comparison of the score for the current period to the threshold for the current period.

Clause 27: In some examples of the method of clause 26, the therapy delivery circuitry is configured to deliver a plurality of therapies to the patient to prevent the predicted acute cardiac event, the method further comprising, by the processing circuitry: for each of the plurality of patient parameters, comparing the difference metric determined for the current period to difference metrics determined for the N periods preceding the current period; identifying one of the plurality of patient parameters having a most significant change in the difference metric from the N periods to the current period; selecting one of the plurality of therapies associated with the identified one of the plurality of patient parameters; and controlling the therapy delivery circuitry to deliver the selected one of the plurality of therapies.

Clause 28: In some examples of the method of any of clauses 17-27, the method further comprises identifying one or more of the plurality of patient parameters that contributed to the score being greater than the threshold; identifying the one or more of the plurality of patient parameters that contributed to the score being greater than the threshold comprises identifying one or more of the plurality of patient parameters having most significant changes in the difference metric from the N periods to the current period; and at least one of: excluding a patient parameter from the score for a subsequent period, including a patient parameter for a subsequent period, or modifying one or more weights applied to one or more of the difference metrics when determining the score based on the identified one or more patient parameters.

Clause 29: In some examples of the method of clause 28, the method further comprises selecting one or more preventative measures to deliver to the patient based on the one or more identified patient parameters that contributed to the score being greater than the threshold.

Clause 30: In some examples, a medical device system comprises: means for generating one or more physiological signals of a patient; and for each of a plurality of periods: means for determining a respective value for each of a plurality of patient parameters, wherein, for one or more of the plurality of patient parameters, the respective values are determined based on the one or more physiological signals generated during the period; for each of the plurality of patient parameters, means for determining a difference metric for a current period for each of the plurality of periods based on a value of the patient parameter determined for the current period and a value of the patient parameter determined for an immediately preceding period of the plurality periods; means for determining a score for the current period based on a sum of the difference metrics for the current period for the one or more of the plurality of patient parameters; means for determining a threshold for the current period based on scores determined for N periods of the plurality of periods that precede the current period, wherein N is an integer constant; means for comparing the score for the current period to the threshold for the current period; and means for determining whether to generate an alert indicating that an acute cardiac event of the patient is predicted based on the comparison.

Clause 31: In some examples, a non-transitory computer-readable storage medium comprises instructions, that when executed by processing circuitry of a medical device system, cause the medical device system to: receive one or more physiological signals of a patient; and for each of a plurality of periods: determine a respective value for each of a plurality of patient parameters, wherein, for one or more of the plurality of patient parameters, the respective values are determined based on the one or more physiological signals generated during the period; for each of the plurality of patient parameters, determine a difference metric for a current period for each of the plurality of periods based on a value of the patient parameter determined for the current period and a value of the patient parameter determined for an immediately preceding period of the plurality periods; determine a score for the current period based on a sum of the difference metrics for the current period for the one or more of the plurality of patient parameters; determine a threshold for the current period based on scores determined for N periods of the plurality of periods that precede the current period, wherein N is an integer constant; compare the score for the current period to the threshold for the current period; and determine whether to generate an alert indicating that an acute cardiac event of the patient is predicted based on the comparison.

Various aspects of the disclosure have been described. These and other aspects are within the scope of the following claims.

What is claimed is:

1. A system comprising:
   an insertable cardiac monitor (ICM) comprising:
   a housing configured for subcutaneous implantation within a patient, the housing having a length extending from a proximal end of the housing to a distal end of the housing, a width, and a depth,
   wherein the length is greater than the width and the width is greater than the depth, and
   wherein the length is within a range from 40 millimeters (mm) to 60 mm;
   a heart sound sensor, wherein the ICM is configured to sense heart sounds of the patient via the heart sound sensor; and
   a plurality of electrodes on the housing, wherein the ICM is configured to sense an electrocardiogram (ECG) of the patient via the plurality of electrodes;
   a remote computing device; and
   processing circuitry of at least one of the insertable cardiac monitor or the remote computing device, the processing circuitry configured to:
   periodically determine a respective value for each of a plurality of physiological parameters based on one or more of the heart sounds or the ECG, wherein at least a first physiological parameter of the plurality of physiological parameters is determined based on the heart sounds and at least a second physiological parameter of the plurality of physiological parameters is determined based on the ECG, wherein the first physiological parameter comprises a frequency of occurrence of an S3 heart sound;
output trends of the periodically determined values of the physiological parameters at the remote computing device; and
determine whether to present an indication of a heart failure event based on an analysis of the trends of the periodically determined values of the physiological parameters, wherein to perform the analysis of the trends the processing circuitry is configured to:
determine a first variation value of at least one physiological parameter of the plurality of physiological parameters for a first period and a second variation value of the at least one of the physiological parameter for a second period preceding the first period; and
determine whether a comparison of the first variation value and the second variation value satisfies a criterion.

2. The system of claim 1, wherein the indication of the heart failure event comprises an indication of a risk of the heart failure event.

3. The system of claim 1, wherein to determine whether to present the indication of the heart failure event based on an analysis of the trends of the periodically determined values of the physiological parameters, the processing circuitry is configured to apply respective weights to each of the plurality of physiological parameters.

4. The system of claim 1, wherein the plurality of physiological parameters comprise a measurement of an S1 heart sound.

5. The system of claim 1, wherein the plurality of physiological parameters comprise one or more of: a morphological measurement of an S1 and/or S2 heart sound, or a presence/frequency of an S4 heart sound.

6. The system of claim 1, wherein the plurality of physiological parameters comprise a morphological measurement of an S1 heart sound.

7. The system of claim 1, wherein the ICM comprises a patient activity sensor configured to sense activity/posture of the patient, and the processing circuitry is configured to periodically determine values of at least one physiological parameter of the plurality of physiological parameters based on the sensed activity/posture.

8. The system of claim 1, wherein the ICM comprises one or more accelerometers, and the processing circuitry is configured to periodically determine values of at least one physiological parameter of the plurality of physiological parameters based on a signal from the one or more accelerometers.

9. The system of claim 1, wherein the processing circuitry is configured to determine whether to present the indication of the heart failure event based on a comparison of a physiological parameter value for a current period to a threshold determined based on physiological parameter values for previous periods.

10. The system of claim 1, wherein the plurality of physiological parameters comprises at least one of a heart rate variability parameter or a night heart rate parameter.

11. The system of claim 1, wherein the housing defines an elongated rectangular prism comprising a rounded distal end and a rounded proximal end.

12. The system of claim 1, wherein the plurality of electrodes comprises a first electrode that is substantially flat and a second electrode that comprises a three-dimensional, curved configuration.

13. The system of claim 1, wherein a volume of the ICM is less than 1.5 cubic centimeters.

14. A non-transitory computer-readable storage medium comprising program instructions that, when executed by processing circuitry, cause the processing circuitry to:
periodically determine a respective value for each of a plurality of physiological parameters based on one or more of heart sounds or an electrocardiogram (ECG) sensed by an insertable cardiac monitor (ICM), wherein at least a first physiological parameter of the plurality of physiological parameters is determined based on the heart sounds and at least a second physiological parameter of the plurality of physiological parameters is determined based on the ECG, wherein the first physiological parameter comprises a frequency of occurrence of an S3 heart sound, wherein the ICM comprises:
a housing configured for subcutaneous implantation within a patient, the housing having a length extending from a proximal end of the housing to a distal end of the housing, a width, and a depth,
wherein the length is greater than the width and the width is greater than the depth, and
wherein the length is within a range from 40 millimeters (mm) to 60 mm;
a heart sound sensor, wherein the ICM is configured to sense the heart sounds via the heart sound sensor; and
a plurality of electrodes on the housing, wherein the ICM is configured to sense the ECG via the plurality of electrodes;
output trends of the periodically determined values of the physiological parameters at a remote computing device; and
determine whether to present an indication of a heart failure event based on an analysis of the trends of the periodically determined values of the physiological parameters, wherein to perform the analysis of the trends the instructions cause the processing circuitry to:
determine a first variation value of at least one physiological parameter of the plurality of physiological parameters for a first period and a second variation value of the at least one of the physiological parameter for a second period preceding the first period; and
determine whether a comparison of the first variation value and the second variation value satisfies a criterion.

15. The non-transitory computer-readable storage medium of claim 14, wherein the indication of the heart failure event comprises an indication of a risk of the heart failure event.

16. The non-transitory computer-readable storage medium of claim 14, wherein the plurality of physiological parameters comprise a measurement of an S1 heart sound.

17. The non-transitory computer-readable storage medium of claim 14, wherein the plurality of physiological parameters comprise one or more of: a morphological measurement of an S1 and/or S2 heart sound, or a presence/frequency of an S4 heart sound.

18. The system of claim 1, wherein the ICM is configured to sense the ECG via a proximal electrode of the plurality of electrodes at the proximal end and a distal electrode of the plurality of electrodes at the distal end.

19. The non-transitory computer-readable storage medium of claim 14, wherein the plurality of physiological parameters comprise a morphological measurement of an S1 heart sound.

20. The non-transitory computer-readable storage medium of claim 14, wherein the ICM comprises a patient activity sensor configured to sense activity/posture of the patient, the wherein non-transitory computer-readable storage medium further comprising instructions that, when executed by the processing circuitry, cause the processing circuitry to periodically determine values of at least one physiological parameter of the plurality of physiological parameters based on the sensed activity/posture.

21. An insertable cardiac monitor (ICM) comprising:
a housing configured for subcutaneous implantation within a patient, the housing having a length extending from a proximal end of the housing to a distal end of the housing, a width, and a depth,
wherein the length is greater than the width and the width is greater than the depth,
wherein the length is within a range from 40 millimeters (mm) to 60 mm;
a heart sound sensor, wherein the ICM is configured to sense heart sounds of the patient via the heart sounds sensor;
a plurality of electrodes on the housing, wherein the ICM is configured to sense an electrocardiogram (ECG) of the patient via the plurality of electrodes; and
communication circuitry within the housing; and
processing circuitry within the housing, the processing circuitry configured to:
cause the communication circuitry to establish one or more telemetry communication sessions with a remote computing device; and
cause the communication circuitry to, during the one or more telemetry communication sessions, communicate values of a plurality of physiological parameters periodically determined based at least in part on one or more of the heart sounds or the ECG to the remote computing device, wherein at least a first physiological parameter of the plurality of physiological parameters is determined based on the heart sounds and at least a second physiological parameter of the plurality of physiological parameters is determined based on the ECG, wherein the first physiological parameter comprises a frequency of occurrence of an S3 heart sound, wherein the remote computing device is configured to output trends of the periodically determined values of the physiological parameters and is further configured to determine whether to present an indication of a heart failure event based on an analysis of the trends of the periodically determined values of the physiological parameters, wherein to perform the analysis of the trends the processing circuitry is configured to:
determine a first variation value of at least one physiological parameter of the plurality of physiological parameters for a first period and a second variation value of the at least one of the physiological parameter for a second period preceding the first period; and
determine whether a comparison of the first variation value and the second variation value satisfies a criterion.

22. The ICM of claim 21, wherein the ICM is configured to sense the ECG via a proximal electrode of the plurality of electrodes at the proximal end and a distal electrode of the plurality of electrodes at the distal end.

23. The insertable cardiac monitor (ICM) of claim 21, wherein the plurality of physiological parameters comprises a measurement of an S1 heart sound.

24. A system comprising:
an insertable cardiac monitor (ICM) comprising:
a housing configured for subcutaneous implantation within a patient, the housing having a length extending from a proximal end of the housing to a distal end of the housing, a width, and a depth,
wherein the length is greater than the width and the width is greater than the depth, and
wherein the length is within a range from 40 millimeters (mm) to 60 mm;
a heart sound sensor, wherein the ICM is configured to sense heart sounds of the patient via the heart sound sensor; and
a plurality of electrodes on the housing, wherein the ICM is configured to sense an electrocardiogram (ECG) of the patient via the plurality of electrodes;
means for periodically determining a respective value for each of a plurality of physiological parameters based on one or more of the heart sounds or the ECG, wherein at least a first physiological parameter of the plurality of physiological parameters is determined based on the heart sounds and at least a second physiological parameter of the plurality of physiological parameters is determined based on the ECG, wherein the first physiological parameter comprises a frequency of occurrence of an S3 heart sound;
means for outputting trends of the periodically determined values of the physiological parameters at the remote computing device; and
means for determining whether to present an indication of a heart failure event based on an analysis of the trends of the periodically determined values of the physiological parameters, wherein to perform the analysis of the trends the means for determining comprises:
means for determining a first variation value of at least one physiological parameter of the plurality of physiological parameters for a first period and a second variation value of the at least one of the physiological parameter for a second period preceding the first period; and
means for determining whether a comparison of the first variation value and the second variation value satisfies a criterion.

25. The system of claim 24, wherein the plurality of physiological parameters comprises a measurement of an S1 heart sound.

* * * * *